(12) United States Patent
Varanasi et al.

(10) Patent No.: US 10,898,618 B2
(45) Date of Patent: Jan. 26, 2021

(54) AMORPHOUS SILICON OXIDE, AMORPHOUS SILICON OXYNITRIDE, AND AMORPHOUS SILICON NITRIDE THIN FILMS AND USES THEREOF

(71) Applicants: THE TEXAS A&M UNIVERSITY SYSTEM, College Station, TX (US); BOARD OF REGENTS, UNIVERSITY OF TEXAS SYSTEM, Austin, TX (US); UT-BATTELLE, LLC, Oak Ridge, TN (US)

(72) Inventors: Venu Varanasi, Lewisville, TX (US); Pranesh Aswath, Grapevine, TX (US); Megen Maginot, Beeville, TX (US); Nickolay V. Lavrick, Knoxville, TN (US)

(73) Assignees: THE TEXAS A&M UNIVERSITY SYSTEM, College Station, TX (US); BOARD OF REGENTS, UNIVERSITY OF TEXAS SYSTEM, Austin, TX (US); UT-BATTELLE, LLC, Oak Ridge, TN (US)

( * ) Notice: Subject to any disclaimer, the term of this patent is extended or adjusted under 35 U.S.C. 154(b) by 85 days.

(21) Appl. No.: 14/848,107

(22) Filed: Sep. 8, 2015

(65) Prior Publication Data
US 2016/0067387 A1    Mar. 10, 2016

Related U.S. Application Data

(60) Provisional application No. 62/047,421, filed on Sep. 8, 2014.

(51) Int. Cl.
*A61L 31/08* (2006.01)
*C23C 16/40* (2006.01)
(Continued)

(52) U.S. Cl.
CPC ............. *A61L 31/088* (2013.01); *A61L 31/16* (2013.01); *C23C 16/0281* (2013.01);
(Continued)

(58) Field of Classification Search
None
See application file for complete search history.

(56) References Cited

U.S. PATENT DOCUMENTS 5,978,256 A * 11/1999 Sohn ...................... B82Y 10/00
257/315
5,980,973 A * 11/1999 Onyekaba ............. A61L 31/088
424/424

(Continued)

OTHER PUBLICATIONS

Brinkmann et al. "Electrical, optical and structural investigation of plasma-enhanced chemical vapor-deposited amorphous silicon oxynitride films of solar cell applications". Solar Energy Materials & Solar Cells, 108, Oct. 23, 2012, pp. 180-188.*

(Continued)

*Primary Examiner* — Carlos A Azpuru
*Assistant Examiner* — Casey S Hagopian
(74) *Attorney, Agent, or Firm* — Meunier Carlin & Curfman LLC

(57) ABSTRACT

Amorphous SiOx (SiO2), SiONx, silicon nitride (Si3N4), surface treatments are provided, on both metal (titanium) and non-metal surfaces. Amorphous silicon-film surface treatments are shown to enhance osteoblast and osteoblast progenitor cell bioactivity, including biomineral formation and osteogenic gene panel expression, as well as enhanced surface hydroxyapatite (HA) formation. A mineralized tissue interface is provided using the amorphous silicon-based surface treatments in the presence of osteoblasts, and provides improved bone cell generation/repair and improved interface for secure attachment/bonding to bone. Methods for providing PEVCD-based silicon overlays onto surfaces (Continued)

are provided. Methods of increasing antioxidant enzyme (e.g., superoxide dismutase) expression at a treated surface for enhanced healing are also provided. Continuous generation and release of Si4+ ion into an in vitro or in vivo environment in the presence of osteoblasts/osteoblast progenitor cells, methods of employing same for enhancing the rate of bone healing/bone regeneration, is also described.

18 Claims, 26 Drawing Sheets

(51) Int. Cl.
    *C23C 16/30*       (2006.01)
    *A61L 31/16*      (2006.01)
    *C23C 16/02*       (2006.01)

(52) U.S. Cl.
    CPC .......... *C23C 16/308* (2013.01); *C23C 16/401* (2013.01); *A61L 2300/102* (2013.01); *A61L 2300/412* (2013.01); *A61L 2400/18* (2013.01); *A61L 2420/02* (2013.01); *A61L 2430/02* (2013.01)

(56) References Cited

U.S. PATENT DOCUMENTS

| | | | | |
|---|---|---|---|---|
| 6,337,229 B1* | 1/2002 | Yamazaki | ........... | H01L 21/2022 438/149 |
| 6,900,067 B2 | 5/2005 | Kobayashi et al. | | |
| 2005/0084980 A1* | 4/2005 | Koo | ........... | G01J 3/44 436/171 |
| 2006/0127443 A1* | 6/2006 | Helmus | ........... | A61L 27/20 424/423 |
| 2008/0071382 A1* | 3/2008 | Kumar | ........... | A61L 27/04 623/23.57 |

OTHER PUBLICATIONS

Wan et al. "Si—N—O Films Synthesized by Plasma Immersion Ion Implantation and Deposition (PIII&D) for Blood-Contacting Biomedical Applications", IEEE Transactions of Plasma Science, vol. 34, No. 4, Aug. 2006, pp. 1160-1165.*
Wang et al. "Silicon nitride coating on titanium to enable titanium-ceramic bonding", Journal of Biomedical Materials Research, vol. 46, Issue 2, Aug. 1999, pp. 262-270.*
Barron, A. "Chemical vapor deposition of silica films", OpenStax-CNX module: m24897, Jan. 22, 2010, pp. 1-10. (Year: 2010).*
Brinkmann et al. "Electrical, optical and structural investigation of plasma-enhanced chemical vapor-deposited amorphous silicon oxynitride films of solar cell applications". Solar Energy Materials & Solar Cells, 108, Oct. 23, 2012, pp. 180-188. (Year: 2012).*
Wan et al. "Si—N—O Films Synthesized by Plasma Immersion Ion Implantation and Deposition (PIII&D) for Blood-Contacting Biomedical Applications", IEEE Transactions of Plasma Science, vol. 34, No. 4, Aug. 2006, pp. 1160-1165. (Year: 2006).*
Wang et al. "Silicon nitride coating on titanium to enable titanium-ceramic bonding", Journal of Biomedical Materials Research, vol. 46, Issue 2, Aug. 1999, pp. 262-270. (Year: 2010).*
D K Dhanwal, et al., "Epidemiology of hip facture: Worldwide geographic variation." Indian Journal of Orthopaedics, 45 (1): 15-22 (2011).
V G Varanasi, et al., "Si and Ca Individually and Combinatorially Target Enhanced MC3T3-E1 Subclone 4 Early Osteogenic Marker Expression" Journal of Oral Implantology, 38 (4): 325-336 (2012).
N S Tousi, et al., "Combinatorial effect of Si4+, Ca2+, and Mg2+ released from bioactive glasses on osteoblast osteocalcin expression and biomineralization." Materials Science & Engineering C-Materials for Biological Applications 33 (5): 2757-2765 (2013).

A Bachar, et al., "Effects of Addition of Nitrogen on Bioglass Properties and Structure." Journal of Non-Crystalline Solids, 358 (3): 693-701 (2012).
P Sepulveda, et al., "Characterization of Melt-Derived 45S5 and sol-gel-derived 58S Bioactive Glasses." Journal of Biomedical Materials Research, 58 (6) 734-740 (2001).
S. McAuley, et al., "Silicon micromachining using a high-density plasma source." Journal of Physics D: Applied physics, 34 (18), 2769 (2001).
H Nojiri, et al., Journal of bone and mineral research: the official journal of the America Society for Bone and Mineral Research, 26 (11): 2682-94 (2011).
J M Lean, et al., Journal of Clinical Investigation, 112 (6): 915-23 (2003).
F Jakob, et al., Methods Enzymol, 347: 168-79 (2002).
M. Iwai-Yoshida, et al., Journal of the mechanical behavior of biomedical materials, 13, 230-236 (2012).
M Arun et al., Toxicology Mechanisms and Methods, 21(7):561-6 (2011).
M F Ceiler, et al., Journal of the Electrochemical Society, 42 (6): 2067-2071 (1995).
V G Varanasi, et al., Journal of Biomedical Materials Research Part A, 98A (2): 177-184 (2011).
V G Varanasi, et aL, Acta Biomaterialia, 5 (9): 3536-3547 (2009).
L L Hench, Bioceramics, Journal of the American Ceramic Society, 81 (7): 1705-1728 (1998).
M H Lee, et al., Biochemical and Biophysical Research Communications, 309 (3): 689-694 (2003).
Y Choe, et al., Journal of Cellular Biochemistry, 113 (4): 1426-36 (2012).
W P Ho, et al., Journal of Cellular Biochemistry, 108 (5): 1084-93 (2009).
J E Kim, et al., Journal of Bone and Mineral Research, 24 (6): 1055-1065 (2009).
N Saito, et al., J Biomed Mater Res, 47 (1): 104-10 (1999).
E J Carragee, et al., Spine J, 11 (6): 471-91 (2011).
M Horie, et al., Inhalation toxicology, 24 (7): 391-400 (2012).
A Moshaverinia, et al., Journal of Materials Chemistry, 21 (5): 1319-1328 (2011).
X Lu, Y Leng, Journal of Biomedical Materials Research Part B-Applied Biomaterials, 90B (1): 438-445 (2009).
E Lamers, et al., Biomaterials, 31 (12): 3307-3316 (2010).
S Lenhert, et al., Biomaterials, 26 (5): 563-70 (2005).
L L Jiang, et al., Materials Science & Engineering C-Materials for Biological Applications, 32 (4): 742-748 (2012).
E Saiz, et al., Biomaterials, (23): 3749-3756 (2002).
L L Hench, Journal of the European Ceramic Society, 29(7): 1247-1265 (2009).
S Foppiano, et al., Acta Biomaterialia, 3 (5):765-771 (2007).
V G Varanasi, et al., Journal of the Electrochemical Society, 152 (1): C7-C14 (2005).
V. G. Varanasi, et al., Materials Science and Engineering a-Structural Materials Properties Microstructure and Processing, 528 (3): 978-985 (2011).
V G Varanasi, et al., Journal of Alloys and Compounds, 470 (1-2): 354-359.
V G Varanasi, et al. Thin Solid Films, 516 (18): 6133-6139 (2008).
V G Varanasi, et al., High Temperature Ceramic Matrix Composites, 5: 595-601 (2005). Abstract.
M Keskin, et al., Plastic and reconstructive surgery, 122 (2): 400-409 (2008).
V P Swarup et al., Metallomics, 3 (11): 1218-26 (2011).
L Du, et al., Talanta, 101 11-6 (2012).
G Z Xiao, et al., Journal of Bone and Mineral Research, 17(1) 101-110 (2002).
N Nabavi, et al., PloSone, 7 (9): 46265 (2012).
D Boonyawan, et al., Surface and Coatings Technology, 205, Supplement 2 (O): S552-S557 (2011).
C C Lin, et al., Biomaterials, 26 (17): 3655-62 (2005).
ME Pryor, et al., Journal of clinical periodontology, 32(9): 966-72 (2005).
G Shi, et al., Langmuir: the ACS journal of surfaces and colloids, 25 (17): 9639-43 (2009).

(56) References Cited

OTHER PUBLICATIONS

S Sarkar, et al., Biomaterials, 27 (27): 4775-4782 (2006).
Gallego, D.; Ferrell, N.; Sun, Y.; Hansford, D.J., 2008, "Multilayer micromolding of degradable polymer tissue engineering scaffolds." Materials Science and Engineering C 28, No. 3, 353-358.
M.-O. Montjovent, et al., Tissue engineering,11 (11-12), 1640-1649 (2005).
A. Sandukji, et al., Human & experimental toxicology, 30 (6), 435-42 (2011).
Canullo L., Dellavia C., Sinus lift using a nanocrystalline hydroxyapatite silica gel in severely resorbedmaxillae: histological preliminary study, Clinical implant dentistry and related research, 11 Suppl 1:e7-13 (2009).
M. Ceiler, et al., Journal of the Electrochemical Society, 142 (6), 2067-2071 (1995).
U. Diebold, The surface science of titaniumdioxide, Surface science reports, 48 (5), 53-229 (2003).
S. Lopez-Esteban, et al, Journal of the European Ceramic Society, 23 (15), 2921-2930 (2003).
J. Gomez-Vega, et al., Processing. Biomaterials, 21 (2), 105-111 (2000).
V. G. Varanasi, et al., Materials Science and Engineering, 528 (3), 978-985 (2011).
V. Varanasi, et al., Acta biomaterialia, 5 (9), 3536-3547 (2009).
V. G. Varanasi, et al., Thermodynamic analysis and growth of ZrO2 by chloride chemical vapor deposition, Thin Solid Films, 516 (18), 6133-6139 (2008).
Y. Liu, et al., Materials Science and Engineering, 489 (1), 294-301 (2008).
A. Bachar, et al., Journal of the mechanical behavior of biomedical materials, 23, 133-148 (2013).
J. Gomez-Vega, et al., Journal of biomedical materials research, 46 (4), 549-559 (1999).
H. Jeon, et al. A mini-review: Journal of Biomedical Materials Research Part B: Applied Biomaterials,102 (7), 1580-1594 (2014).
K. Seunarine, et al., A hierarchical response of cells to perpendicular micro- and nanometric textural cues NanoBioscience, IEEE Transactions, 8 (3), 219-225 (2009).
W. Asghar, et al., Nanotechnology, 23 (47), 475601 (2012).

T. Albrektsson, et al., The International journal of prosthodontics, 17 (5), 536-543 (2003).
A. S. Badami, et al., Biomaterials, 27 (4), 596-606 (2006).
T. Odatsu, et al., Journal of Biomedical Materials Research Part A (2015).
H. Demirkiran, et al., XANES analysis of calcium and sodium phosphates and silicates and hydroxyapatite-Bioglass 45S5 co-sintered bioceramics, Materials Science and Engineering, 31 (2), 134-143 (2011).
J. Rajendran, et al., XANES analysis of dried and calcined bones, Materials Science and Engineering, 2013, 33 (7), 3968-3979 (2013).
H. K. W. Kim, et al., Bone, 54, 141-150 (2013).
I. Notingher, et al., Journal of molecular structure, 744, 179-185 (2005).
G. Puppels, et al., Nature, 347,301-303 (1990).
F. Golightly, et al., The influence of yttrium additions on the oxide-scale adhesion to an iron-chromium-aluminum alloy, Oxidation of Metals, 10 (3), 163-187 (1976).
E. J. Szili, et al., Surface science, 602 (14), 2402-2411 (2008).
M. Domanski, R., et al., Nanotechnology 2012, 23 (6), 065306.
M. Burgos, et al., Journal of sol-gel science and technology, 16 (3), 267-276 (1999).
D. Dunn, et al., Journal of Applied Physics, 89 (5), 2635-2640 (2001).
Y. Wang, et al., The microstructure and its high-temperature annealing behaviours of a-Si:O:H film (2001). English Abstract included in text.
T. A. Jurgens, et al., The Journal of Physical Chemistry, 99 (2): 731-743 (1995).
M. L. Hitchman, et a., The Electrochemical Society interface, 10(2): 40-45 (2001).
J. Lee, H. et al., Journal of the American Ceramic Society, 86 (10): 1797-1799 (2003).
P. Habibovic, et al., Journal of the American Ceramic Society, 85 (3): 517-522 (2002).
M. Saito, et al., Osteoporosis international, 17 (7): 986-995 (2006).
M. Vila, et al., Journal of applied physics, 94 (12): 7868-7873 (2003).
H. Ehrlich, et al., Advanced Functional Materials, 21 (18): 3473-3481 (2011).

\* cited by examiner

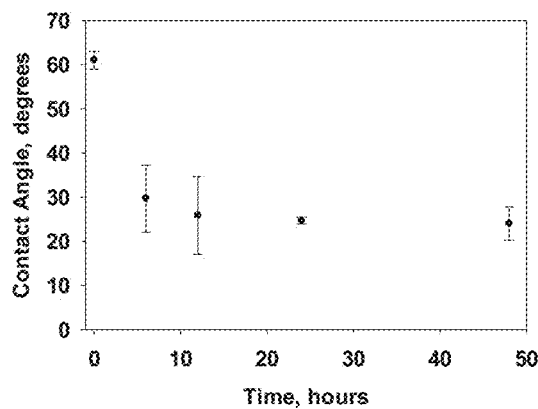
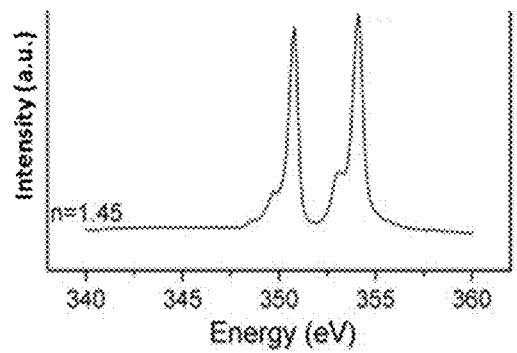
Fig. 2AFig. 2B
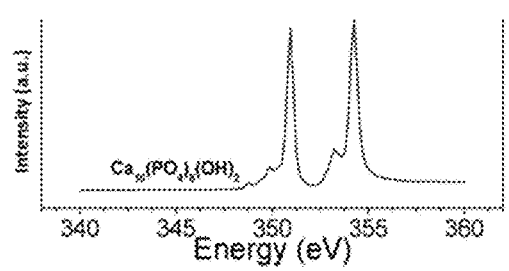
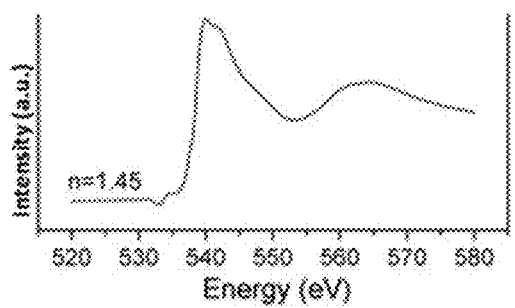
Fig. 2CFig. 2D
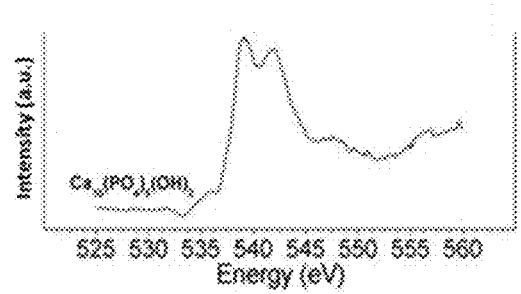
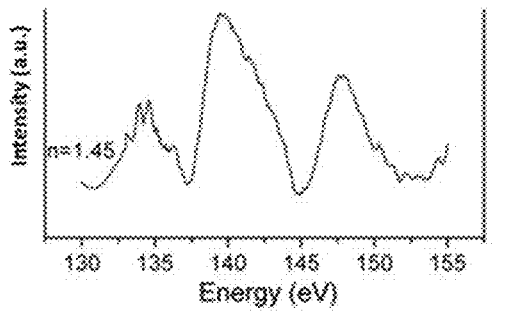
Fig. 2EFig. 2F
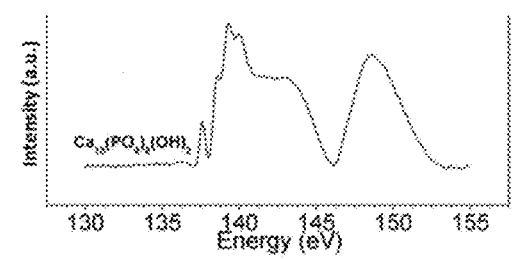
Fig. 2G Fig. 5A
Fig. 5C
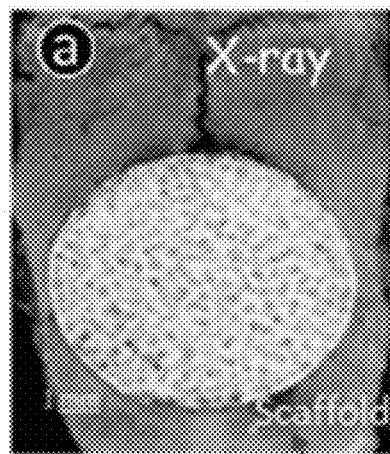
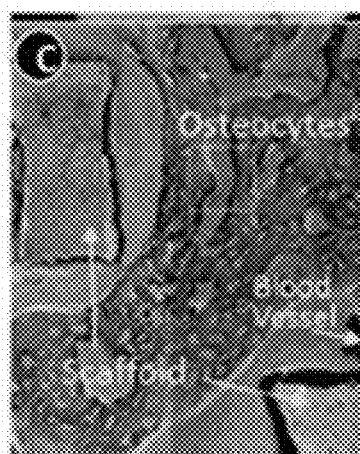
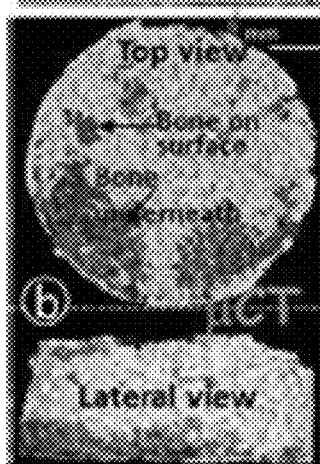
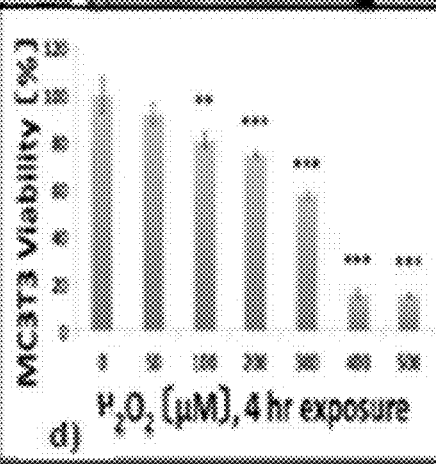
Fig. 5B
Fig. 5D

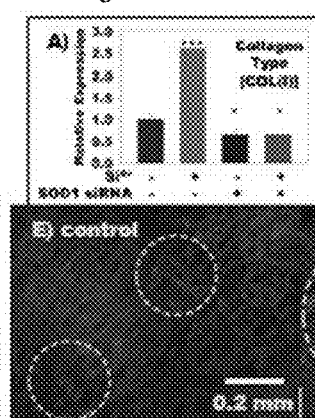 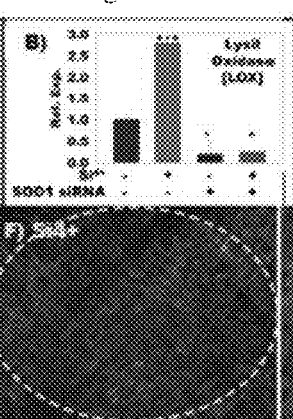 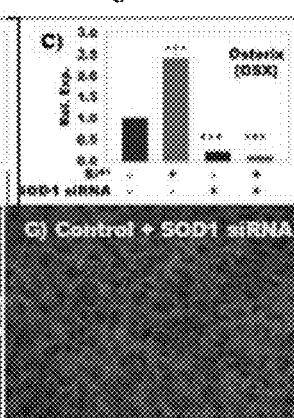 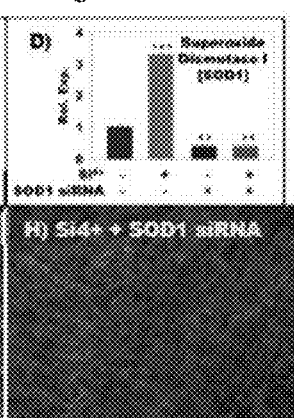
Fig. 6A   Fig. 6B   Fig. 6C   Fig. 6D
Fig. 6E   Fig. 6F   Fig. 6G   Fig. 6H Fig. 17A
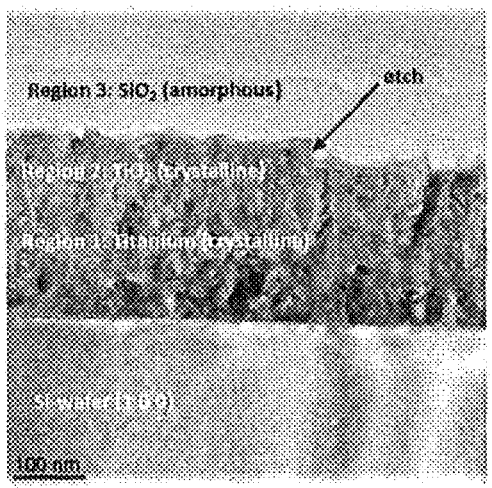
Fig. 17B
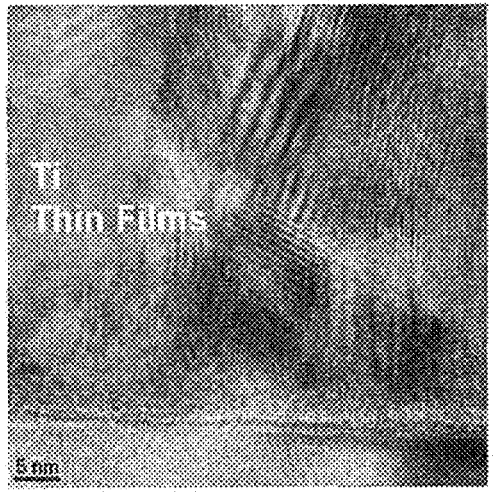
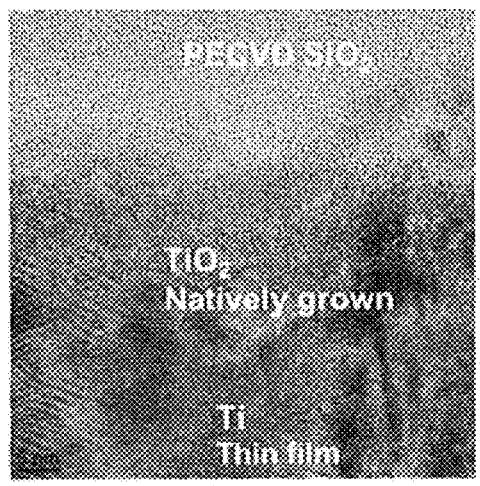
Fig. 17C
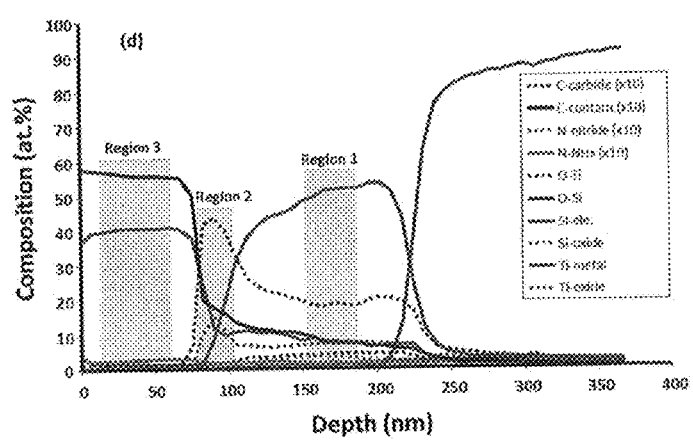
Fig. 17D

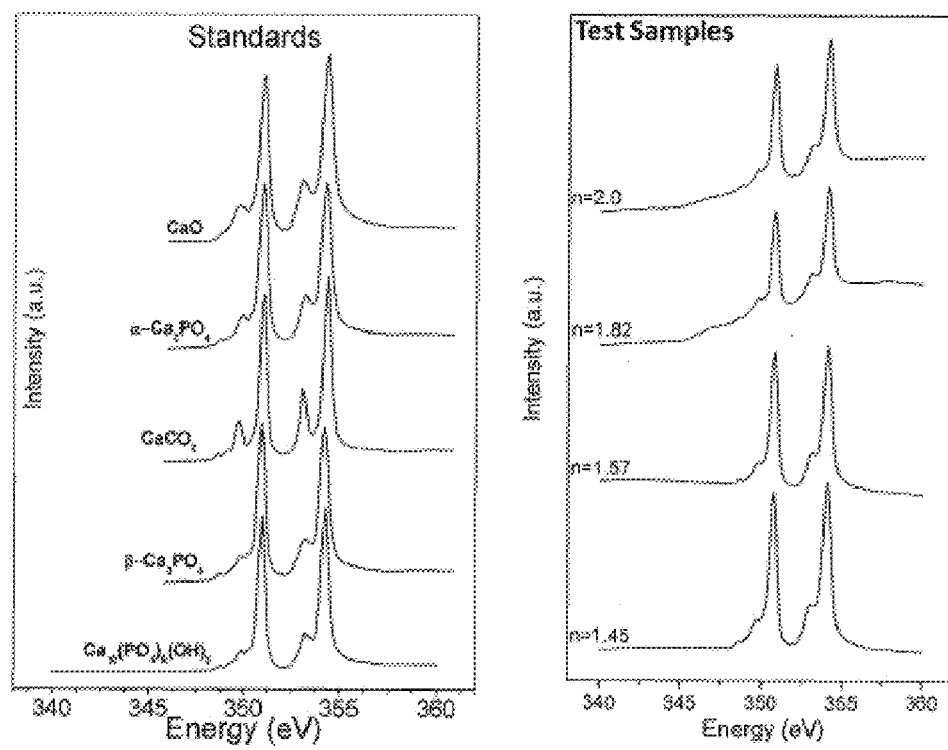
Fig. 19A(1)   Fig. 19A(2)
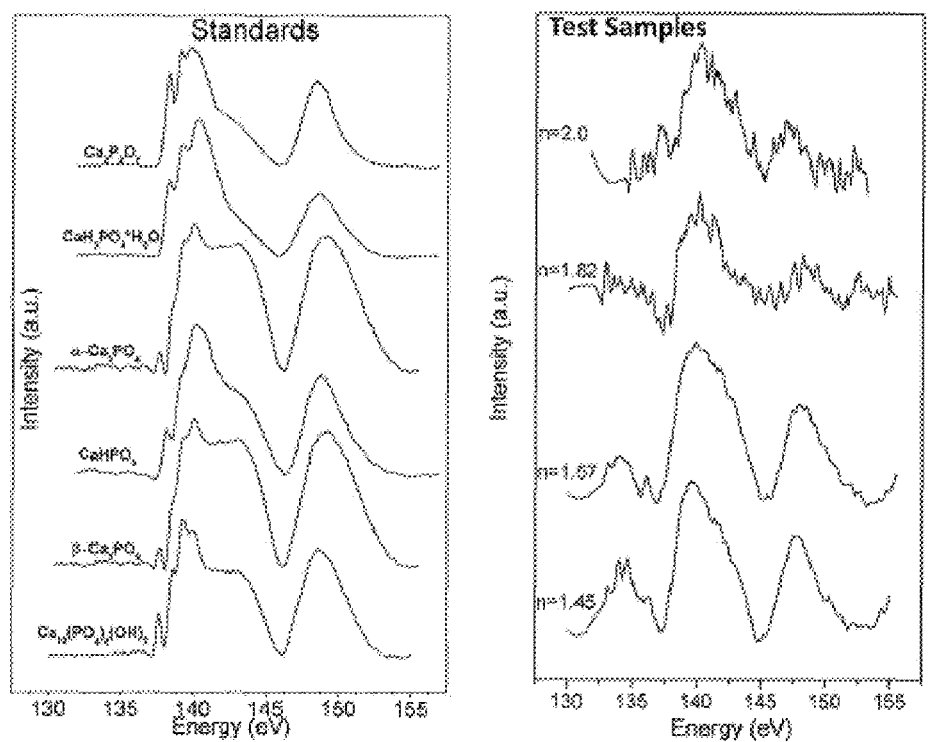
Fig. 19B(1)   Fig. 19B(2)

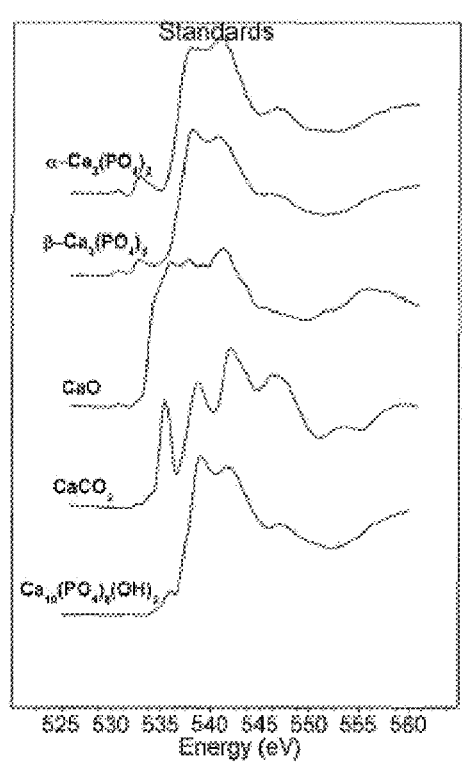
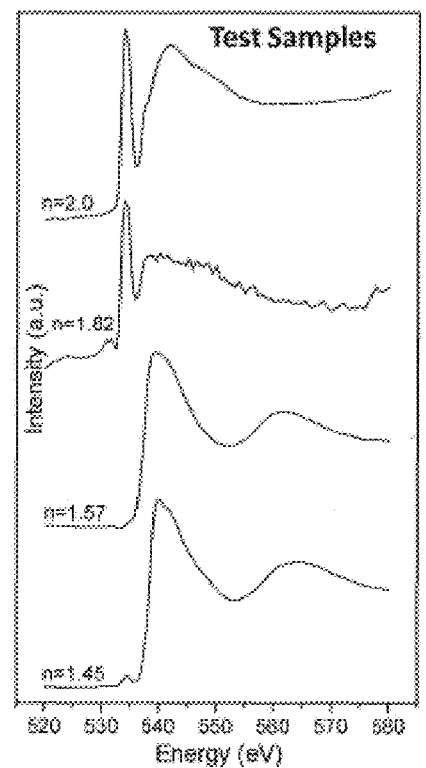
Fig. 19C(1)  Fig. 19C(2)

AMORPHOUS SILICON OXIDE, AMORPHOUS SILICON OXYNITRIDE, AND AMORPHOUS SILICON NITRIDE THIN FILMS AND USES THEREOF

CROSS-REFERENCE TO RELATED APPLICATIONS

The present application claims the benefit under 35 U.S.C. 119(e) of the filing date of U.S. Application Ser. No. 62/047,421, filed on Sep. 8, 2014. The entire contents of said application are specifically incorporated herein.

FEDERAL GRANT SUPPORT

The work was supported by a grant from National Institutes of Health (1R03DE023872-01A1) and Grant #24444100005, and CNMS #2010-080. The United States federal government owns rights in the present invention.

FIELD OF THE INVENTION

The present invention relates to the field of surface treatments and/or surface thin-film/nano coatings for medical devices, dental implants and semi-conductor, solar cell, and microelectronic devices. The invention also relates to methods for enhancing osteogenesis, bone generation (formation), fracture healing and wound healing. The invention also relates to the field of medical device surface design and chemical deposition methods.

BACKGROUND OF THE INVENTION

Bone fracture incidence from trauma, as well as age-related fragility and/or disorders, contribute to ~$8B in morbidity/mortality costs and ~800 k procedures annually. It is estimated that the incidence of these medical conditions will continue to rise, especially as life-expectancy increases [1-3].

When fractures occur, the site is structurally unstable and hypoxic due to severe bone loss and ischemia. Inflammation ensues after site re-vascularization, and oxygen metabolites accumulate as reactive oxygen species (ROS: O2-, H2O2). In these fractures, ROS levels can be as much as 8 times that of normal patient levels [4]. An increase in ROS levels has been reported to interrupt bone healing by causing osteoblast DNA damage, apoptosis, and down-regulation of osteogenic differentiation marker expression [5-7]. High ROS levels also create a condition known as oxidative stress. The combination of oxidative stress and site fracture instability leads to a delay in and/or improper bony union [4, 8-12]. Therefore, targeting the prevention and/or inhibition of high ROS levels and oxidative stress, while simultaneously providing structural support at a fracture/trauma site, is vital to ensuring and promoting proper bone healing.

ROS levels must be controlled in order to promote proper fracture healing. Elevated ROS levels may be controlled by increasing available antioxidant enzyme, such as the antioxidant enzyme, superoxide dismutase (SOD1) [13, 14]. SOD1 is also very important in stimulating the complex series of biochemical and physiological events needed for bone development and bone healing in vivo. Thus, it was envisioned by the present investigators that an increase in antioxidant enzyme expression would aid the bone healing process, and in particular, osteoprogenitor cell differentiation. It has been reported that without expression of SOD1, osteogenic transcription factors (e.g., osterix (OSX)) can potentially be down-regulated, and result in a reduction in bone strength [6]. However, methods and/or materials that provide for the effective and therapeutic control and/or prevention of destructive high ROS levels through enhancing the generation of anti-oxidants remain lacking in the medical arts.

Current structural materials used to support large missing bone volume do not provide a mechanism whereby deleteriously high levels of ROS can be controlled. Nor do the metal surfaces of these implants foster the formation of an apatite surface layer, an important aspect of the bone formation process. Thus, while metal implants (e.g., titanium [Ti]) are useful as structural materials for bone implant because of their strength, they suffer the disadvantage of long healing times [15].

Hydroxyapatite and calcium phosphate-based coatings have also been used with bone implants to foster surface bone attachment to the implant. However, while these materials do provide for the formation of a surface hydroxyapatite layer, they unfortunately fail to provide stable, strong bone attachment because of the large coefficient of thermal expansion mismatch with the underlying metal. This thermal expansion mismatch problem results in resorption and delamination of the bone from the metal surface of the implant, and ultimately failure of the implant attachment [16]. In addition, these coatings fail to provide a solution to the damaging effects of high ROS levels, so common to the physiological environment of an implant site in vivo.

Synthesis routes for synthetic hydroxyapatite overlay cause inhomogeneity in the coating and have thermal expansion mismatch with the underlying Ti, leading to delamination and instability of the coating [1]. Bioactive glass coatings, which are modified from commercially available bioglass with added MgO for improved thermal expansion matching, have shown a drawback to down-regulate important osteogenic markers associated with bone formation due to $Mg^{2+}$ release [2].

Attempts to strengthen the amorphous silica network have involved the addition of nitrogen (N) as a constituent to the SiOx network. The addition of N changes the tetrahedrally coordinated network into one that is a combination of tetrahedral and trigonal [13]. Incorporation of N (through annealing with $N_2$ gas) into the amorphous silica-based bioactive glass matrix improved its mechanical strength [14]. This also strengthened amorphous silica-based bioactive glass-Ti interface. However these coating are limited in that they can only be applied by enameling, which has a large coating to interface thickness ratio (1000:1), leaving them more susceptible to delamination [15]. Sputter coated silicon oxynitride films have also been studied for their mechanical properties and showed a linearly increasing strength with N content [13]. Beyond its effect on SiOx mechanical strength, the effect of adding N on biomineralization and cells' response to Si(ON)x surfaces are still unknown. Bio-inspired surface topographies at nano and micrometer scales are known to influence cellular behaviors such as cell adhesion, migration, differentiation and growth [16-19], with moderately rough surfaces (1-2 μm) showing stronger bone responses than smoother or rougher surfaces [19]. Oral implants also have moderately rough surfaces that permit bone ingrowth into minor surface irregularities, promoting osseointegration [19] while a bioactive coating can add biochemical bonding with biomechanical bonding of these oral implants.

Despite these and other approaches to addressing the complicated problems associated with successful bone healing, a need continues to exist in the medical arts for controlling harmfully high ROS levels at an implantation site, while simultaneously providing clinically acceptable strong and stable structural bone support. Thus, a great clinical need continues to exist in the medical arts for improved techniques and materials for achieving more stable and enhanced bone-to-device adhesion, bone-to-bone healing, and more rapid bone formation and/or regeneration and repair.

SUMMARY OF THE INVENTION

The present invention provides a solution to the above and other medical and/or clinical needs.

Devices:

In a general and overall sense, the present invention provides devices, such as orthopedic and dental medical implant devices, or a component piece of a device or tool, that includes at least one treated surface having enhanced bioactive and/or enhanced bio-osteogenic characteristic, such as an enhanced bone regeneration and/or bone formation promoting activity. The treated surface comprises an amorphous silicon oxide (SiOx, such as SiO2), amorphous silicon nitride (SiNx, such as Si3N4), and/or nitrogen enriched silicon oxide (SiONx) thin film and/or nanolayer thereon. The nitrogen containing silicon oxide, in some embodiments, is defined by the formula Si(ON)x, where nitrogen incorporation occurs as a substitution for oxygen. More complicated chemistries for providing amorphous treatments typical of conventional chemistries (they relate to oxygen and nitrogen content), are simplified employing the approach described in the present invention. The more simplified chemistries for providing amorphous surface treatments of the present invention render the present materials preferable over conventional chemistries for providing a silicon-based surface treatment.

In some embodiments, a device having a treated surface comprising an amorphous silicon oxide (SiOx), amorphous silicon oxynitride (SiONx) or amorphous silicon nitride (SiNx) thin film and/or nanofilm is provided. By way of example, an amorphous SiOx may comprise SiO2. An amorphous SiNx may comprise Si3N4.

In some embodiments, a device comprising at least one treated surface having a thin film comprising an amorphous silicon oxide (SiOx), amorphous silicon nitride (SiNx), or amorphous nitrogen enriched silicon oxide (SiONx) is provided. The thin film is provided onto the surface with a PECVD process and a silicon based reagent comprising SiH4 or TEOS, and wherein the silicon based reagent reacts with (a) oxygen (O2) and/or nitrous oxide (N2O) to form SiOx, (b) nitrogen (N2) and/or ammonia (NH3) to form SiN4, or (c) oxygen (O2 or N2)) and nitrogen (N2 or NH3) to form SiONx. In some embodiments, the device surface will include a series of etched nanogrooves thereon. The amorphous silicon nitride (SiNx) may comprise Si3N4, while the amorphous silicon oxide SiOx may comprise SiO2.

Amorphous materials pertain to solid phase materials that exhibit no crystalline textures, have no grain structures, and exhibit long-range ordering within their structure.

Crystalline materials pertain to solid phase materials that exhibit texture, have grain structures, and exhibit short range ordering between adjoining atoms.

In some embodiments, the treated surface may be a metal surface (Ti, Co—Cr, Ni—Cr, stainless steel, cpTi, Ti6AL4V, Cr), or surface made of a composite material (e.g., a biopolymer) suitable for providing an amorphous SiOx (such as SiO2), amorphous silicon oxynitride (SiONx), and/or amorphous silicon nitride (SiNx, such as Si3N4) film thereon. In some embodiments, the treated surface is suitable for providing structural support for use in a tissue or bone. Alternatively, the surface may be suitable for use in a microelectronics device. Composite materials include biopolymer-bioceramic composites such as polylactic acid-hydroxyapatite bone defect fillers.

The Si—O—N solid phase elemental system is described by 2 models. For high O, low N containing systems, the formula describing Si—O—N is SizOxNy in which the entire solid system consists of a tetrahedral atom coordination structure in which N substitutes for O in the Si—O tetrahedran For low O, high N elemental system, the structure of the solid phase can be described by a random mixing model. This model described the mixing of Si—Si, Si—O, and Si—N structures in which both 3-fold and 4-fold coordinated Si atoms are bound to Si or O and N, respectively. The mixture can be represented by the formula (Si—Si)z (Si—O)x (Si—N)y. This is not a bonding model, rather, a mixing model of bonded structures.

The table below described compositions studied in this elemental system and has been theoretically calculated as well as demonstrated by the inventors.

These results were unexpected and surprising. These results were obtained from Canadian Light Source research data using x-ray absorbance near edge structure analysis.

The residual stress of the PECVD-based coating varies with the film composition structure, deposition temperature, RF power, pressure and the nature of the substrate [3]. The coefficients of thermal expansion for Ti metal and TiO$_2$ are nearly $8 \times 10^{-6} \times °$ C.$^{-1}$ and $9.5 \times 10^{-6} \times °$ C.$^{-1}$ respectively [4, 5] whereas SiO$_2$ on Ti based implants may have thermal expansion coefficient in the range of $8\text{-}15 \times 10^{-6} \times °$ C.$^{-1}$ depending upon the composition of the SiO$_2$ layer [6, 7]. Low temperature PECVD process alleviates the issues caused by the lattice constant and thermal expansion coefficient mismatch [8]. Moreover, this low temperature deposition eliminates the need for added constituents (e.g., MgO) to accommodate for thermal expansion mismatch [9-12].

Understanding of apatite formation in-vitro for bioactive silica-based materials and their dissolution has concentrated on bioactive glasses. Bioactive glasses undergo rapid ion exchange of alkali and alkaline earth metal cations with liquid protons to infiltrate the silica network. After this has occurred, surface silanols (evident by Si—OH Raman bond stretch) are available for dissolution, polymerization, and re-precipitation to form a silica gel network, which leads to apatite formation. Whereas PECVD-based silica forms surface silanols readily [20], skipping the rapid ion exchange step. Low temperature PECVD provides even more silanols on the oxide surface [3], resulting in apatite formation within 6 hours of in-vitro submersion. Cell culture testing showed the presence of collagen on all materials including control surfaces, however, Si(ON)x surfaces maximally enhanced periosteal cell osteogenic gene expression and stimulated added production of carbonate apatite biomineral matrix. Therefore, these overlays support the hypothesis that they can provide structural support by exhibiting strong adhesion to the underlying Ti/TiO$_2$ layers and stimulate the rapid formation of bone-like biomineral formation.

In another aspect, a method for enhancing the expression of superoxide dismutase I (SOD1) gene by osteoblasts is presented. In some embodiments, the method comprises exposing cells comprising osteoblasts or osteoblast progenitor cells to Si$^{4+}$ ions. In some embodiments, the method comprises providing a treated surface comprising an amorphous silicon oxide (SiOx), amorphous silicon oxynitride (SiONx) or silicon nitride (SiNx) thin film, and exposing a population of cells comprising osteoblasts or osteoblast progenitor cells to the treated surface in an aqueous environment comprising an osteogenic media, and enhancing SOD1 gene expression by the osteoblasts. In the aqueous environment, Si4+ ions are released into the aqueous environment, and the free Si4+ ions enhance SOD1 gene expression by osteoblasts, compared to SOD1 gene expression levels produced by osteoblasts in the absence of Si4+ ion.

The SOD1 gene expression enhancing effect observed in the presence of Si4+ was unexpected and surprising, and provided a solution to controlling against the harmful effects of high reactive oxygen species (ROS) levels typical at device implantation sites. Thus, a method for reducing levels of reactive oxygen species (ROS) in an aqueous in vitro and/or in vivo environment is also provided. In some embodiments, the method comprises increasing SOD1 expression levels by exposing a cell population comprising osteoblasts to Si4+ ion, and reducing ROS levels, wherein SOD1 acts to reduce ROS levels.

A method for increasing osterix (OSX) gene expression by a population of cells comprising osteoblasts in vitro and/or in vivo is also provided. In some embodiments, the method comprises increasing SOD1 expression levels by exposing a cell population comprising osteoblasts or osteoblast progenitor cells to Si4+ ion, and increasing osterix (OSX) gene expression, wherein increased expression of SOD1 enhances osterix (OSX) gene expression in a population of cells comprising osteoblasts or osteoblast progenitor cells. OSX is an important transcription factor required for osteoblastic differentiation, and therefore increasing expression levels of OSX also provides a method for enhancing osteoblastic cell differentiation. More specifically, OSX acts to stimulate the expression of OCN (osteocalcin), a protein that links the organic and mineral component of bone matrix. Collagen 1 (COL)1)) gene expression is also enhanced by OSX, and results in the synthesis of Collagen 1, the organic (non-mineral) component of bone. Collagen 1 is a very dense material that forms dense cross-linked ropes which functions to give bone its tensile strength, and keeping it from pulling apart. The expression of the OCN and COL1 genes results in the formation of the collagen matrix.

SOD1 expression also acts to stimulate expression of LOX (Lysyl oxidase), an extracellular copper enzyme that catalyzes formation of aldehydes from lysine residues in collagen and elastin. These aldehydes are highly reactive, and undergo spontaneous chemical reactions with other lysyl oxidase-derived aldehyde residues, or with unmodified lysine residues, which results in the crosslinking of collagen and elastin, and the formation of a bone matrix of high density and strength. The bone matrix is then "mineralized" by deposition of a calcium-phosphate-hydroxide salt, called hydroxyapatite. Hydroxyapatite formation is also enhanced at an Si(ON)x treated surface by facilitating H+ ingress into the matrix from the in vitro/in vivo environment, loosening and releasing silanol or Si4+ groups from the Si(ON)x matrix, and rendering remnant surface sites available for the nucleation of small crystals of hydroxyapatite. This process can occur without the presence of cells initially. However, for sustained growth of carbonated or non-carbonated hydroxyapatite, osteoblasts must be present for this to become integrated into biomineral. Thus, providing a method whereby Si4+ ion may be continuously released from a treated surface, such as a Si(ON)x treated surface of an implant device, results in a rapid formation of a composite mineralized tissue material at the implant surface, providing a secure and strong attachment site at the implantable device-bone interface.

Providing a constant source of free ions into the environment, such as Si4+, functions to provide an effective method for improving bone healing rates and increasing the quality and stability of bone attachment. Selection of a particular amorphous material, such as silicon oxide SiOx), amorphous silicon oxynitride (SiONx) or silicon nitride (SiNx) thin film, can be selected as a surface treatment, so as to achieve a desired mineralized matrix layer at a device surface/bone interface.

In some embodiments, a method for enhancing bone attachment, bone healing and/or bone formation and/or bone regeneration, is provided. In some embodiments, the method comprises providing a treated surface comprising an amorphous silicon oxide (SiOx), amorphous silicon oxynitride (SiONx) or amorphous silicon nitride (SiN) thin film (nanofilm) on at least one surface of an implantable medical device, placing the treated surface in an aqueous environment in the presence of a population of cells comprising osteoblasts or osteoblast progenitor cells, forming a hydroxyapatite layer on the surface to provide a mineralized tissue, and attaching a bone surface to the mineralized tissue to provide a bone-mineralized tissue interface, wherein bone attachment to the device is enhanced. As used in the description of the invention, an enhanced bone attachment is described as a more rapid and stable attachment of a bone to a treated surface of a device, such as a bone implant (dental, orthopedic, etc.), as compared to the rate and strength of attachment of a bone to a surface that is not treated according to the present invention.

In yet another aspect, the invention provides a method for enhancing the rate of bone healing and/or bone regeneration at a treated surface of an implantable medical device in vivo, wherein at least one surface of the implant is a treated surface having an amorphous SiOx (such as SiO2), Si(ON)x, and/or amorphous silicon nitride (such as Si3N4) film and/or nanofilm thereon. The treated surface may further comprise a series of nano-ridges.

In another aspect, a method for preparing a treated surface comprising an amorphous silica, amorphous silicon nitride, or amorphous silicon oxynitride is provided. The amorphous silicon oxynitride film may be deposited onto a surface using a plasma-enhanced chemical vapor deposition (PECVD) technique. Plasma-enhanced chemical vapor deposition is a method that controllably delivers gas phase reagents into a laminar flow reaction chamber to deposit solid thin films onto a substrate. The PECVD method allows for the deposition of both amorphous and crystalline materials onto metal substrates, such as Ti implants. Besides amorphous coating deposition onto Ti surfaces, the present invention provides for treated surfaces that include etched features. The etched features are created by a process comprising a nano-scale lithographic method and/or a reactive ion etch method to provide nano-scale features of programmable dimensions onto a surface. In this manner, surface feature dimensions, as well as coating chemistry, may be optimized for enhanced and stable formation of bone at a bone-implant surface juncture.

Thin Films:

Thin films generally describe solid phase films of material that are coated onto a substrate of any type of material at an overall thickness less than 1000 nm In other embodiments, the thin film may be further described as a nanolayer thin film having a thickness of about 100 nm to about 1000 nm. In other particular embodiments, the treated surface may be further described as comprising a series of nano-microgrooves, onto which a silica and/or silicon oxynitride thin film may be deposited.

The thin films may also be prepared on a surface of a device in multiple or stacked layers of the silicon-based thin films. A device having a surface comprising multiple or stacked layers of silicon-based thin films, wherein said thin films are deposited by a PECVD deposition process to provide a SiOx, SiNx, SiONx, or combination thereof thin film to the surface. For example, the stacked or multiple layer configuration may be provided at the surface of a semi-conductor, solar cell or micro-electronics device Medical Devices:

Medical Devices are generally described as devices used in applications of medicine where their use assists patients in healing their structural or physiological functions.

Medical devices, particularly implantable medical devices, that include a treated surface, may be a dental implant or a bone implant. In these medical devices, it is envisioned that a treated surface will be at least one or more surfaces of the medical device that will be in contact with a cellular environment comprising osteoblasts, such as a surface of a dental implant, bone implant, or other medical device to be inserted into an animal or human to provide structural or other physiological support and/or to promote healing. In some embodiments, the dental implant is treated to include at least one surface, such as a surface that is in contact with dental tissue (bone and/or gum tissue), the treated surface comprising an amorphous silicon oxide (SiOx), amorphous silicon oxynitride (SiONx) or amorphous silicon nitride (SiONx) thin film and/or nanolayer thereon. In other embodiments, a bone implant is provided that includes at least one treated surface, the treated surface being a surface of the device that is anticipated to come in contact with a cellular environment comprising osteoblasts, such as a surface of bone fracture in an animal.

The implant may be fabricated from any material clinically suitable for use in a dental implant or medical device appliance, such as a glass, ceramic, metal, biopolymeric material (e.g., poly-lactic acid, polycaprilactone, polydimethlysulfoxide, a metallic nano-matrix implant material See US Pub 20140228972), or other biologically compatible and biologically inert, nontoxic material, known to those of skill in the medical device arts.

SiOx (SiO2), Si(ON)x, SiNx (Si3N4) Chemical Deposition Method:

In another aspect, an SiO2, Si3N4, and/or Si(ON)x film deposition chemistry for providing an amorphous silica-based nitrogen containing film and/or nanofilm onto a desired surface is provided. In particular embodiments, the amorphous silicon containing films/nanofilms may be deposited onto a surface using a method of plasma enhanced chemical vapor deposition (PECVD). Using this method, a silicon containing film may be deposited by a PECVD method to provide a SiOx, SiNOx and/or SiNx film, particularly a nano-film overlay onto a desired surface. In some embodiments, the SiOx is SiO2.

In some embodiments, the Si(O)x (such as SiO2) deposition chemistry comprises a method of forming a selected and/or preferred mineral and/or mineralized tissue at a surface, such as at a surface of a medical implant device, by using a defined reagent having a nitrogen/oxygen ratio that promotes the formation of a particular desired mineral/s and/or mineralized tissue. For example, and in some embodiments, the method provides for the selective formation of a mineral and/or mineralized tissue on a surface comprising $CaCO_3$, comprising treating a surface with Si(ON)x to provide a treated surface, placing the treated surface in an environment suitable to permit Si4+ release and hydroxyapatite formation on the surface, and forming a mineralized tissue comprising $CaCO_3$ on said surface. Therefore, as nitrogen incorporation increases in the amorphous silica surface composition, so too does the calcium carbonate get incorporated into the hydroxyapatite structure. This was unexpected. In the PECVD methodology, the incorporation of nitrogen into the films is controlled via gas phase oxygen to nitrogen levels. For example, to make amorphous silica, no nitrogen is incorporated in the gas phase. For Si(ON)x formation, equal parts oxygen and nitrogen are incorporated into the gas phase.

An exemplary chemical deposition method where the thin film is Si3N4. It is prepared as given under the reagent conditions in Table 2, however, the source of oxygen is removed to create the Si3N4 thin film.

Methods of Enhancing Bone Regeneration, Bone Formation, Wound Healing, Osteoprogenitor Cell Differentiation and Antioxidant Enzyme Expression:

In yet another aspect, a method for enhancing bone attachment and formation at a bone-implant surface interface is provided, comprising depositing on a surface to which bone attachment is desired an amorphous silicon oxynitride thin film and/or nanolayer to provide a treated surface that releases Si4+ in an in vitro or in vivo environment comprising a population of cells comprising osteoblasts or osteoblast progenitor cells, exposing the treated surface to a population of cells comprising osteoblasts, and enhancing osteoblast expression of a superoxide dismutase (SOD1) gene, forming hydroxyapatite on said treated surface, and forming a mineralized tissue with said hydroxyapatite on said surface to provide a bone-surface interface, and enhancing bone attachment and formation at said bone-surface interface.

In some embodiments, the amorphous SiOx (such as SiO2), amorphous SiNx (such as Si3N4), and/or amorphous Si(ON)x film and/or nano-layer may be deposited onto a surface using a PECVD (Plasma Enhanced Chemical Vapor Deposition) method and/or technique.

In yet another embodiment, a method for enhancing wound healing at an implant device site is provided. In some embodiments, the method comprises providing an amorphous silicon oxynitride film and/or nanofilm onto a surface of the device so as to provide a treated surface, and exposing the treated surface to an in vitro or in vivo environment comprising a population of cells comprising osteoblasts, wherein Si4+ ion is released; and enhancing wound healing at the site of the device implant, compared to wound healing at a device implant site in the absence of Si4+.

In another aspect, the invention provides a method for enhancing osteoprogenitor cell differentiation. In some embodiments, the method comprises depositing an amorphous SiOx (such as SiO2), amorphous SiONx (such as Si3N4), and/or amorphous Si(ON)x film and/or nano-film to a surface to provide a treated surface, and exposing the treated surface to an in vitro or in vivo environment comprising a population of cells comprising osteoblasts, wherein Si4+ ion is released in said aqueous in vitro or in vivo environment, and enhancing osteoprogenitor cell differentiation, wherein osteoprogenitor cell differentiation is enhanced in the presence of Si4+ compared to osteoprogenitor cell differentiation in the absence of Si4+. In particular embodiments, the treated surface includes an amorphous Si(ON)x thin film, or more particularly, an Si(ON)x nanofilm, wherein the treated surface is an etched surface containing a series of nano-grooves.

All of the treated surfaces described herein may further comprise a series of nano-groves. The amorphous SiO2, Si3N4, and/or Si(ON)x film and/or nanofilm may be deposited thereupon.

In yet another aspect, a method for upregulating expression of osteogenic transcription factors is provided. These osteogenic transcription factors comprise osterix (OSX), for example. A method for upregulating bone related markers, such as osteocalcin and core-binding factor a, is also provided using the silica-based films and/or nanofilms Upregulation of osteogenic transcription factors and bone related markers may be provided comprising providing a treated surface having a Si(ON)x thin film and/or nanofilm, and exposing said surface to an in vitro or in vivo environment comprising osteoblasts, wherein Si4+ ion is released, and upregulated osteogenic transcription factors, wherein osteoblast differentiation to osteocytes (bone cells) is enhanced in the presence of Si4+ compared to osteoblast differentiation in the absence of Si4+.

While not intending to be limited to any particular mechanism of action, it is envisioned that bone cell attachment is enhanced to a treated surface having an amorphous silicon oxynitride (Si(ON)x), SiO2, and/or Si3N4 thin film thereon by enhancing and/or inducing the more rapid formation of hydroxyapatite (HA) onto the treated surface, thus facilitating the formation of a mineralized tissue on the treated surface. The thus formed mineralized tissue provides for the secure attachment of bone to the treated surface, and eventually, the formation of secure bone-to-bone attachment as the thin film material degrades.

The natural degradation of a SiO2, Si3N4, and/or Si(ON)x-based film and/or nanofilm at a surface results in the release of ionic silicon (such as $Si^{4+}$). Increasing the availability of free ion, such as ionic silicon, at the site of, for example, a bone implant and/or dental implant, facilitates more rapid healing and bone attachment, at least in part, by reducing levels of reactive oxygen species (ROS:$O_2^-$, $H_2O_2$) in an in vitro or in vivo environment comprising osteoblasts, among other things. The formation of a mineralized tissue on the treated surface results, thus providing a site of attachment for bone, and a more secure bone-device connection that promotes healing and bone formation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF THE SEVERAL VIEWS OF THE DRAWINGS

In figures below, SiOx refers to SiO2 and SiNx refers to Si3N4.

FIG. 1 C. XANES analysis of O K-edge on Si(O)x surface, indicating no presence of hydroxyapatite (Ca and P peaks also not observed).

FIG. 2A is contact angle testing. Cell-free in vitro studies of amorphous Si(O)x, specifically SiO2. Presence of Ca, P, and O coordination on the surface of Si(O)x indicates the presence of HA (hydroxyapatite) and other phosphates. Contact angle is shown to rapidly decrease with increasing dissolution time. The rate of contact angle changes as a function of dissolution time is demonstrated to be proportional to 1/t ½, (R2=0.966). FIG. 2B. is the corresponding spectra for an in vitro sample with a refractive index of 1.45 after 6 hours, FIG. 2C is the Ca L2, 3 edge XANES spectra for HA (hydroxyapatite). FIG. 2D is the O K-edge spectra from the same sample where the Ca L2,3 edge was acquired, and confirms the coordination of oxygen in the structure. FIG. 2E is the corresponding spectra from HA (hydroxyapatite). FIG. 2F shows the corresponding P L-edge spectra of the in vitro sample. FIG. 2G shows the corresponding P L-edge spectra for HA (hydroxyapatite).

FIG. 5A shows that a Ca—P scaffold provided limited aid in supporting rat skull repair. The scaffolds were implanted into rat skills after 4 weeks 3-D uCT. FIG. 5B shows evidence of surface mineral formation (top view/lateral view) with no mineral ingress. FIG. 5C uses acid etching SEM to reveal a gap between the scaffold and osteocytes, osteoid and blood vessels in a newly formed bone region. FIG. 5D shows that elevated ROS reduces MC3T3 viability. These results demonstrate the use of novel materials and designs for accelerating bone formation and attachment.

FIG. 6A demonstrates Collagen I gene expression by osteoblasts is enhanced by $Si^{4+}$ (0.1 mM.) on ECM, compared to control (ECM without $Si^{4+}$). FIG. 6B demonstrates lysil oxidase (LOX) gene expression is enhanced by $Si^{4+}$ (0.1 mM) on ECM, compared to control (ECM without $Si^{4+}$). FIG. 6C demonstrates osteix (OSX) gene expression is enhanced by $Si^{4+}$ (0.1 mM.) on ECM, compared to control (ECM without $Si^{4+}$). FIG. 6D demonstrates superoxide dismutase (SOD1) gene expression is enhanced by $Si^{4+}$ (0.1 mM.) on ECM, compared to control (ECM without $Si^{4+}$). FIG. 6E shows that early WT (MC3T3-E1) osteogenesis is enhanced by $Si^{4+}$. FIG. 6F demonstrates that $Si^{4+}$ (0.1 mM) enhanced collagen matrix formation (dense, Picrosirius red stained tissue with yellow-orange elongated collagen fibers) vs. Control. FIG. 6G shows that SOD1 siRNA inhibits collagen matrix formation even in the presence of $Si^{4+}$, compared to Control (no $Si^{4+}$, no SOD1 siRNA, 50 ppm ascorbic acid (Vitamin C)). FIG. 6H shows SOD1 siRNA also knocked down collagen matrix formation, even in the presence of Si+, compared to Control. (Anova, *p<0.05, p<0.01, *p<0.001). These data demonstrate that $Si^{4+}$ enhances osteoblast gene expression and collagen matrix synthesis via SOD1 enhancement.

FIG. 17A-FIG. 17F. Characterization of nanofabricated devices TEM micrographs. FIG. 17A-FIG. 17C show lateral view of overlaid thin films. (FIG. 17A) The overall device consists of PECVD SiOx layer (region 3) deposited onto a natively grown $TiO_2$ layer (region 2), which was grown on an EB-PVD Ti layer (region 1). TEM micrograph at higher magnification shows (FIG. 17B) nano-structural features of EB-PVD Ti film and (FIG. 17C) adequate miscibility/adhesion between Ti—$TiO_2$—SiOx interfacial layers (FIG. 17D) X-ray Photoelectron Spectroscopy (XPS) analysis of through-thickness XPS data shows steadily diffused and chemically bonded interface composition whereas (FIG. 17E) surface XPS data reveals surface elemental composition of nanofabricated PECVD layers. (FIG. 17F) Nano-scratch data exhibits no change in resistance with increasing vertical load that confirmed strong interfacial adhesion of SiOx overlays with the underlying Ti—TiO2 substrate. The inset shows the electron micrograph of the surface after the incremental load (0-5000 μN) scratch test was done. The max depth of the scratch was 178 nm.

FIG. 19A(1), FIG. 19A(2), FIG. 19B(1), FIG. 19(B)2, FIG. 19C(1) and FIG. 19C(2). X-ray absorbance near edge structure (XANES) spectroscopy Comparative data for (L) Standards and (R) PECVD-based SiOx (n=1.45), Si(ON)x (n=1.57, n=1.82), and SiNx (n=2.0) where "n" represents the initial refractive index for the characteristic surface. Test Samples were investigated after 6 hours of in vitro immersion to examine the presence of calcium (FIG. 19A(1) Standards, FIG. 19A(2) Test Samples) Phosphorous (FIG. 19B(1) Standards, FIG. 19B(2) Test Samples) and Oxygen (FIG. 19C(1) Standards, FIG. 19C(2) Test Samples) on the surface of each sample. The data analysis reveals the formation of hydroxycarbonate apatite with higher carbonate to phosphate ratio as the N/O ratio increases in the overlay.

FIG. 23A illustrates multilayered bioactive glass coatings on Ti/TI-Ox surfaces; FIG. 23A illustrates a zoom-in.

DETAILED DESCRIPTION OF THE INVENTION

Figure 1A:
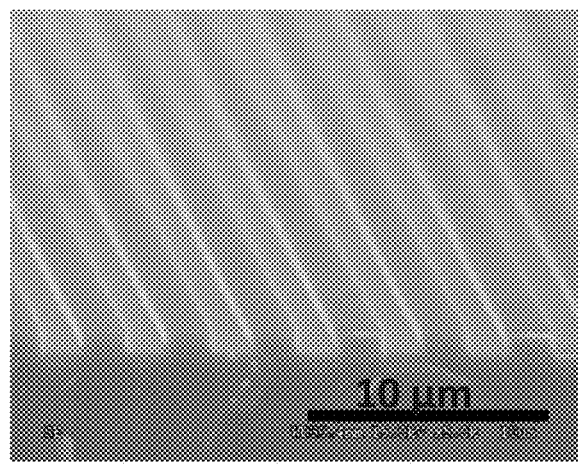
FIG. 1 A. Amorphous Si(O)x, specifically SiO2, coating on a fabricated Si-wafer showing a nano-/micro-grooved etch pattern. The PECVD Si(O)x coating on the Si wafers had a 100 nm trench depth and 2 μm trench width.
FIG. 1B. Raman spectroscopy indicated the presence of the underlying wafer and an initial hydroxylated silanol layer (950-1000 cm$^{-1}$, SiOH) after the PECVD process completes, prior to in vitro studies (probably owed to humidity exposure prior to scan).
FIG. 1D. XANES analysis of a hydroxyapatite (HA) standard.

While preferred embodiments have been shown and described herein, it will be apparent to those skilled in the art that such embodiments are provided by way of example only. Numerous variations, changes, and substitutions will now occur to those skilled in the art without departing from the spirit of the disclosure. It should be understood that various alternatives to the embodiments described herein may be employed in practicing the subject matter described herein. It is intended that the following claims define the scope of the disclosure and that methods and structures within the scope of these claims and their equivalents be covered thereby.

Certain Definitions

The term "amorphous" as it is used in the description of the present materials, thin films, nano-films, deposition chemistries, compositions, surfaces, devices, and methods of use is defined as a solid phase material that has no crystalline structure and no stoichiometric formula. A particular attribute of the amorphous materials and methods of the present invention is that they possess the characteristic of permitting the ingress of protons into them when they are in an aqueous or partially aqueous environment, such that protons are able to invade the amorphous network of the material (such as the thin film/nano-film treatment provided on a surface), and subsequently release cations (e.g., Si) into the surrounding environment. This is different from conventional and/or standard amorphous materials, such as a glass window, in that conventional amorphous materials are reinforced with other elements and/or constituents, resulting in an amorphous material that does not readily allow it to dissolve in an aqueous environment. Thus, the term amorphous as it is used in the present materials are soluble or at least partially soluble in an aqueous in vitro and/or in vivo environment.

As used in the description of the present invention, all reference to silica, Si—O, and, or other silicon oxygen materials will be denoted SiOx or SiO2.

As used in the description of the present invention, all Si—N, silicon nitride, Si3N4, or other silicon and nitrogen compounds are referred to as SiNx or Si3N4

As used in the description of the present invention, all SizOxNy, (Si—Si)z(Si—O)x(Si—N)y, silicon oxynitride, or any other combination of Silicon, oxygen and nitrogen are referred to as Si(ON)x.

As used in the description of the present invention, the term "nanofilm" includes any film or covering comprising Si(O)X (e.g., SiO2), Si(ON)x, and/or SiNx (e.g., Si3N4) in the form of nanoparticles, nanospheres, or nanorods. In some embodiments, the nanofilm comprises nanoscale particles that form a nano-network film on a surface.

As used in the specification and the appended claims, the singular forms "a", "an" and "the" include plural references unless the context clearly dictates otherwise. Thus for example, reference to "the method" includes one or more methods, and/or steps of the type described herein and/or which will become apparent to those persons skilled in the art upon reading this disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Example 1—Materials and Methods

The present example demonstrates the utility of the present invention for providing an amorphous silicon containing thin film and/or nano-layer at a surface.

Si-wafers were used as substrates for preparation of an amorphous silicon oxide (SiOx) nanolayer. Si wafers were etched (100 nm) using optical lithography combined with dry reactive ion etching. After etching was performed, SiOx coatings were prepared by PECVD. Devices are then characterized using SEM to confirm etch depth and coating uniformity.

Raman Spectroscopy was used to determine post-process function group analysis. X-ray absorbance near-edge structure spectroscopy was used to determine Ca and O coordination on surfaces post-process. Cell-free in vitro testing was then conducted to determine the resultant surface chemistry using XANES while dissolution behavior was analyzed using contact angle analysis. Cell culture testing is conducted to determine cellular response to the coating surface in terms of attachment and gene expression (measured by quantitative PCR (polymerase chain reaction)). Imaging of cells on device surface was imaged using SEM analysis.

Device Fabrication:

In Vitro Testing:

Cell-free in vitro testing was conducted to determine the effect of in vitro conditions on the dissolution and surface chemistry of PECVD SiOx. Devices were immersed in alpha minimum essential medium for a period of 6, 12, 24, and 48 hours. Contact angle measurements were performed using STANDARD ELLIPSOMETRY.

X-ray Absorption Near Edge Structure (XANES) Spectroscopy: XANES spectroscopy was performed at Canadian Beamline. XANES is an excellent tool to probe the local coordination of atoms and determine their valence states. The P L-edge spectra was probed using the Plane Grating Monochromator (PGM) beamline that operates at the low energy range between 5-250 eV, a step size of 0.1 eV and shutter opening of 50 µm×50 µm was used, spectral information was acquired over the energy range of 130-155 eV. The Ca L-edge and O-K edge were probed using the Spherical Grating Monochromator (SGM) beamline that operates in the intermediate energy range of 250-2000 eV. A step size of 0.15 eV and shutter opening of 100 µm×100 µm was used. The Ca L-edge spectra was acquired between 340-360 eV that corresponds to the energy range for both the L2 and L3 transitions in Ca and between 525 and 560 eV that corresponds to the energy range for the core shell (K absorption edge) excitation for oxygen. Spectra were obtained for the virgin as fabricated SiOx surfaces as well as after exposure to cell culture.

Cell Culture: Cell culture testing was conducted to demonstrate the effect of PECVD amorphous silicon oxide (SiOx) on human periosteum cell osteogenic differentiation. Human periosteum cells were obtained from a private source, and cultured to passage 4 for use in the present studies. Periosteum cells are undifferentiated progenitor cells derived from the periosteum, a membrane that covers the outer surface of all bones except at the joints of long bones. These undifferentiated progenitor cells develop into osteoblasts and chrondroblasts, which are essential to the bone healing and bone regeneration process.

Cells were cultured in 150 cm2 flasks until confluence and seeded onto device and control (amorphous silica glass cover slip) surfaces at 100,000 cells per cm2. Cells were counted using a standard hemocytometer and optical microscope. Cells were given a cell culture medium formulated to induce differentiation (alpha modified essential medium, 10% fetal bovine serum, % penicillin-streptomycin, 50 ppm ascorbic acid) and allowed to culture for 3 days. Cells were lysed using RNeasy (Qiagen Inc., Valencia, Calif.), total RNA converted to cDNA (RTS conversion kit, Promege, Madison, Wis.), and the cDNA assayed to determine relative gene expression (Collagen (Coll), Lysol oxidase (LOX), osterix (OSX), superoxide dismutase (SOD1)) using quantitative polymerase chain reaction (qPCR, Bio-Rad, Emoryville, Calif.). The materials employed in these gene expression studies are described in detail in Veranasi et al. (2009) [21], which reference is specifically incorporated here by reference for this purpose.

Imaging: Imaging of cell layers was conducted using a Hitachi S-3000 Environmental scanning electron microscope operating in secondary electron mode at accelerating voltages ranging from 5 kV to 15 kV.

Statistics: Statistical analysis was performed using standard t-test for between groups' comparisons. All experiments were conducted in triplicate and statistical significance was determined using $p<0.05$ for statistical significance. Statistical calculations were conducted using SigmaPlot 12.0.

Results:

Example 2—Nano/Micro-Grooved Treated Surfaces—Effect on Reducing Contact Angle

Figure 1B:
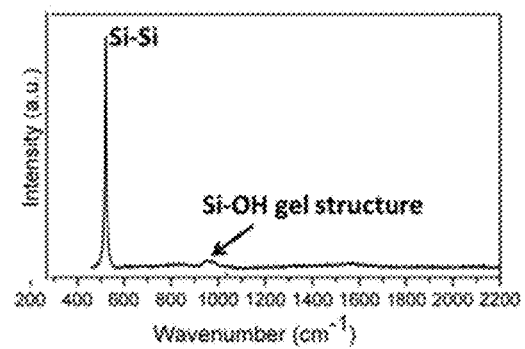
Figure 1C:
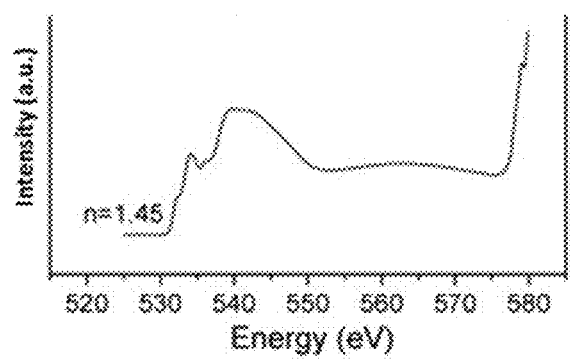
Figure 1D:
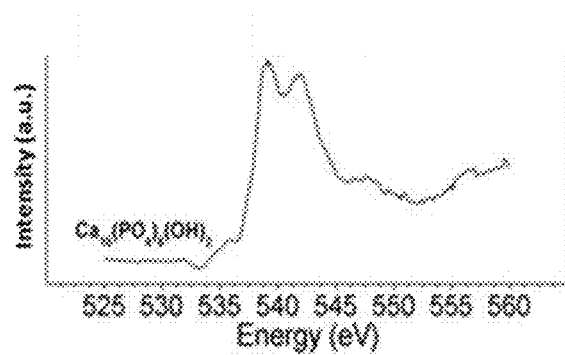

The fabricated device shown at FIG. 1A shows the nano-/micro-grooved etch pattern. The PECVD SiOx nanolayer was confirmed by Raman Spectroscopy (Figure1B), in which a residual silanol (950-1000 cm −1, Si—OH) surface layer remained after the PECVD process was completed. Although XANES analysis showed a slight evidence of O coordination with phosphate (540 eV nm, FIG. 1C vs. HA standard, FIG. 1D) on the SiOx surface, no evidence of phosphate or calcium was observed. This indicated that a lack of surface HA prior to in vitro studies.

Sample devices were immersed in vitro to determine their resultant dissolution behavior and resultant surface chemistry. Results from contact angle testing (FIG. 2A) showed a rapid decrease in the contact angle with increasing dissolution time. The rate of contact angle change was proportional to $1/t^{1/2}$, indicating dissolution behavior by the device surface. While not intending to be limited to any particular mechanism of action or theory, this rapid decrease in contact angle may be attributed to the formation of —OH moieties on the surface, thus rendering the surface more hydrophilic FIG. 2C is the Ca L2,3 edge XANES spectra for hydroxyapatite, and FIG. 2B is the corresponding spectra for the in vitro sample with a refractive index of 1.45 after 24 hours. It is clearly evident from the spectra that Ca is present on the surface and is likely to be in the form of HA.

In order to confirm the coordination of oxygen in the structure, O K-edge XANES spectra were also acquired. FIG. 2D is the O K-edge spectra from the same sample where the Ca L2,3 edge was acquired, and FIG. 2E is the corresponding spectra from HA. While it is evident that O is present on the substrate, the O K-edge spectra indicates that O is present in a more complex state than a simple HA. However, it is clear that in this case, it is not present in the form of carbonates that have a characteristic pre-edge peak at around 530 eV. This is absent in the preset case. It is most likely that O is present in the form of a mixture of HA and other phosphates. The corresponding P L-edge spectra of the in vitro sample (FIG. 2F) and HA (FIG. 2G) also indicate the presence of P in the in vitro tested sample, and likely present in the form of phosphate which are likely to be a mixture of HA and other phosphates. Taken together, these results indicate that HA and other phosphates form on the surface within 6 hours after in vitro immersion, and that contact angle was significantly reduced at surfaces treated according to the present methods.

Example 3—Effect of $Si^{4+}$ on Human Periosteum Cell Osteogenic Differentiation The present example demonstrates that devices having an etched amorphous silicon oxide (Si(O)x) treated surface affects human periosteum cell osteogenic differentiation, and are therefore useful in promoting bone regeneration.

Human periosteum cells were used in the present studies. Substrates, cells, and cell culture testing was conducted as described in Example 1.

Figure 3A:
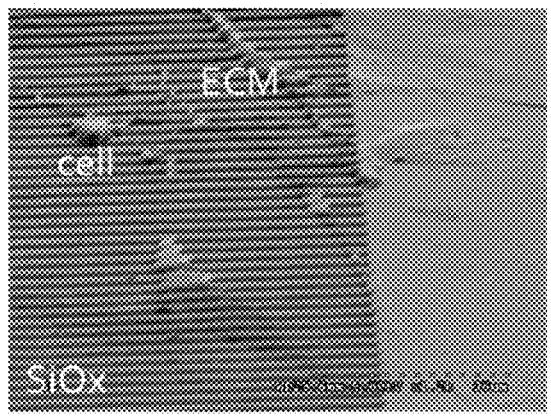
FIG. 3A shows the cellular response of human periosteum cells to attach, migrate, and deposit extracellular matrix over the amorphous Si(O)x (specifically, SiO2) surface over 3 days.
Figure 3B:
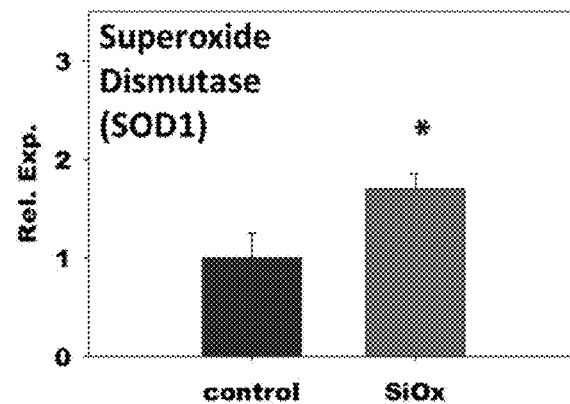
FIG. 3B shows the enhancement of the expression of SOD1 (superoxide dismutase) by human periosteum cells on an Si(O)x surface within 24 hours, compared to control.
Figure 3C:
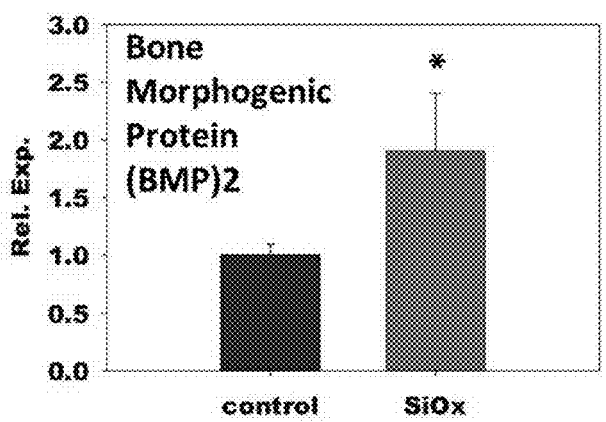
FIG. 3C shows the enhancement of the expression of BMP2 (bone morphogenic protein) by human periosteum cells on an Si(O)x surface within 3 days, compared to control.
Figure 3D:
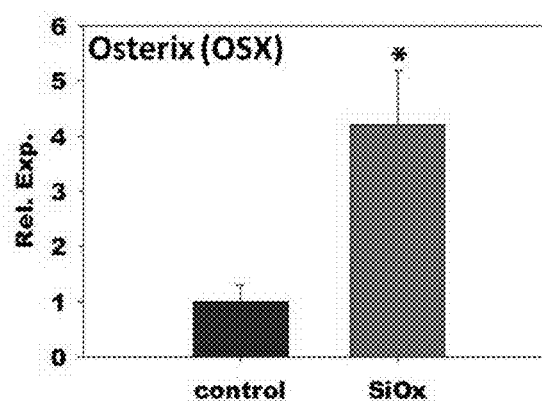
FIG. 3D shows the 4-fold enhancement of expression of OSX (osterix) by human periosteum cells on an Si(O)x surface within 3 days, compared to control.

The results from this study are demonstrates at FIG. 3A-FIG. 3 D. Cell culture testing indicated that these human periosteum cells attached and migrated over the etched Si(O)x surface (FIG. 3A). Gene expression analysis showed that these surface treatments enhanced the expression of SOD1 (day1), OSX (day 3) (FIG. 3A an FIG. 3B), and BMP2 (day 3) (FIG. 3C), as compared to un-etched amorphous silica glass cover slip controls (control for periosteum cell gene expression response) by human periosteum cells. A 4-fold enhancement of expression of OSX (oserix) by human periosteum cells is also demonstrates (FIG. 3D).

Thus, these surfaces enhanced osteogenic differentiation of human periosteum cells, and may be used to regenerate human bone in vivo.

Example 4—More Rapid Formation of Hydroxyapatite (HA) on an Amorphous Silicon Oxide (SiOx) Treated Surface This example demonstrates the utility of the amorphous silica coatings prepared by lithography and chemical vapor deposition for promoting osteoblast expression of antioxidant enzymes and osteogenic markers, and enhanced osteoblast differentiation.

The rapid formation of HA and other phosphates on the SiOx surface was probably owed to the availability of Si—OH groups on the surface after PECVD. The rate of Si—OH surface formation on surfaces has been described as the limiting step to silica-gel layer formation and subsequent HA formation [22]. Immersion of amorphous silica and amorphous silicon oxynitride in alpha minimum essential medium and subsequent formation of HA involves several steps (Id). These steps include rapid ion exchange of protons in solution with alkali cations in the glass network, alkali earth cation and phosphate ion release from the glass, hydroxylation of Si—O groups within the glass, and migration of silanols to the glass surface. PECVD SiOx, on the other hand, forms surface silanols intrinsically on the amorphous silica surface. This reduction in mechanistic complexity provides for a more rapid HA formation on a surface.

Gene expression results obtained in this work showed that the PECVD SiONx surface treatment enhanced various osteogenic markers. SOD1 expression was observed to be enhanced within 24 hours after cellular attachment to SiONx surfaces. This was followed by BMP2 and OSX enhancement after 3 days. The sequence in which OSX expression follows SOD1 and BMP2 expression is consistent with known osteogenic timelines. Thus, the PECVD SiONx surface could have up-regulated SOD1 and BMP2 along different cell receptor pathways and their respective impact on OSX expression could be additive.

Hydroxyapatite (HA) or other calcium phosphate incorporated bioceramics and glasses have not shown any antioxidant effect. Thus, the up-regulation was identified to occur via ionic silicon release from the surface and the interaction of ionic silicon with bone cells (osteoblasts). As noted herein, ionic Si also is demonstrated to up-regulate other bone-related markers (osteocalcin, core-binding factor a, collagen) that are essential for bone healing. Considering that PECVD SiONx leaves surface Si—OH groups readily available after processing, such an effect is attributed to ionic silicon release, among other things. Studies involving gene knockdown models will be implemented to fully understand the mechanisms behind this antioxidant effect.

The SiONx treated surfaces also provide for hastening and strengthening bone apposition of dental and orthopaedic metal implants to bone. These treated surfaces also enhance the expression of antioxidants and osteogenic markers to rapidly form bone matrix. It is envisioned that the herein described treated surfaces have applications in bone healing where ROS regulation is needed. A greater breadth of bone healing applications that could benefit from PECVD SiONx than those specifically exemplified here are therefore embraced within the scope of the present invention.

Coatings prepared by lithography produced hierarchal nano-/micro-grooves that facilitated cellular attachment, while SiONx coatings increased SOD1, OSX, and BMP2 expression within the first 3 days of osteoblast differentiation. XANES analysis indicated formation of hydroxyapatite within 6 hours during in vitro testing. Taken together, these results indicated that nano-/micro-grooved SiOx coating prepared by lithography and PECVD enhances osteogenesis and hydroxyapatite formation during early stage osteoblast differentiation.

Example 5—Fabrication; $Si^{4+}$ Effect on Gene Expression and as an Antioxidant The present example details the fabrication of the bio-inspired medical devices (e.g., metal device) having a nano-/micro-patterned SiONx-based overlay. SiONx-based materials were chosen based on their uses as FDA approved materials used in dental and medical applications. [22,34].

Lithography was used to etch 3D nano/micro-groove patterns. Chemical vapor deposition (CVD) was used to form Si(ON)x overlays onto at least one surface of the device by reacting gaseous Si, O, and N reagents. The nano/micro-pattern and Si(ON)x overlay combination is demonstrated to accelerate surface HA formation, osteoblast attachment, osteogenic transcription factor expression, and biomineralization.

$Si^{4+}$ was found in the present studies to enhance SOD1 expression and to reduce $H_2O_2$. Therefore, the results achieved with the devices herein established that $Si4^+$ plays an antioxidant role during osteogenesis.

In this example, the following results are presented: (1) the effect of $Si^{4+}$ on SOD1 expression and collagen matrix synthesis and strength in vitro, and (2) The effect of Si(ON) x-modified devices on bone regeneration for rapid healing in critical sized defects in vivo. New classes of biomedical devices that provide antioxidant and structural support during fracture healing are thereby created according to the present invention.

$Si^{4+}$ is shown to serve an antioxidant role. This is demonstrated through the showing here on the effect of $Si^{4+}$ on SOD1 expression, which in turn enhances osteogenesis. Mechanistic details of the effect of $Si^{4+}$ and $H_2O_2$ on wild type (WT) and SOD1-null osteoblasts will be shown by measuring SOD1 (0-3 days), RUNX2 (1-7 days [3]), OSX (2-7 days [18,19]), COL(I) (1-20 days [18]), and osteocalcin (3-28 days [21]) expression, and collagen matrix 96-14 days [21]) and biomineral formation (20-30 days [18, 19]). The bio-inspired biomedical devices of the present invention provide antioxidant and structural support. The nanotechnology-based methods provide nano-patterns and chemistries that enhance osteogenesis. Lithography will produce patterned hierarchical nano-/micro grooves for increased osteoblast attachment and ECM formation. CVD will produce Si(ON)x nano-layers (i.e. silicon oxynitride, Si(ON)x) onto patterned device surfaces for increased device strength, HA formation rate and sustained $Si^{4+}$ release. Devices having a surface treated as described herein thereby provide enhance bone regeneration during fracture healing.

Some efforts with Ca—P-based scaffolds (FIG. 5A) yielded low levels of mineralization after 4 weeks in rat skulls (FIG. 5B). This was owed to the scaffold's slow degradation, limited mineral ingress, gaps between the scaffold and bone (FIG. 5C), and noted inability to enhance antioxidant activity. As noted above, critical sized fractures generate high ROS, which limits new bone formation by interfering with osteogenesis and reducing osteoblast viability (FIG. 5D). Because normal healing occurs after 4-8 weeks in large defects [10] and these Ca—P-based scaffold materials did not accelerate bone regeneration, these approaches were abandoned.

Amorphous silica-based biomaterials are characterized by an adequate degradation rate and an ability to facilitate matrix ingress for biomineral adhesion [18, 20-21, 37-40]. The key degradation product, Si4+, was found to enhance Runx2 and OCN expression by 3-5 fold. It was also found that other key markers [COL(1), LOX, OSX, FIG. 6A-FIG. 6C] and elongated collagen fibers in extracellular matrix (ECM) were enhanced by Si4+ vs untreated ECM (FIG. 6E, FIG. 6F). An increase in SOD1 expression (FIG. 6D) was also found, when knocked down using siRNA, to knock down COL(1), OSX, and LOX (FIG. 6A-D) for control and $Si^{4+}$ treatments.

Figure 4:
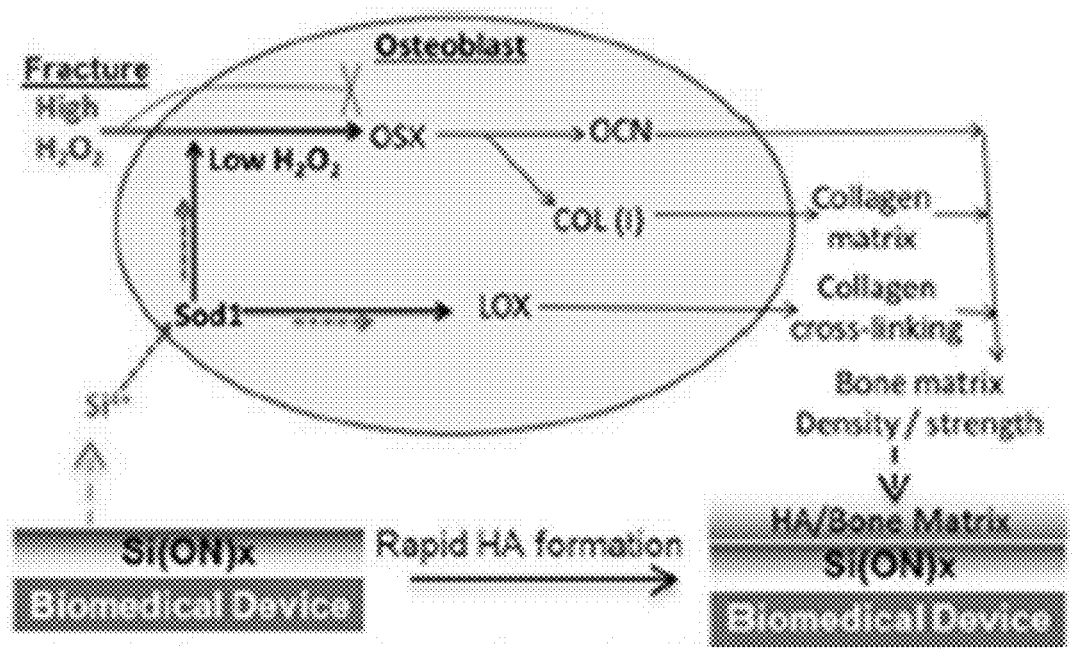
FIG. 4. Is a diagrammatic flow chart outlining the pathway by which Si4+ plays an antioxidant role, and the role of amorphous Si(ON)x in generating structural HA. Structural HA provides support for bone cells, and thus rapid bone healing.

SOD1 knockdown osteoblasts were found to produce very little matrix (FIG. 6G, H). Thus Si4+ enhances osteoblast gene expression and collagen matrix synthesis via SOD1 enhancement (FIG. 4).

The dose-dependent effect of $Si^{4+}$ on this antioxidant mechanism during collagen and biomineral formation will also be examined.

Figures 7A, 7B, 7C, 7D, 7E:
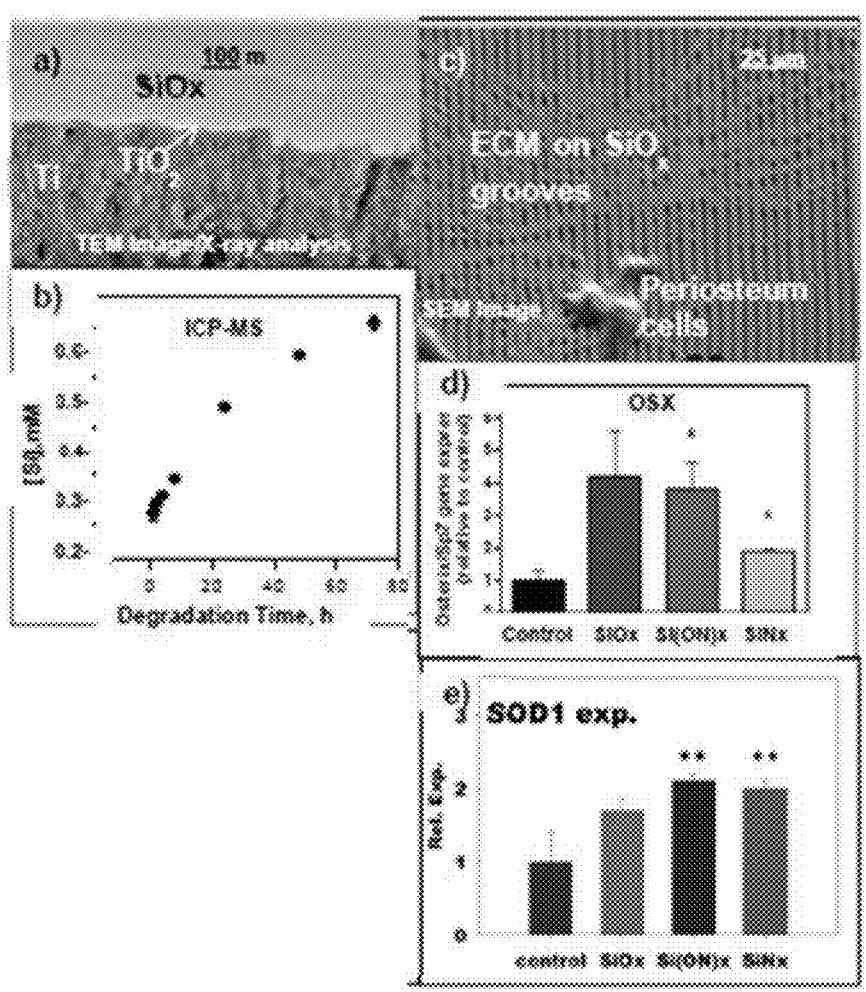
FIG. 7A shows that a grooved, CVD of amorphous Si(ON)x overlay on a surface enhances osteogenesis, (CVD Si(O)x on 100 nm grooved Ti/$TiO_2$).
FIG. 7B demonstrates that a surface treatment with amorphous Si(O)x shows an initial surface-reaction controlled $Si^{4+}$ release at 72 hours.
FIG. 7C shows human periosteum cells form ECM on nano-grooved amorphous Si(ON)x.
FIG. 7D shows enhancement of OSX gene expression (at 72 h) on a nano-grooved amorphous Si(ON)x surface.
FIG. 7E shows enhancement of SOD1 gene expression (at 48 h) on a nano-grooved amorphous Si(ON)x treated surface.

One of the bio-inspired devices (FIG. 7A) included a nano-/micro-patterned Ti (100-150 nm depth×1-2 μm wide grooves) using lithography. Hierarchal patterns were fabricated onto a Cr-coated borosilicate glass, and then transferred by ultraviolet light onto spin-coated negative photo-resist on Ti surfaces. After development, patterns were etched into the Ti surface using dry reactive ion etching with cryogenic Cl(g). After resist removal, Ti surfaces were overlaid with SiOx (100 nm) by CVD. CVD uses reagent gases to form overlays onto device surfaces [41-45]. Reagent gases included tetraethylene oxysilane (TEOS) for Si, O2 and N2. After positioning the device surface in the CVD chamber, reagent gases reacted to form SiOx/Si(ON)x overlays at 100-300° C., varied O2/N2 ratio, and 20 nm/min growth rates on Ti surfaces.

Figure 8A:
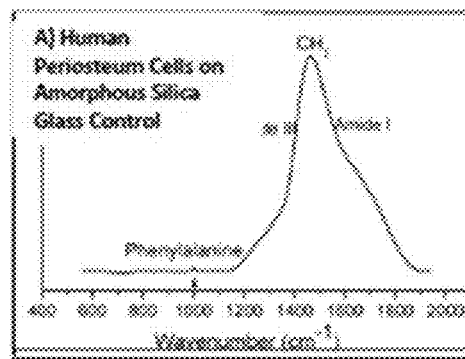
FIG. 8A shows human periosteum cells on amorphous silica glass (Control).
Figure 8B:
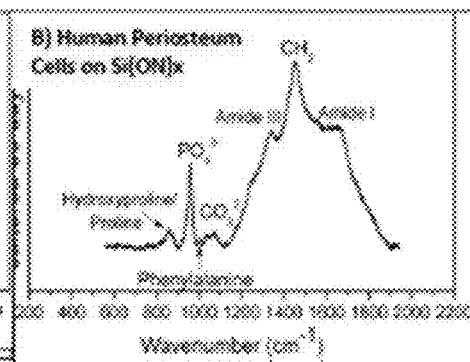
FIG. 8B shows human periosteum cells on an amorphous Si(ON)x treated surface enhances human periosteum cell biomineralization events. Raman Spectroscopy showing the inducement of collagen formation by periosteum cells on amorphous glass ($CH_2$, s,ofr 2 & II, phenylamine). Amorphous $Si_3$—ONx surface treatment induced biomineralization *($PO_4$, $CO_3^{2-}$) within 3-4 weeks.
Figure 8C:
FIG. 8C presents light microscopy showed mineralized nodules on Si(ON)x($C_1$*).
Figures 9A, 9B:
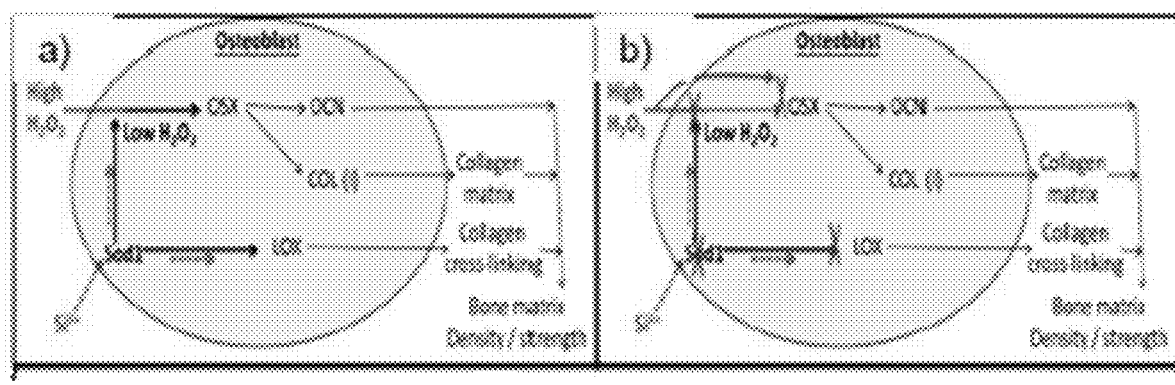
FIG. 9A presents a study design schematic of the effect of $Si^{4+}$ on WT.
FIG. 9B presents a study design schematic of the effect of $Si^{4+}$ on Sod1-null osteoblast.

SiOx release of Si4+ was steady with time (FIG. 7B), until the surface became self-limiting to form Si4+ (measured by inductively coupled plasma mass spectrometry, ICP-MS). Devices were seeded with human periosteum cells which rapidly traversed the etched Si(ON)x overlay and formed ECM (FIG. 7C) vs SiOx overlays in 6 days and had enhanced OSX (72 h) and SOD1 (48 h) expression (FIG. 7D, 7E) vs control samples (amorphous silica glass). Periosteum cells are osteoblast progenitor cells that are involved in defect healing [46]. After 3-4 weeks in vitro, Raman spectra (used to identify carbonate (CO32-) and phosphate (PO43-) biomineral functional groups [19]) showed that only Si(ON)x samples had biomineral formation on their surfaces vs. amorphous silica glass control samples (FIG. 8A-8C). This was likely owed to the formation of a Ca—P rich layer (resembling HA) on the Si(ON)x surface (FIG. 8C). These results indicate that nitrogen and oxygen incorporation can enhance osteogenesis and biomineralization. These overlays were formed on metal or polymer materials to study their effect on the rate of bone formation in critical size defects.

Dose/temporal effect of Si4+ on SOD1 expression, H2O2 reduction, osteogenic differentiation, and collagen and biomineral formation in wild-type (WT) and SOD1-null osteoblasts (from calvaria of SOD1 knockout mice). Comparison was made to study control treatment (cell culture media with 50 ppm ascorbic acid [AA]). The mechanistic details of these events is examined, including measurement of SOD1 (0-3 days), RUNX2 (1-7 days), and OSX (2-7 days), COL(1) (1-20 days), and OCN (3-28 days) expression, collagen matrix (6-14 days), and biomineral formation (20-30 days). Si4+ is demonstrated to enhance osteogenesis via SOD1 enhancement. The identification of this mechanism will be used to enhance collagen matrix synthesis and strength.

WT/SOD1-null primary osteoblast pilot study: Prior to $Si^{4+}$ studies, primary SOD1-null osteoblasts (Jackson Laboratories) will be used to confirm SOD1 knockout for 30 days to study the effect of SOD1 deficiency on osteoblast viability, gene/protein expression, and collagen/biomineral formation. Comparison will be made with WT osteoblasts. These studies will be repeated with H2O2 addition (0-0.5 mM) to determine the effect that prolonged 11202 exposure has on osteoblast viability, differentiation, and mineralization for 30 days. Study Controls will be WT osteoblasts exposed to culture media containing 50 ppm AA.

Figure 10A:
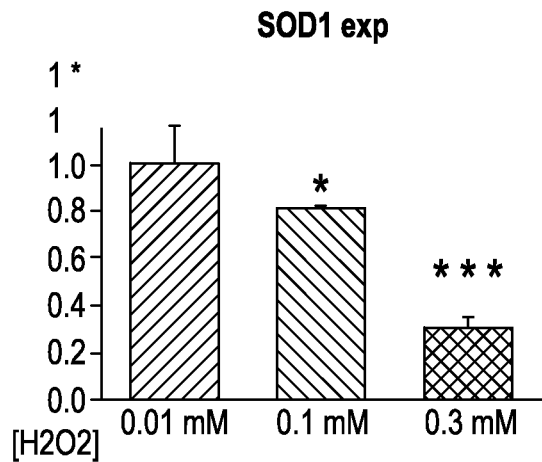
FIG. 10A demonstrates human periosteum cell SOD1 expression is decreased with increasing H2O2 dose.
Figure 10B:
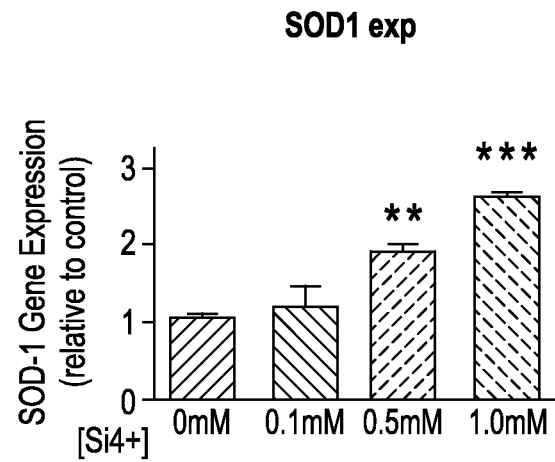
FIG. 10B demonstrates that $Si^{4+}$ enhances SOD1 expression by human periosteum cells.
Figure 10C:
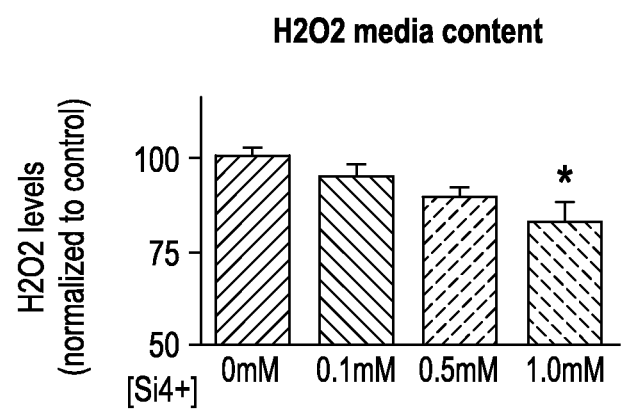
FIG. 10C demonstrates that $Si^{4+}$ reduces ROS (H2O2) in human periosteum cells.

$Si^{4+}$ effect on WT/SOD1-null Osteoblasts (FIG. 6a/b): We will expose primary WT and SOD1-null mouse calvarial osteoblasts to Si4+ (range: 0.1-1.0 mM Na2SiO3) to confirm osteogenic and biomineral enhancement by Si4+ on osteoblasts and confirm that such enhancement is inhibited by SOD1-deficiency for 30 days. Once confirmed, WT and SOD1-null osteoblasts will be exposed to H2O2 (0-500 µM, 30 days) to determine the effect of Si4+ dose to induce SOD1 expression, ROS reduction, and collagen/mineral production. Si4+ treatment effects will be compared with the study control (WT osteoblasts exposed to media+AA). In the present studies (FIG. 10), human periosteum cell SOD1 expression is demonstrated to be decreased with increasing ROS, while Si4+ dose enhanced SOD1 expression and reduced ROS activity. Similar results are expected for osteoblasts exposed to elevated ROS.

Example 6—Cell/ECM Characterization

Cell lysates will be assayed for gene expression using qPCR while protein and media lysates will be assayed by ELISA. Collagen/biomineral will be visualized using polarized light microscopy, Raman Spectroscopy, and SEM while mechanical properties (e.g., modulus, hardness) will be measured by nano-indentation (Hysitron Ubi® TriboIndenter®). Real time ROS will be imaged intracellularly (IMAGE-IT LIVE ROS for fluorescence microscopy, Life Tech Inc. [47]) and extracellularly (Apollo 4000 electrode, WPI Inc. [48]).

Statistics: 3 independent experiments will be conducted with 4 treatments, 3 replicates, and 4 time points (every 7 d) to give 9 replicates/treatment/time points. All treatment results will be normalized to control treatment results. 2-way ANOVA (factors: time, dose) with Tukey's post-hoc tests will be used. Power computations are based on α=0.05 and anticipated effect size of d=2.0 to yield ≥80% power.

Timeline: Pilot, H2O2, Si4+, and Si4+-H2O2 studies on WT/SOD1-null cells and full characterization with repeat studies) will take 180 days to complete.

Results: H2O2 levels (>15 µM) are expected to induce down-regulation of OSX, RUNX2, COL(1), and OCN expression. Si4+ treatment should decrease H2O2 levels, enhance SOD1, OSX, RUNX2, COL(1), OCN, and LOX expression, and increase collagen matrix and biomineral synthesis, density, and strength in WT cells. In SOD1-null cells, these enhanced effects are not expected with down-regulation of all osteogenic markers, no change in 11202 levels, decreased elongated collagen fiber density, and decreased matrix strength (<25%).

Other antioxidant enzymes (e.g., glutathione reductase, catalase) may be affected, and therefore their expression will be assayed. Other molecules involved in collagen synthesis (integrins [49], Rab GTPase protein transporters [50]) will also be monitored with Si4+. Primary mouse osteoblasts have different sensitivity to Si4+ than human or rat osteoblasts or osteoprogenitors. Thus, other cell types (periosteum cells or periodontal ligament fibroblasts) will be used to evaluate these differences. SOD1 deficiency may decrease cell viability. Alternatively, SOD1 shRNA will be used to confirm 30 day knockdown.

Si4+ is shown to enhance osteogenesis through the enhancement of antioxidant enzymes, thereby illustrating its antioxidant role. By demonstrating this phenomenon, a new mechanism for healing defects present in a compromised tissue oxygen environment is accomplished. Oxidative stress regulation and management in fractures at an oxygen compromised site greatly improves the treatment strategies for bone regeneration.

Example 7—Effect of Nitrogen Content on the Rate of Si4+ Release, Bone Regeneration and Fracture Healing at an Amorphous Si(ON)x-Surface The effect of nitrogen content in Si(ON)x-modified devices on the rate of Si4+ release, surface HA formation, biomineralization and bone regeneration, is demonstrated in the present example.

Figures 11A, 11B:
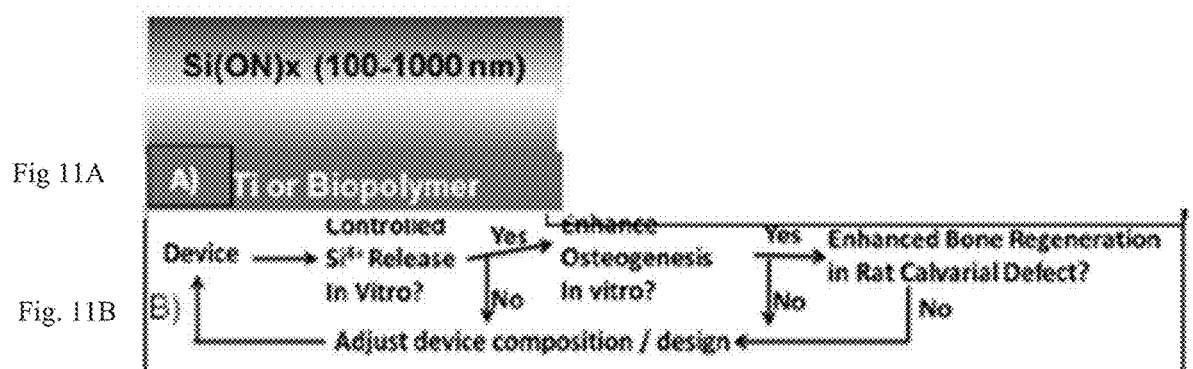
FIG. 11A presents a bio-inspired biomedical device with CVD Si—O/Si—O—N layers and etched nano-/micro-grooves.
FIG. 11B presents a flowchart of device degradation and implantation studies.

Devices (FIG. 11A) were formed using lithography to etch nano-micro-grooves and CVD to form overlays of Si(ON)x onto biomedical materials (e.g., Ti, PLA). PLA was chosen based on its biodegradability, relatively high melting temperature (~175 C) and used in CVD and lithography [51, 52]. Control samples were bare Ti or PLA with etched grooves to discern the effect of the etch from the Si(ON)x overlay. The present example identifies candidate device chemistries that will be used for in vivo testing. The effect of candidate devices (FIG. 10B) on bone regeneration in a critical size rat calvarial defect model is also examined (See infra). Bone density will be measured over 12 weeks. Results will be compared between Si(ON)x-modified and control devices. The most optimal device chemistry for accelerating bone defect healing is thereby identified.

Biomaterial (Ti, PLA) biocompatibility will be assessed. Rat Calvarial defects are created as described below (Animal Surgery). Each rat will have 1 device (Ti or PLA) on one side of the parietal bone midline and one empty defect. Animals will be examined on weeks 2 and 4 to measure bone density for biomaterial-filled defects vs unfilled defects according to the methods and power analysis described below (Animal Surgery, Statistics). Serum levels of ROS, SOD1, and OCN will also be assayed. Ti and PLA serve as biomaterial controls for later in vivo testing.

Device Fabrication:

Commercially pure Ti (Goodfellow, Inc.) and biopolymer (PLA, Polysciences, Inc.) substrates will be etched using lithography to create grooved patters. Surfaces are overlaid by CVD with Si(ON)x, which chemically bonds to the underlying metal/polymer surface. Control samples will consist of etched Ti or PLA without overlays. Fabrication procedures as outlined herein were employed.

Figure 12:
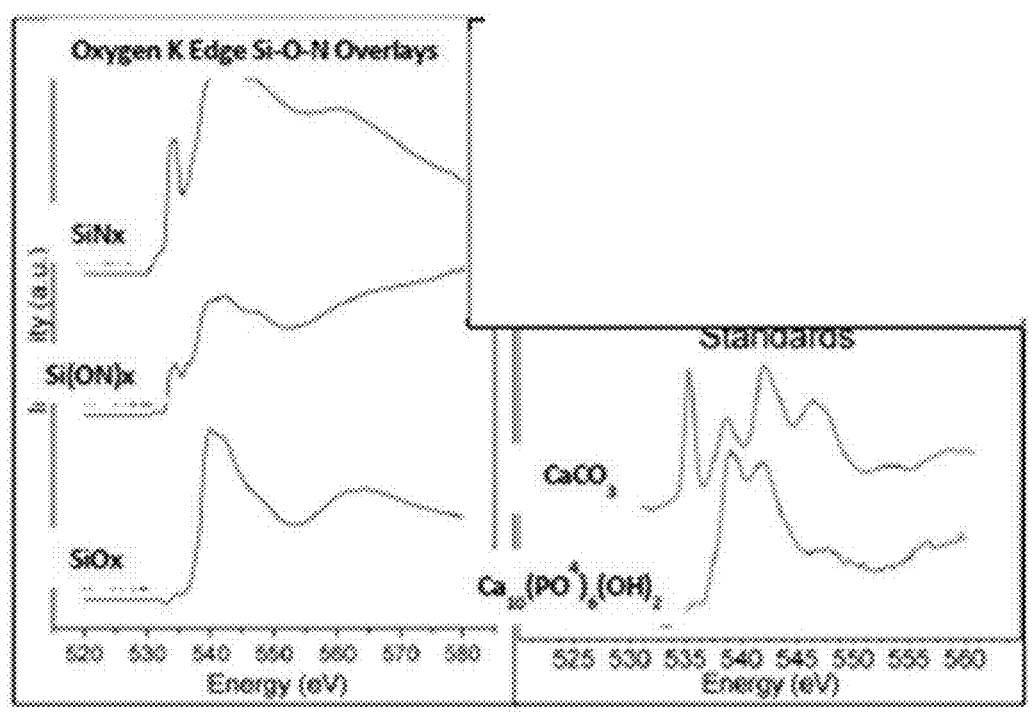
FIG. 12. X-ray absorbance near-edge spectroscopy (XANES) shows surface HA ($CA_{10}((PO^4)_6(OH)_2$ 540 eV). Ca and P peaks were also present.

In Vitro Testing/Degradation/Characterization:

Si(ON)x-modified and unmodified device controls will be measured for HA formation (FIG. 12) and Si4+ release in vitro for 5-10 days using ICP-MS. Device design/composition will be adjusted for proportional Si4+ release with degradation time. The optimized Si(ON)x-modified metal/biopolymer device will be tested with rat calvarial osteoblasts for enhanced mineralization to identify candidate devices for in vivo testing. After device fabrication and testing, changes in morphological, structural, chemical, and mechanical properties will be characterized using methods in Aim 1. Fabrication, in vitro testing, and characterization generally is completed within 90 days.

Rat Model/Animal Surgery/In Vivo Testing:

Young adult female (200 g) and male (250 g) Sprague Dawley rats with critical sized (>5 mm) calvarial defects will be used. This animal model is recognized by those of skill in the art as an acceptable model for orthopaedic and dental implant bone growth [53]. Bone growth is shown using this model after 4-8 weeks.

Rats will be anesthetized and sedated by an intraperitoneal injection of ketamine (90 mg/kg, Ketaset III, Fort Dodge, USA) and xylazine (10 mg/kg, LLOYD laboratories, USA). A 1.5 cm long mid-sagittal incision will be made with a sterile scalpel blade. Full thickness skin and periosteum will be raised to expose the calvarial bone (Parietal bone). A 5 mm diameter trephine will be used to drill a standard surgical defect on both sides of midline while the surgical site and surrounding tissues will be continuously irrigated with a cold saline solution to prevent heating the surrounding bone and to keep the soft tissue moist. The depth of the defect will be carefully made and the loosened bone will be carefully removed so as not to damage the dura. A sterile 2"×2" piece of gauze dampened with sterile saline will be used to apply firm pressure on the site to prevent excessive bleeding. Implants (of the same dimension as the defect, will then be carefully placed and a small gap (<1 mm) will be maintained. The periosteum and skin (which will be kept moist in saline during the surgery) will then be closed in layer with an absorbable gut suture and staples respectively. After the completion of experiments, rats will be euthanized (>990% CO2 and monitored until the animal is dead). (Note: each rat will have 1 device on each side of the midline one with the bare device (Ti or PLA) and one with surface modification (Ti—Si(ON)x, PLA-Si(ON)x). Animals will be examined on weeks 2, 4, 8, and 12 to measure serum ROS, SOD1, and OCN levels and bone density by micro-computed tomography (at BCD). Biopsied samples will be analyzed for bone matrix ingress by SEM/TEM analysis, histology, and immunohistochemistry for morphological or matrix protein changes after 12 weeks.

Statistics:

Comparisons for in vitro cell culture studies follow those outlined in Aim 1 For in vivo experiments, comparisons will be made between the bare substrate control (e.g., Ti) and the Si(ON)x-modified substrate (experimental). The general linearized model and post hoc paired t-tests will be used to evaluate left vs right differences within individual rats, each receiving test and control treatment; sides will be randomized and coded. Evaluation will be made such that the treatment group of each defect will be masked to the examiner. The overall design will consist of 1 set of experimental and control groups and 4 time points. Based on in vitro data of the smallest difference of interest (i.e., control vs Si(ON)x, FIG. 8d), a power analysis indicated that 36 rats are needed. Sample size was increased from in vitro experiments to 9 rats per group in anticipation of greater variability in the animals' vs cell cultures. Specifically, 9 rats will be implanted each with 1 experimental and 1 control group and will be sacrificed at 4 time points (2, 4, 8, 12 wks.) to give 36 rats, which will detect an effect size of d=3.2 where $\alpha=0.05$ (power $\geq 80\%$). A separate experiment will be similarly arranged for PLA (control) and Si(ON)x-modified PLA (experimental) (36 rats) and for PLA-treated or Ti-treated defects vs. unfilled defect controls for 2 and 4 weeks (36 rats), thus, a total of 108 rats will be used.

Results:

Si(ON)x overlays adhered well to Ti/biopolymer substrates, sustained Si4+ release (0.1-1.0 mM Si4+ for 5-10 days), formed surface HA, and revealed that an oxygen-to-nitrogen ratio of unity will maximally enhance biomineralization. These animal studies also demonstrated a higher bone regeneration rate in defects filled with a device having a treated surface (3-4 weeks) vs devices without a treated surface (8 weeks), with Si(ON)x allowing higher density of biomineral invasion and presence of collagen and mineral formation as compared to devices not having a treated surface.

PLA and biopolymer surfaces, such as poly-caprilactone, polydimethylsulfoxide, etc., may be treated so as to include a treated surface having a thin film of an amorphous silicon oxide, amorphous silicon oxynitride or amorphous silicon nitride. Conformal patterns due to possible polymer substrate curvature may exist, and therefore soft lithography may be used [35, 54-56]. Soft lithography is similar to standard lithography except patterned elastomeric masks contact print ("stamp") patterns onto the device.

Example 8—In Vivo Bone Regeneration at a Critical Sized Calvarial Defect

The present example demonstrates the utility of the present invention for providing in vivo bone regeneration, and in particular, intramembranous ossification.

Intramembranous ossification is well-known to be the predominant type of healing that occurs within a calvarial defect. This type of healing involves the more complex process of the differentiation of osteoblast progenitor cells into a mineralizing phenotype. The present example demonstrates the successful promotion of this more complex component of the bone healing and bone regeneration process in vitro (FIG. 3, FIG. 3, FIG. 6, FIG. 7, FIG. 14, FIG. 15). No chondrocytic gene expression or cartilage was observed in the present in vitro or in vivo studies, demonstrating that the more complex series of physiological events that promote intramembranous ossification are provided with the materials and methods of the present invention.

In the present defect model, a defect was placed within the intraperitoneal bone between the midline suture and occipital bone. This is recognized as a "critical sized" defect because healing cannot occur, such a volume of bone having been lost so as to render bone healing impossible. There are no chondrocytes within this region, and thus no cartilage is produced within this region. Because of the lack of chondrocytes and cartilage, endochondral ossification cannot take place and healing thus occurs along the path of intramembranous ossification.

The plate included a surface that had been treated to include a thin film/nano-layer of amorphous $SiON_x$ coating deposited by PECVD.

$Si(ON)_x$-based overlays onto metal/polymer devices can structurally support and accelerate bone regeneration within days to weeks after implantation. The following in vivo results show that accelerated bone regeneration is coupled with sustained $Si^{4+}$ release and device surface HA formation. This exogenous control over bone repair can then be linked to control over device fabrication.

Example 9—Wafer Fabrication

The wafer used in the present study was fabricated according to the following protocol.
Wafer Processing:
SiON Wafers:
Step 1—Photolithography.
The equipment used in this step included a hot plate, a spin coater, EVG 620 aligner.
Process Steps/Parameters:
Before starting, the hot plate temperatures were checked with a thermocouple, and adjusted as necessary. The wafer was first cleaned with 5:1 Piranha (H2SO4:H2O2) when using a previously used wafer. Where the wafer being used was a fresh (new) wafer, the step may be omitted. Second, the surface was dehydrated using the hot plate at 200° C. for 5 minutes. A Microposit HMDS primer was then deposited on the surface of the wafer. The primer was maintained at room temperature before beginning. About 80% to 90% of the wafer was covered with primer. The spinning parameters used in the process were 1. Ramp 500 rpm/sec; 2. Speed 3000 rpm; 3. Time: 30 seconds. The wafer was then baked on a hot plate at 150° C. for 90 seconds. The wafer was then provided a Spin coat with S1813 positive resists. This was accomplished by using a resist that was a room temperature before beginning. About 90% of the wafer was covered with primer. Step 1—1. Ramp 100 rpm/sec; 2. Speed 500 rpm; 3. Time: 5 seconds; and Step 2—Ramp 900 rpm/sec, Speed 4000 rpm, time: 30 seconds. The wafer was then soft baked on a hot plate at 90 C for 60 seconds. The wafer was then covered with a completely opaque wafer carrier and brought to EVG 620 Aligner. The wafer was then exposed in the EVG Aligner (ILINE 365) to a dose of 139 mJ/cm2, for an exposure time as defined herein (in constant intensity mode). The wafer was then again soft baked at 110 C for 62 seconds. A photoresist was developed with Microposit MF 319 developer by submerging and agitating the wafer in the developer every 10 seconds, for a total of 43 seconds. The wafer was then rinsed with DI water, taking care not to let the water fall directly on the wafer to prevent/avoid lifting of the pattern on the wafer. The wafer was then dried with N2.

Step 2—Surface Patterning (DRIE):
Equipment:
TRION Deep Reactive Ion Etching System

TABLE 1

Process Steps/Parameters:

| | Press. (mTorr) | ICP Pwr | RIE Pwr | $CF_4$ sccm | Ar (sccm) | Time (sec) |
|---|---|---|---|---|---|---|
| Step 1 | 250 | 0 | 0 | 0 | 250 | 30 |
| Step 2 | 20 | 3000 | 100 | 25 | 0 | 139 |
| Step 3 | 250 | 0 | 0 | 0 | 250 | 30 |

Short Explanation of Steps:
Step 1: Chamber/Line Purge with Argon; Step 2: Anisotropic etching step: 862.5 Å/min, 200 nm total etch depth; Step 3: Chamber/Line Purge with Argon; Step 3: $SiON_x$ Coating (PECVD)
Equipment:
TRION ORION II PECVD/LPCVD System.

TABLE 2

Process Steps/Parameters: All gas flow rates in sccm.

| | $SiH_4$/Ar (15/85%) | $N_2O$ | $N_2$ | $NH_4$ | Ar | Time (sec) |
|---|---|---|---|---|---|---|
| Step 1 | 0 | 0 | 0 | 0 | 250 | 30 |
| Step 2 (SiOx) | 24 | 160 | 225 | 0 | 0 | 108 |
| Step 2 (SiONx) | 24 | 155-0 | 225 | 50 | 0 | 116-300 |
| Step 3 | 0 | 0 | 0 | 0 | 250 | 30 |

TABLE 3

RMM and RBM calculations of coating chemical structure according to EDS compositional data Integrated peak area ratios for peak a to peak b in SiL$_{2, 3}$-edge of Si$_3$N$_4$, SiO$_2$, and four sample coating. RMM validated for high-nitrogen type chemistries and RBM validated for high oxygen content chemistries

| Sample | EDS comp. (at. %) | | | XANES Si L$_{2,3}$ edge | Theoretical RMM (at %) | | | Theoretical RMB (Si$_z$O$_x$N$_y$) | | | Revised RMM (at. %) | | | Revised RBM (Si$_z$O$_x$N$_y$) | | |
|---|---|---|---|---|---|---|---|---|---|---|---|---|---|---|---|---|
| | Si | O | N | a:b | SiO$_2$ | a-Si | Si$_3$N$_4$ | z | x | y | SiO$_2$ | a-Si | Si$_3$N$_4$ | z | x | y |
| 1 | 51.1 | 3.6 | 45.4 | 1.72 | 5.2 | 15.5 | 79.3 | 2.04 | .014 | 1.81 | 5.2 | 15.5 | 79.3 | | | |
| 2 | 50.6 | 19.1 | 30.2 | 1.70 | 28.6 | 19.4 | 52.0 | 2.03 | .077 | 1.21 | 28.6 | 19.4 | 52.0 | | | |
| 3 | 51.0 | 27.0 | 22.0 | 1.20 | 40.7 | 20.4 | 38.9 | 2.03 | 1.08 | .89 | 40.7 | 20.4 | 38.9 | | | |
| 4 | 52.5 | 35.1 | 12.3 | 1.15 | 52.7 | 25.8 | 21.5 | 2.10 | 1.41 | .49 | | | | 2.10 | 1.41 | .49 |
| 5 | 51.5 | 43.5 | 5.0 | | 65.3 | 26.1 | 8.6 | 2.06 | 1.74 | .20 | | | | 2.06 | 1.74 | .20 |
| SiO$_2$ | 32.2 | 67.8 | 0.0 | 1.02 | | | | | | | | | | | | |
| Si$_3$N$_4$ | 43.8 | 0.8 | 45.3 | 1.73 | | | | | | | | | | | | |

Short Explanation of Steps:

Before starting, the chuck (lower electrode) was uniformly heated to 400° C. and allowed to equilibrate for 30 minutes. The chamber pressure was held constant for all processing steps and all chemistries at 900 mTorr. The RF used was 13.56 MHz. The ICP power for all depositions (Step 2) was 75 W and the RIE power for all deposition steps was 30 W.

Step 1: Chamber/Line Purge with Argon; Step 2: Deposition: 100 nm of coating, SiOx: 555.5 Å/min, SiONx: 517.2-200.0 Å/min; Step 3: Chamber/Line Purge with Argon.

Preoperative Animal Surgical Preparation:

The surgery site was prepared using the below tools, supplies and equipment: Autoclaved sterile surgical tools, Sterile saline filled in 30 ml syringe, Cotton swab, 2×2 sterile sponges, Scalpel blades, Bur tip #1 or #2, Suture needles, Syringes, Painkiller/sedative medicine (300-400 gram rat give 100-120 microliters of nalbuphine, Electrical clippers.

The supplies for isoflurane and oxygen gas were sufficient for the surgery. The valve for the isoflurane gas was confirmed to be going to the induction chamber. The heating lamp was turned on to provide heat to the animal during recovery for first few hours. The rat was placed into the induction chamber and anesthetize with 5% isoflurane in oxygen for about 2-3 minutes (when its breathing speed drops to about half). Air flow should be about 4-5 liters per minute.

The rat was then removed from the induction chamber, and electrical clippers used to shave the rat from the caudal end of the skull to the bridge between the eyes. The rat was then placed place into the induction chamber for another 1 minute.

The valve was turned on so as to provide the isoflurane gas going to the mask on the stereotaxic and not to the induction chamber. The rat's head was then placed in the ear bars. The head was held stable by properly inserting the ear bars in the animal's ears. Once the head is flat and perpendicular to the ear bars (and you cannot wiggle the nose—the upper teeth (incisors) of the rat were placed in the front metal piece. The gas mask was then placed over the animal's nose. Two small lamps were used to provide focused light and adequate heat during surgery. A pulse oximeter/heart rate monitor clip was placed on the animal's foot, and Lacrilube was applied to each eye. The isoflurane was turned to 2-3% through the mask to keep the animal anesthetized during surgery. The animal's heart rate was monitored throughout the surgery. Isofluran was turned down when the heart rate dropped to 30% from the initial reading, and turned down if the animal started to move.

Operative Procedure:

using the scalpel blade (#15), an incision was made by placing the blade between the eyes and making an incision about 1.5 cm long (FIG. 13). After about 1 cm, the skin and periosteum were divided without cutting the thick layer of muscle in the back part of calvarium so as to avoid heavy bleeding.

The periosteum layer was scratched using another scalpel blade to expose the underlying bone/skull. Sterile saline and 2×2 sponges were used to irrigate and clean the incision site. The skull and sides (away from sagittal midline) were scratched hard as part of the procedure so as to remove the periosteum layer. After iterative cleaning of the exposed skull with saline and 2×2 sponges, the exposed skull cite was dried with an air gun. Excess bleeding was controlled using a sterile cotton swab held in place for several minutes.

Figure 13A:
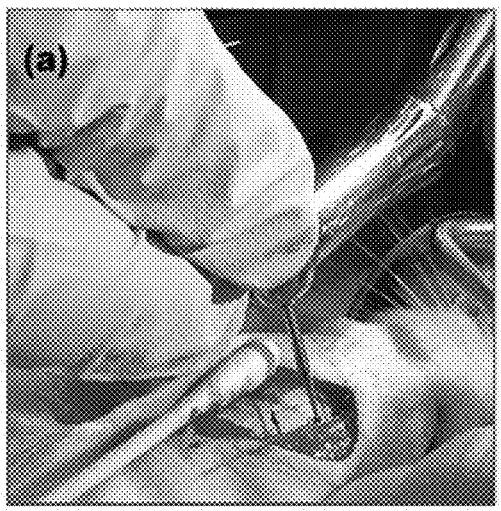
FIG. 13A demonstrates the use of a dental bur to make the precise defect for the study.
Figure 13B:
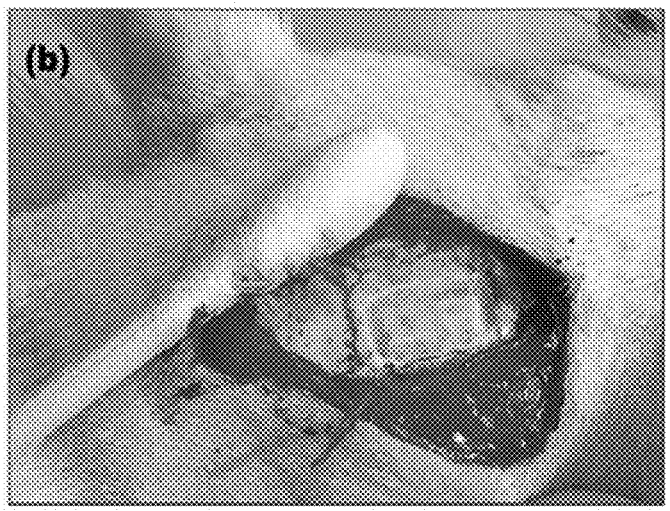
FIG. 13B illustrates the Reddish boundary edges that indicate proximity to the underlying dura.

A sterilized implant/Si chip (3 mm×5 mm) was implanted in the skull, and a boundary marked with a marker on dry skull. A dental bur (#1 or #2), having an about 0.5 mm diameter tip, was used to precisely cut the bone along the drawn boundary to create the critical calvarial defect (FIG. 13A). Care was taken so as to avoid the underlying dura, and to avoid excessive bleeding, as well as to allow the dura to perform its normal function in bone healing. Upon closing the dura, the drilled boundary edges will get reddish (FIG. 13B) and generally corners of the marked boundaries are the last to get detached.

Tweezers were used to lift up the bone after it is completely cut. At this point or even before, blood should be washed away using sterile saline and 2×2 sponges, followed by immediate blow dry using air gun. In case of nicking the dura, pressure should be applied with 2×2 sponges to stop bleeding. The air gun can be used to help stop bleeding in addition to making the dura dry.

Figure 14:
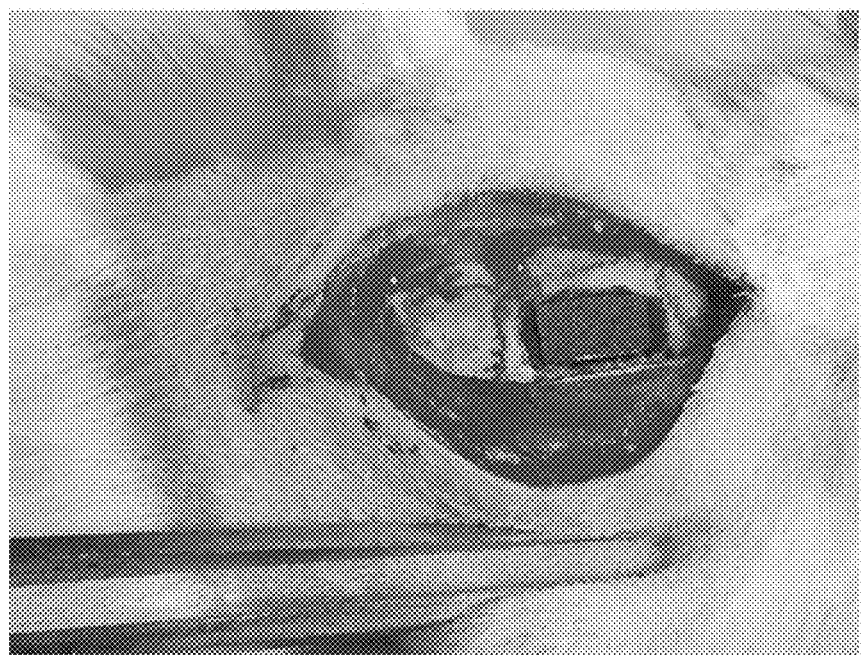
FIG. 14 shows the implanted chip with treated surface (coated surface) glued to the dura in the animal.

Using a micropipette, a small (~1-2 μl) drop of gel glue was placed in the middle of the polished coated surface of the implant. The implant was then placed upside down in the defect so that it became securely glued to the dura (FIG. 14). The skin was then sutured using 3-0 monofilament taper point suture needle. The sutures were placed close enough to allow the skin heal (typically 5 sutures).

Post-Operative Procedure:

After completion of the surgery, 0.1-0.12 ml of painkiller/sedative nalbuphine is injected intramuscularly into the animal using a 1 ml syringe, and the animal's head and surgery site is thoroughly cleaned using sterile saline and 2×2 sponges. The rat was then transferred to the warmed (using heating lamp) chamber with paper bedding, and allowed to recover for a few hours in the warm chamber. After a few hours, when the animal showed purposeful movement, the animal was transferred back to the animal resource unit (ARU) and housed singly. After about 4 hours of surgery, the rat was given another dose of painkiller (0.07 ml or 70 microliters nalbuphine) subcutaneously using 1 ml syringe.

The behavior of the animal was observed for any signs of pain/distress, walking patterns, food intake and any signs of dehydration. Pain killer nalbuphine 0.05 ml was administered when needed twice a day for the following two to three days. The sutures were removed after about three days, and the wound site was monitored.

Figure 15A:
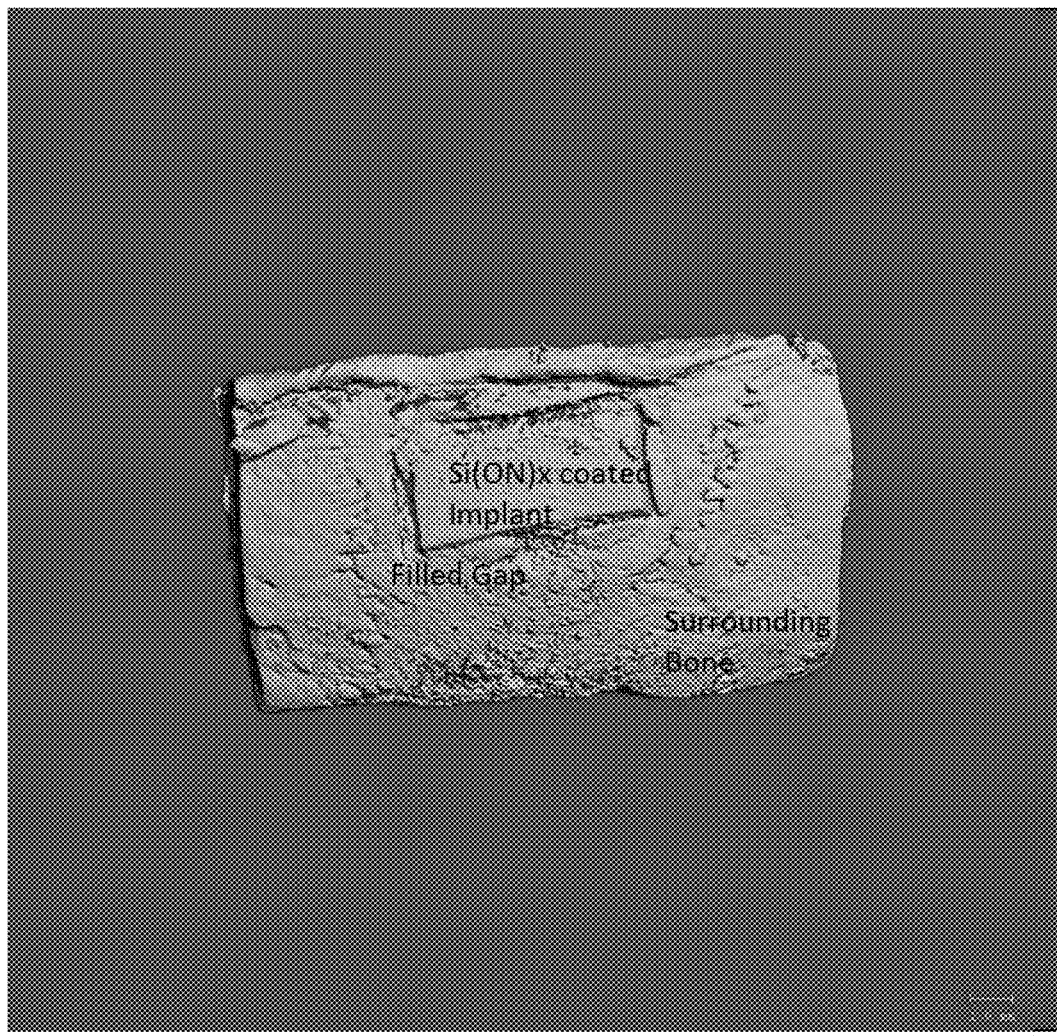
FIG. 15A illustrates a microcomputed x-ray tomography image of rat calvarial gap filled in by fully dense bone around Si(ON)x coated biomedical device material implant within surrounding calvarial bone. Gray color indicates dense calcified bony tissue, blue represents porous space. The upper perimeter is the occipital bony ridge while the lower perimeter of the sample is near the midline suture. Healing occurs primary at the occipital bony ridge, indicating intramembranous ossification due to the lack of chondrocytes present at this location.
Figure 15B:
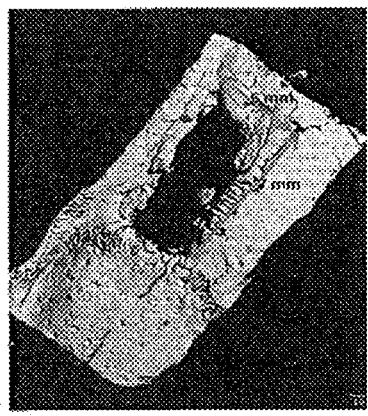
FIG. 15B shows calvarial defect without any intervention does not heal.
Figure 15C:
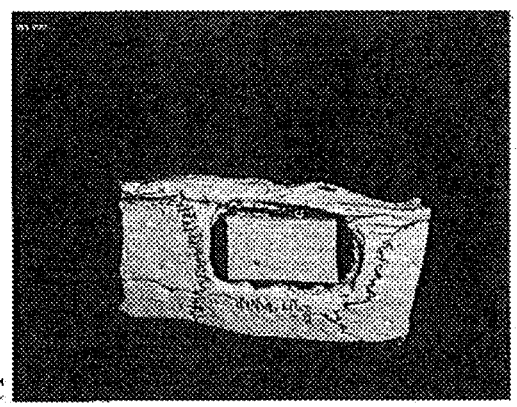
FIG. 15C shows the intervention by uncoated device (Si wafer, no SiONx coating) does not induce healing and had an observed inflammatory response that was pervasive over the 5 week time period of study.

Results:

The in vivo results from this study are presented at FIG. 15. The figure presents a microcomputed x-ray tomography image of the rat calvarial gap that was filled in by fully dense bone around the amorphous Si(ON)x coated surface of the biomedical device implant within the surrounding calvarial bone. The gray coloring observed in the x-ray tomography image demonstrates the presence of dense calcified bony tissue, and the blue color observed demonstrated porous space. The upper perimeter of the x-ray tomography image is the occipital bony ridge, while the lower perimeter of the image is near the midline suture. Healing is demonstrated to have occurred primary at the occipital bony ridge, thus providing evidence of intramembranous ossification, as chondrocytes are lacking at this location of the implant structure in vivo.

Prophetic Example 10—Resorbable, Bio-Inspired Medical Devices and Coatings; Use of Free Si4+ Ion for Accelerating Bone Healing The present example demonstrates the utility of the present invention for providing a resorbable device having structural and antioxidant support for bone healing. The devices include a thin film and/or nanofilm layer of an amorphous silicon containing material, and provides for the control of bone formation.

CVD/Lithography:

CVD/lithography will be developed for Si(ON)x-modified devices to include clinically-relevant geometries that selectively bind osteoblasts for bone healing. CVD/lithography will be developed to modify porous 3D polymer/composite networks with Si—O—N—P-based chemistries and hierarchal nano-/micro-patterns. These devices will be studied for their effect on osteoblast and inflammatory cell adhesion and gene expression. Devices will be developed that preferentially bind osteoblasts and reject inflammatory cells for bone healing.

Amorphous Si(ON)x in Ischemic Necrosis:

The effect of amorphous Si(ON)x in an ischemic necrosis animal model will be examined. In this model, inflammation and osteogenesis need balancing by ROS regulation. The femoral head will be ligatured in rats to induce osteonecrosis. Osteonecrosis will be perpetuated because ROS activity will remain high. The devices described above will be used to determine their effect on ROS activity. The goal will be to optimize device properties that reduce ROS activity and limit the perpetuation of the necrosis and initiate osteogenesis.

Example 11—Use of Si4+ for Accelerating Bone Healing

It is envisioned that bone healing and bone regeneration may be enhanced employing the teachings of the present invention by providing a source of Si4+ to a population of cells comprising osteoblasts and/or osteoblast progenitor cells in a bone-promoting physiological environment. For example, such a bone-promoting physiological environment may comprise an in vivo tissue site where an implantable device has been positioned, such as at a bone fracture site. Alternatively, a bone-promoting physiological environment may comprise an in vitro environment, such as a tissue bioreactor into which a population of cells comprising osteoblasts are present.

Injected Si4+:

The effect of Si4+ to heal bone in an ovariectomized animal model (mouse), where osteoporotic fracture healing requires antioxidant support, will be examined A compromised oxidative environment will be induced in the ovariectomized mouse model, and Si4+ will be administered as micro-injected amorphous silica particles (Si—O—N—P) into a small defect site. The injection dose effect will be studied by examining serum H2O2/SOD1/OCN content and bone density. The complete particle degradation of the injected Si4+ and an accelerated bone defect healing/union will constitute the end points for this study, and provide demonstration of Si4+ as a treatment preparation useful in accelerating the bone healing process.

Example 12—Enhanced Interfacial Adhesion and Osteogenesis for Rapid "Bone-Like" Biomineralization by PECVD-Based Silicon Oxynitride Overlays The present example is provided to demonstrate the utility of the invention for enhancing adhesion of bone-generating cells to a metal surface that has been treated using a low-temperature PECVD amorphous silica film. "N" incorporation to an underlying metal surface with PECVD is demonstrated to enhance osteogenesis and rapid biomineralization to the treated metal surface, and hence provides improved implant devices with more rapid healing and bone restorative properties in vivo.

To demonstrate the above properties and advantages, two confluent studies are presented. First, a simulated SiOx-Ti/TiO$_2$ interface was fabricated and its chemical and mechanical properties were investigated to assess interfacial congruity. Si wafers were coated with Ti, followed by optical lithography and plasma etching to define patterns in Ti layer, baked to grow a thin TiO$_2$ layer, and then deposited PECVD-based SiOx overlay. The Ti—TiO$_2$—SiOx interface was then extracted using SEM-FIB and imaged using TEM. Milling XPS was used to determine elemental composition through the interface and initial functional group formation after processing. Nanoscale scratch testing was used to determine interfacial adhesion.

In the second part of this study, in vitro properties of the amorphous silica-based overlays with varying levels of nitrogen doping were demonstrated to provide an osteogenic effect. Samples of SiOx, Si(ON)x, and SiNx coatings were overlaid onto Si substrates by PECVD. No Ti was added so that the effect of varying the chemistry was studied solely when compared to control samples having no Ti involved. Glass cover slips were used as a control material for cell-free and cell culture in vitro testing as they do not degrade and have been previously established as an adequate control for cell culture studies (83, 84). Cell-free immersion testing was conducted to determine in vitro degradation behavior using Raman Spectroscopy, contact angle measurements, optical and scanning electron microscopy. Cell culture studies were carried out using the human periosteal cells, which are considered as osteoprogenitor cells since they undergo osteogenic differentiation upon the addition of ascorbic acid and have similar osteogenic markers as osteoblasts (86) and are often assayed for relative gene expression and biomineralization using qPCR, Raman spectroscopy, and optical and scanning electron microscopy.

Figure 16:
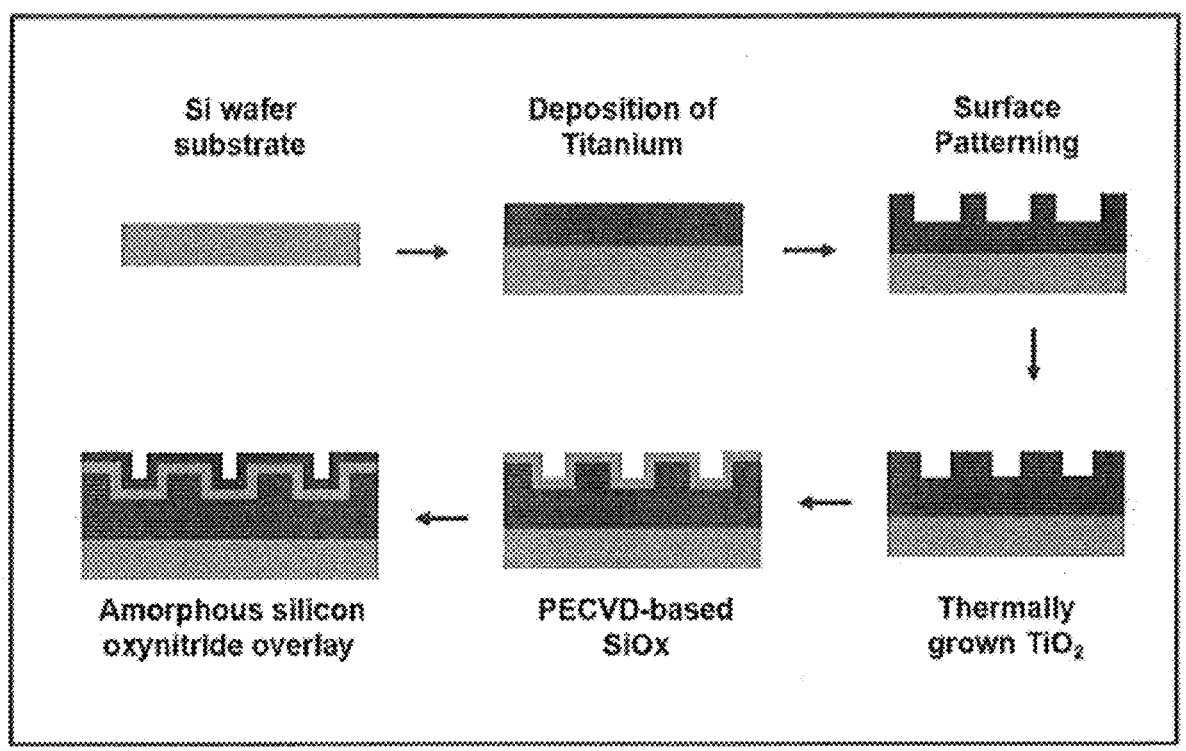
FIG. 16. Process flow for the fabrication of Si(ON)x overlays A schematic diagram to illustrate the fabrication process for PECVD amorphous silica-based overlays on Ti with Si wafer substrate.

Device Fabrication:

To create the Ti/TiO$_2$—SiOx devices and Si(ON)x overlays, the processes used were tailored around rapid prototyping of various deposition, etching, and analysis techniques. FIG. 16 shows a schematic diagram to demonstrate the step-by-step fabrication process. The fabrication process started with standard cleaning of single crystal Si wafers, which were used as the base substrate. The cleaning process started with immersion of Si wafers in piranha solution (3H$_2$SO$_4$:1H$_2$O$_2$) at 95° C. for 10 min followed by rinsing in DI water. This process removed any dust particles and photoresist residues. The wafers were then immersed in NH$_4$OH, H$_2$O$_2$ and DI water mixed in 1:1:10 respectively for 5-10 minutes at 70° C. This process removed any organic film and metal residues. Next, the wafer were cleaned in a solution of HCL, H$_2$O$_2$ and DI water mixed in 1:1:10 respectively for 5-10 minutes at 80° C. in order to get rid of atomic and ionic contaminants. Finally, the wafers were dipped in buffered hydrofluoric acid (BHF) for about 60 sec to remove any native oxide layer. The wafers were then rinsed in DI water followed by nitrogen gas to blow them dry. The wafer were dehydrated for 5 minutes at 200° C. and allowed to cool down for 1-2 minutes before proceeding to the next step of Ti deposition. Ti layers are then deposited using electron-beam physical vapor deposition (EB-PVD) system. Photolithography and reactive ion etching (RIE) were deployed for patterning Ti layer to create the desired trench size for cellular studies at a later stage. Thermal oxidation was then employed to create sufficient layer thickness of TiO$_2$ to anchor overlays. PECVD of amorphous silica-based overlays was then conducted to build SiOx/Si(ON)x overlays onto structured Ti/TiO$_2$ surfaces.

Deposition of Ti Using e-Beam Physical Vapor Deposition (EB-PVD) System:

To deposit a uniform layer of Ti on Si wafer, electron-beam physical vapor deposition system was used. A Ti metal target was used as the Ti source, which was bombarded with the electron beam under high vacuum. The electron beam excited the target and evaporated Ti atoms. These vapors deposited as columnar grains on the Si wafer placed in the vacuum chamber. The emission current was used to control the deposition rate. The deposition was carried out at 1 angstrom/sec at an emission current of 3.1 mA and chamber pressure of $5\times10^{-8}$ Torr to deposit a 300 nm thick layer of Ti.

Surface Patterning:

The surface of the Ti layer was patterned to have a well-thought textured topography to promote cell migration and extracellular matrix attachment. The surface pattern was carried out through a series of sequential procedures that include mask writing, followed by photolithography and dry etching using RIE process.

Mask Writing:

Masks for contact photolithography were prepared using a laser mask writer (Heidelberg DWL 66 Direct Write Lithography Tool). A computer-aided design of the desired pattern was developed using AutoCAD software. Using the mask writer, the pattern was then transferred to a photoresist and Cr coated 5×5 inch$^2$ glass substrate with 2.4 mm thickness. Mask writing was completed over 36 hours.

Photolithography:

Contact photolithography was used to transfer the mask pattern into a thin photoresist film deposited onto a p-type, (100) orientation, single-side polished silicon wafer of 4-inch diameter and 500 µM thickness. Negative photoresist SU-8 2000 (MicroChem, MA) was applied to the 4-inch wafer with Ti film by using a spin coater. The wafer was properly centered in the middle and the photoresist was spin coated at 3000 rpm for 30 sec to have a uniform layer of resist. Microprime MP-P20 liquid HMDS (Shin-Etsu MicroSi Inc., AZ) was used as an adhesion promoter between the photoresist and the substrate surface. Application of each primer and the resist was done in the center of the spinning wafer in a fluid motion using an eye-dropper without satellite droplets. The wafer with primer and resist coating was baked at 90° C. for 90 seconds and allowed to cool down for 60 sec. The wafer was then exposed to UV light using Quintel Q4000 Mask Aligner (Quintel Contact Lithography Tool). The mask was placed first on the mask vacuum chuck against the banking pins with chrome side facing down. Mask vacuum was turned on to hold the mask and wafer was exposed for 8 sec in contact mode. A post exposure bake at 115° C. for 60 sec was carried out followed by 1 min cool down cycle. The wafer was subsequently submerged in the SU-8 developer for 60-90 sec to get the pattern in photoresist. The wafer was rinsed in DI water and blown dry under nitrogen gun. The wafer was descumed for 20 sec in 0$_2$ plasma using oxford RIB systems (TePla) followed by an aggressive descum cycle at low pressure for 30 sec to get a clean patterned wafer.

Reactive Ion Etching (RIE):

After photolithography, the exposed Ti film was etched using RIE process in order to transfer the photoresist patterns to the underlying Ti film. The Si wafer was placed into the etching chamber and the system was allowed to pump down to its base pressure (0.5-1.0×10 Torr). RIE was performed using an Oxford Plasmalab 100 RIE/ICP Etcher for metal etching (Oxford Instruments, UK). Within the Oxford RIE system, a Ti etching protocol using chlorine gas plasma was selected. Etch time ranged from 15-60 seconds for an etch rate of about 100 nm/min. The plasma intensity was static for the time period of etch and reached a pressure of $5\times10^{-6}$ Torr when finished. The photoresist was removed completely by immersing in acetone and followed by piranha clean. The wafer was rinsed in DI water and dried under nitrogen. Metal films on Si-wafer substrates were then baked in air at 250° C. overnight for thermal oxidation of Ti to have a conformal oxide layer of TiO$_2$ on the patterned surface.

Deposition of Amorphous Silica-Based Overlays Using PECVD:

Plasma enhanced chemical vapor deposition (Oxford Plasmalab Systems 100 PECVD) of amorphous silica-based overlays was carried out in three steps. First, a conditioning step was used to prepare the chamber for the chemistries being used for the following deposition step. Next, the deposition of the desired chemistry was overlaid onto the wafer surface. Finally, a cleaning step was employed to prepare the PECVD system for future runs. For deposition, silane (SiH4) was used as the Si source, N$_2$O was used as the oxygen source, and N$_2$/NH$_3$ was used as a controlled N source. A standard protocol for SiOx and SiNx deposition from the Oxford PECVD system was initially selected. To vary O/N ratio in the film, the O$_2$, N$_2$, and NH$_3$ flow rates were adjusted. The optimized settings result in a lower deposition rate (64 nm/min) but conformal and higher quality films Therefore, deposition would run approximately 90 seconds for a film thickness of about 100 nm. Deposition temperature was maintained at 350° C. throughout the deposition process. Pressure was maintained at 900 mTorr. Radio frequency power was maintained at 20-60 W. PECVD of Si—O—N films is tunable for film stress by use of dual (low and high) radio frequency for plasma excitation (68). Plain samples (no patterns) with amorphous silica-based overlays were also fabricated for chemical and mechanical characterization of the overlays and for their use as control surfaces to study the impact of surface topography on cells behavior.

In-Process Thin Film Characterization:

Characterization of samples during fabrication process was carried out at the CNMS facility at Oak Ridge National Laboratory (ORNL). These facilities were used to confirm and assess device structural, chemical, and mechanical properties as sample devices were fabricated. A spectroscopic ellipsometer (JA Woollam M-2000U) was used to determine the thickness and refractive index of PECVD multi-layered structures. An optical microscope (Leica DM4500P) was used for bright field transmission or reflected analysis of in-process samples to determine surface cleanliness between process steps and etch conformality and artifacts from etching processes. Film stress analysis was performed using FSM 128 film stress measurement system (Frontier Semiconductor). A Veeco optical profilometer was used to measure etch depth before and after etch process steps.

After samples were prepared, a standard dicing saw was used to make 1 cm×1 cm sections for post-process characterization and in vitro testing.

Scanning Electron Microscopy (SEM):

SEM analysis was conducted using two different SEM machines. For in-process characterization during sample fabrication, an SEM with capability of loading 4-inch wafer samples was desired so FEI Novalab 600 Dual-beam (electron/ion) system at ORNL was used for in-process imaging/analysis. For post-process characterization and in vitro testing, a JEOL 6010LA SEM was used to examine the small section samples. Both the SEMs were operated at 5-15 KV energy to get finest results.

Transmission Electron Microscopy:

TEM facilities were provided through the SHARE program in the High Temperature Materials Laboratory (HTML) at ORNL. Samples after fabrication were sectioned using a Hitachi NB5000 Dual-beam scanning electron microscope focused ion beam (SEM-FIB) onto Cu grids prior to imaging by TEM. TEM imaging was carried out using a Hitachi HF-3300 300 kV FEG TEM/STEM with electron energy loss spectroscopy (EELS) for in-situ x-ray diffraction analysis.

X-Ray Photoelectron Spectroscopy (XPS):

XPS facilities were also provided through the SHARE program at the HTML at ORNL. XPS analysis was conducted using a Thermo Scientific K-Alpha XPS with capabilities for sample through-thickness milling. This type of analysis can aid in getting surface and interfacial elemental chemical characterization.

Nanoscratch Testing:

Adhesion of the PECVD-based amorphous silica overlays with the underlying metal/metal-oxide was determined through a nanomechanical scratch test on the sample surface. The adhesion/miscibility of overlays with Ti/$TiO_2$ was gauged by evaluating the friction/wear of the interfacial layers. An incremental load of (0-5000 µN) was applied to make a 10 µm long horizontal scratch on the sample surface using a cube-corner tip with the nano-indenter (Hysitron Ubi®1 Nano-Indenter) and the change is resistance offered by interfacial layers as the tip goes deeper and deeper with increasing load, was used to gauge the adhesion strength of the film.

X-Ray Absorbance Near Edge Structure (XANES) Spectroscopy:

XANES spectroscopy was conducted at the Canadian Light Source on the University of Saskatchewan in Saskatoon, Saskatchewan, Canada. XANES is an extremely useful and advanced tool to study poorly crystalline or amorphous phases of bioceramics and investigate the local coordination of atoms and find their valence states (31, 32). The traditional characterization techniques (XRD, neutron diffraction, EDS) face challenges to analyze nanometer size crystalline particles or poorly crystallized structure of materials (32). Therefore, XANES was employed to investigate initial few nanometer layer of HCA. The phosphorous (P) L-edge spectra was probed using the Plane Grating Monochromator (PGM) beam-line was used to probe P L-edge spectra over the energy range of 130-155 eV. PGM operates at the low energy range between 5-250 eV, a step size of 0.1 eV and shutter opening of 50 µm×50 µm. The calcium (Ca) L-edge and oxygen (O) K-edge were characterized by Spherical Grating Monochromator (SGM) beam-line that operates in the midrange energy of 250-2000 eV with a step size of 0.15 eV and shutter opening of 100 µm×100 µm. The Ca L-edge and O K-edge spectra were recorded for energy ranges between 340-360 eV and 525-560 eV respectively. The spectra for all samples were acquired after exposure to in vitro immersion for 6 hours.

In Vitro Testing:

In vitro testing was accomplished by immersing sample devices in cell culture medium (alpha-Minimum Essential Medium, α-MEM, Invitrogen Inc., Carlsbad, Calif.). Samples were placed into 6-well plates and immersed in 2 mL of media. Glass cover slips were used as an insoluble control samples for these experiments. Immersion testing was studied over several days and samples were removed to determine various dissolution effects of in vitro conditions on surface properties Immersion studies were conducted under ambient pressure and 37° C. at 100% relative humidity using a standard incubator.

Cell Culture Study:

Human periosteal cells were used as an osteoblast progenitor. These cells were isolated from periosteum of femoral bone as described previously (33). These cells differentiate into osteoblast and express various osteogenic markers that include bone morphogenetic protein 2 (BMP2), lysyl oxidase (LOX) and Osterix (OSX) when cultured in osteogenic media consisting of 50 ppm ascorbic acid, 1% penicillin-streptomycin and 10% fetal bovine serum supplemented to α-MEM. They also form collagenous matrices and mineralized nodules after 3-4 weeks of incubation in vitro.

These cells were seeded (50,000 cells per sq. cm) onto control and test sample surfaces after prior 150 sq. cm flask cultures and expansion. The passage number of cells was maintained between 1 and 4 for all experiments. To determine the effect of sample surfaces on cells, gene expression studies were conducted. The samples were also tested for their long-term effect on collagen matrix formation and mineralized tissue analysis.

Gene-Expression Analysis:

Quantitative reverse transcriptase polymerase chain reaction (qRT-PCR) was used to quantify levels of gene expression (76). Cells were cultured on the test samples and the control surfaces for 3 days. The cells were lysed to extract the total RNA using the RNeasy Mini Kit (Qiagen, Valencia, Calif.). The extracts were transformed to cDNA using reverse transcriptase (Reverse Transcription System, Promega, Madison, Wis.) as per manufacturer's procedural guidelines. A full-spectrum UV/vis nanodrop volume analyzer (ND-1000, Nanodrop Technologies, Wilmington, Del.) was used to quantify the total RNA and the converted cDNA for each sample. Absorbance measurements of total RNA or total cDNA concentrations were performed at 260 nm (A260) while A260/280 was used to estimate the purity of nucleic acids. All the cDNA samples (including controls) were diluted to a matching concentration of 100 ng/μl.

The samples were examined for three different types of osteogenic genes (BMP2, LOX, OSX) using an internal housekeeping gene (glyceraldehyde 3-phosphate dehydrogenase, GAPDH) for relative quantification. To quantify PCR, 10 μl reaction was performed for all samples. For this, 1 μl of cDNA solution was mixed with 5 μl of FastStart Taqman Probe Master (Roche Applied Sciences, Mannheim, Germany), 0.5 μl of gene template and 3.5 μl of PCR grade water (Amgen Inc., South San Francisco, Calif.). Sample reaction was executed using a real-time PCR machine (ABI7500, Applied Biosystems Inc., Foster City, Calif.). Adequate plateau of the amplification ensured reliable threshold cycle ($C_T$) values, which were used to quantify relative gene expression using delta-delta $C_T$ ($\Delta$-$\Delta$-$C_T$) method.

Raman Spectroscopy:

Raman spectroscopy is a powerful technique to study biological samples like cells without involving lengthy procedures and need of cell lysis, staining or fixation but requires relatively high-power laser beam to overcome the inherent low Raman scattering efficiency of biological molecules (90, 91). Microspot Raman spectroscopy (DXR, Thermo Scientific) was used to map dehydrated samples after in vitro cell cultures on the sample surface for 28 days to study the impact of surface chemistry on mineral deposition (67). The spectroscope was operated at following conditions: 780 nm laser source, 150 mW power, 50 μm slit, 10 Å–objective, 10 s exposure. Thirty-two spectra per location were recorded between 400 and 2200 $cm^{-1}$. The presence of the carbonate (1072 $cm^{-1}$), phosphate (960 $cm^{-1}$) and hydroxyproline (876 $cm^{-1}$) bands of each averaged spectra was then recorded to compare mineral development in response to the surface effects of the test samples when compared to control samples.

Statistics:

For in vitro experiments, triplicate sampling with duplicate experiments were conducted for all experiments. Analysis of variance was used for statistical analysis with $p<0.05$ to determine statistical significance. For quantitative data taken on multiple samples of fabricated materials, error was nominally less than 1% and was therefore not reported.

Figure 17E:
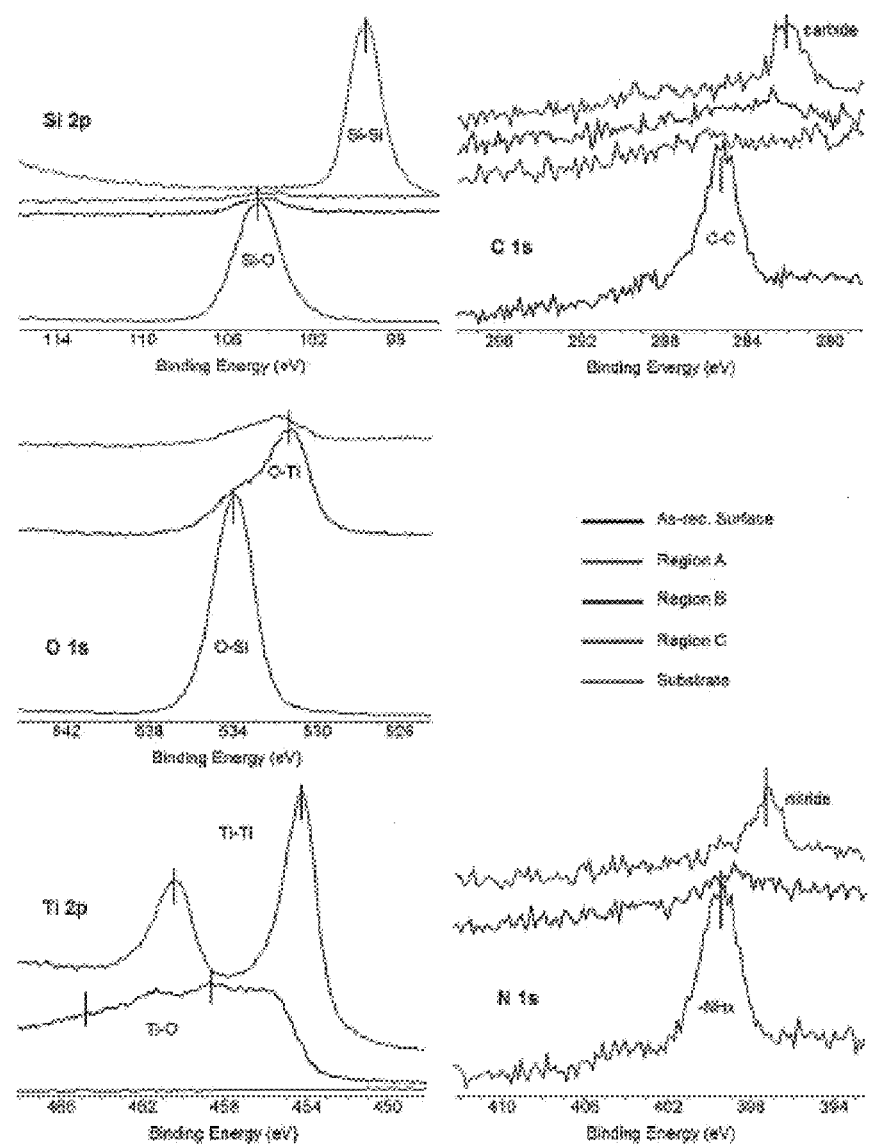

Device Fabrication and Characterization:

The TEM micrographs of the fabricated device used in this work are shown in FIG. 17. The image shows three regions fabricated on top of the Si-wafer substrate. Region 1 is the EB-PVD Ti layer, Region 2 is the thermally grown $TiO_2$ layer, and Region 3 is the PECVD-based SiOx layer. Ti layers were observed to have a columnar structure with average column width of about 100 nm, indicating line-of-sight deposition. Characterization using EELS analysis indicated the presence of anatase Ti (result not shown). Within the Ti layer, aligned columnar atom planes of Ti were observed, which indicates that the columnar microstructures were composed of these oriented atom planes (FIG. 17B).

At the top of the Ti layer, etching showed distinct etched regions spaced 2 micrometers apart from each other. Sidewalls exhibited some curvature indicating certain isotropy to the etch profile using cryogenic Cl gas. An induction period of 15 seconds was observed and a steady post-induction etch rate of about 100 nm/min was recorded for all the samples. Within a sample, the etch depth for all etched trenches was found to be highly uniform.

The natively grown $TiO_2$ was overlaid with a PECVD silica layer. PECVD overlays were found to be contoured with the underlying etched surface, however, some rounding of sidewalls did occur. The interface between the PECVD overlay and underlying Ti/$TiO_2$ was observed to have a gradual transition with microstructural features distinct for each region and a less distinctive microstructure between regions (FIG. 17C).

Figure 17F:
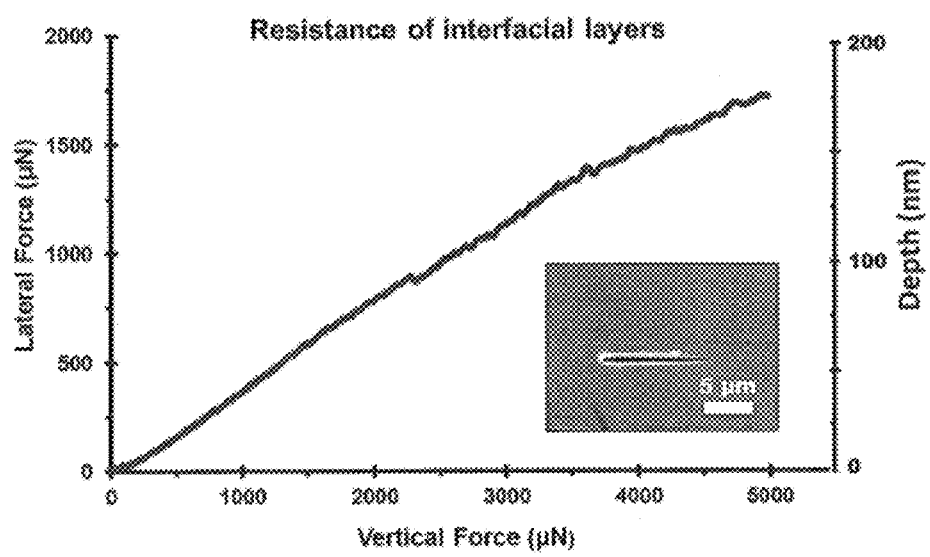

Results from XPS analysis (FIG. 2d) were obtained by milling through the thickness of the device. The data showed elemental composition from the surface of PECVD silica (Region 3, FIG. 17A) to the Si wafer substrate. The XPS results confirmed the overlay thickness of PECVD SiOx to be approximately 100 nm, 300 nm of Ti layer, and a graded interface between the SiOx overlay and $TiO_2$ layers. This graded interface exhibits that atomic % composition of oxygen is nearly two times higher than that of Si or Ti at the interface. It means for every Si atom, there are 2 oxygen atoms and likewise every Ti atom is bonded to 2 oxygen atoms that denotes near stoichiometric $SiO_2$—$TiO_2$ interface, indicating that the silica and Titania layers formed ionic bonding between the two layers. The $TiO_2$ layer was distinct and had a thickness of approximately 10 nm, however, data for oxygen diffusion within the Ti layer (O—Ti) showed some oxygen diffused into the Ti layer. This is likely due to O diffusion along the columnar grain boundaries (36). Potential contamination of N and C during PECVD was insignificant due to the additional air plasma-cleaning step in our fabrication process. Without plasma-cleaning, N and C can be as high as 10 and 14 at. %, respectively (93). Nanoscratch testing showed no significant change in resistance when the $SiO_2$—$TiO_2$—Ti interface was scratched through, which indicated adequate miscibility of the interfacial layers (FIG. 17F).

In vitro Testing of Nanofabricated Devices:

Cell-free in vitro testing was conducted to determine the effect of in vitro conditions on PECVD silica surfaces. In this study, nitrogen was incorporated into amorphous silica overlays to determine the effect on N substitution of O on surface chemistry during in vitro immersion. Ti layers were not used to isolate the effect of in vitro conditions on amorphous silica-based material chemistry and compare these with control glass surfaces.

Figure 18:
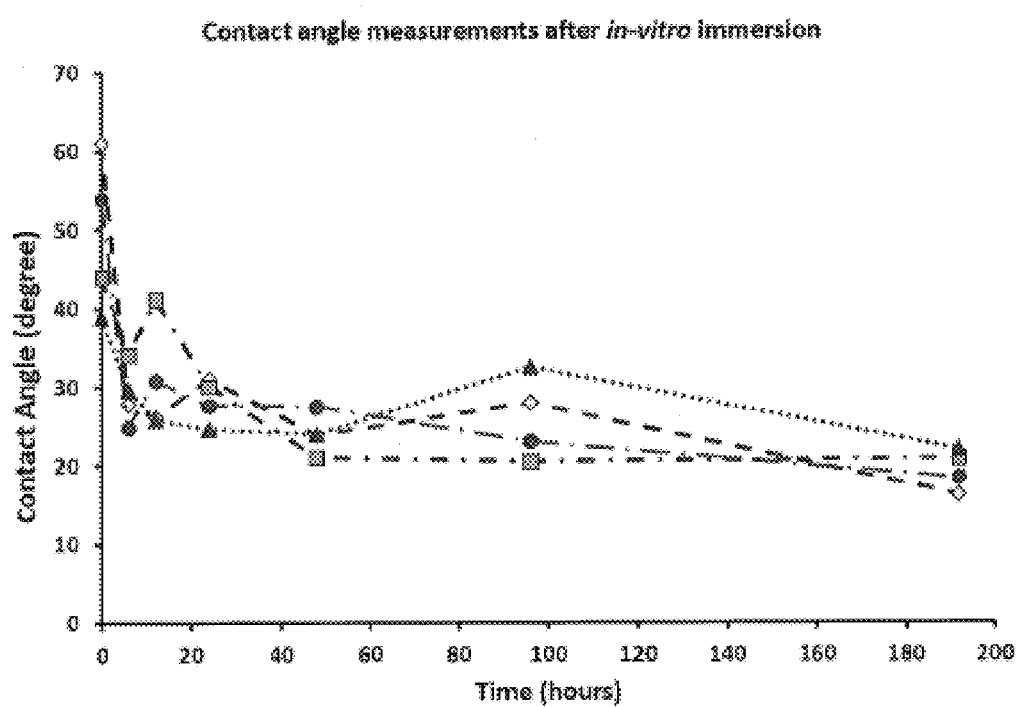
FIG. 18. Contact angle measurements PECVD-based SiNx with n=2.0 (◇), SiOx with n-=1.45 (-▲-), Si(ON)x with n=1.82 (-●-), and Si(ON)x with n=1.57 (-□-) (surfaces after in vitro immersion indicated hydrophilic functional group inductions in surface properties when submerged in vitro.

The effects of in vitro conditions on SiOx, Si(ON)x, and SiNx surface contact angles are demonstrated in FIG. 18. Initially, SiOx layers had a lower contact angle, indicating their initial relative hydrophilicity. On the other hand, the SiNx layers exhibited relatively high contact angle and indicated their relative hydrophobicity. After a few hours, the contact angle decreased for all samples and was approximately the same after 24 hours. This change in contact angle with time indicated that these surfaces experienced hydrophilic functional group changes during in vitro submersion.

The results from XANES data were analyzed to illustrate the effect of in vitro conditions on surface elements present on the PECVD SiOx, Si(ON)x, and SiNx overlays. XANES data (FIG. 19) showed that after 6 hours of in vitro immersion, Ca was present in relatively large abundance on the surface of all tested materials (except the control surface). XANES data analysis also confirmed the presence of P species on all surfaces as well (FIG. 19B). However, the presence of noise in the peaks indicates that the formation of the Ca—P-based species may be amorphous rather than crystalline in nature.

Although all materials tested showed the presence of Ca and P on their surfaces, differences were observed when analyzing the coordination of O on these surfaces (FIG. 19C). The results of XANES data on the coordination of oxygen revealed that O coordination exhibited a pattern indicating the presence of hydroxyapatite. As the N content increased (and thus substituting for O), the presence of O peaks coordinated in a carbonate structure appeared with increasing intensity relative to the peak showing O coordinated into a phosphate structure. This coupled formation of carbonate and phosphate near edge structures indicates the presence of hydroxycarbonate apatite. An interesting trend was also observed with increasing carbonate to phosphate ratio as the N/O ratio increased in the overlay.

Figure 20A:
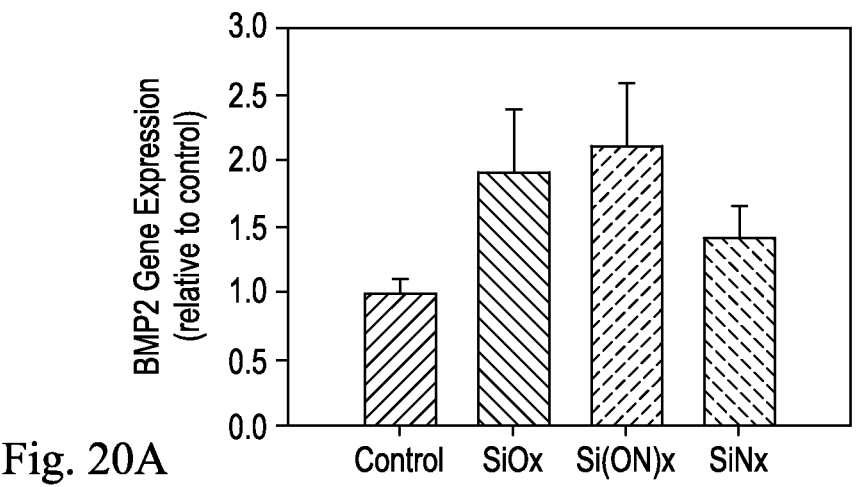
FIG. 20A-FIG. 20C. Human periosteal cells osteogenic gene expression data for (FIG. 20A) BMP2, (FIG. 20B) LOX and (FIG. 20C) OSX after 3 days in culture shows many-fold enhanced expression of these osteogenic markers (ANOVA, * indicates statistical significance, p<0.05).
Figure 20B:
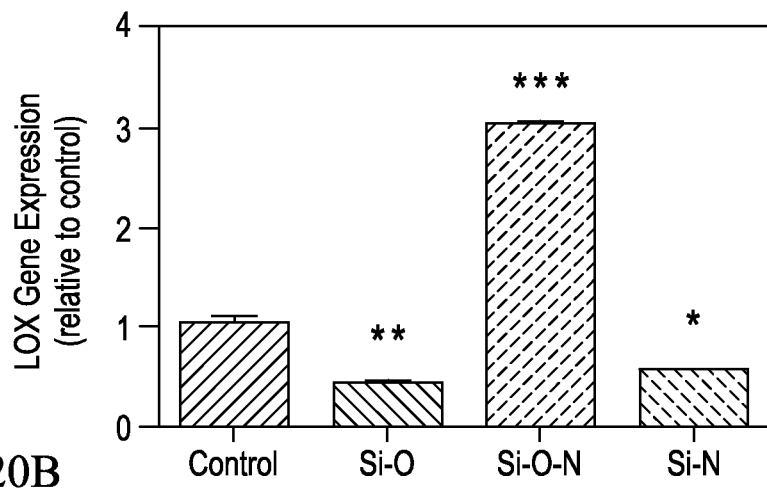
Figure 20C:
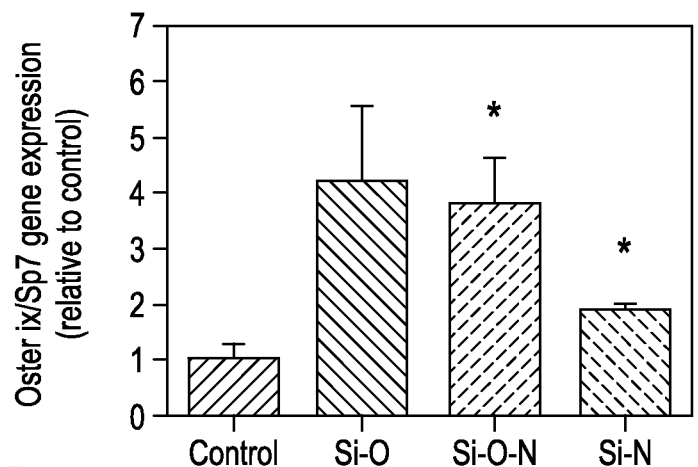

Cell Cultures studies of Nanofabricated Devices:

These materials were also tested for osteogenic properties in vitro using human periosteal cells. Gene expression of osteoblast markers, extracellular matrix collagen production and mineralized nodule formation were studied. Cells were cultured for 3 days to determine the effect of surfaces on gene expression, 6 days for ECM collagen formation, and 4 weeks for mineralized nodule formation. FIG. 20 shows the results for relative expression of osteogenic gene markers. All surfaces were observed to enhance BMP2 and OSX expression to levels 2-4 folds higher than control surfaces. However, maximal enhancement of these markers occurred on Si(ON)x surfaces. All the samples were statistically different from each other with a p-value of $p<0.05$ (ANOVA).

Figure 21A:
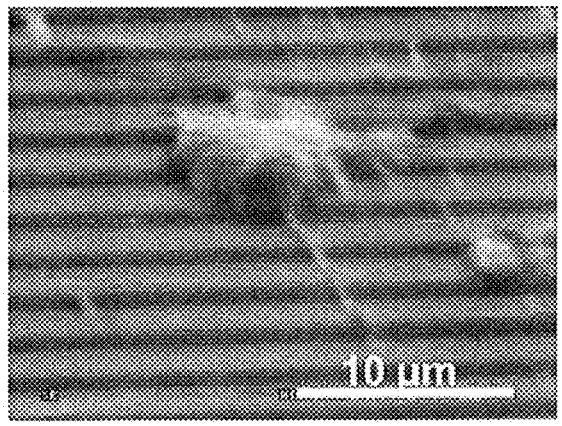
FIG. 21A-FIG. 21C. SEM micrographs compare extracellular matrix (ECM) collagen production by human periosteal cells after 6 days in culture for (FIG. 21A) SiOx, (FIG. 21B) Si(ON)x and (FIG. 21C) SiNx overlays.
Figure 21B:
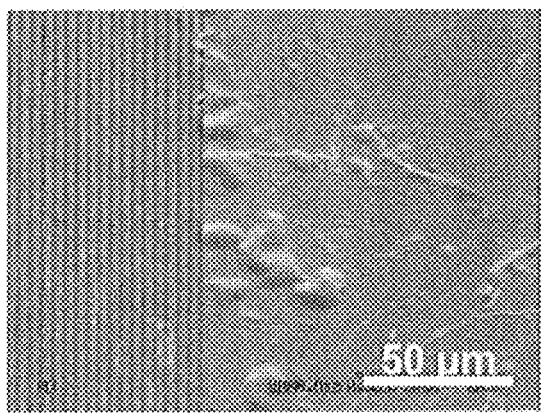
Figure 21C:
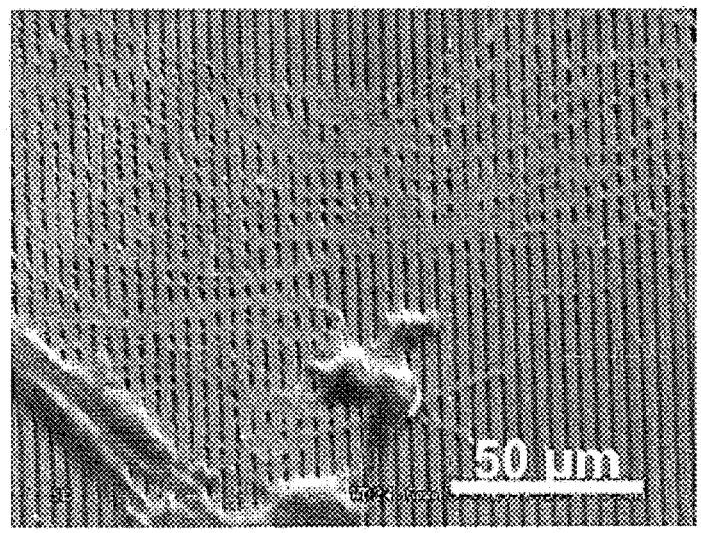
Figure 22A:
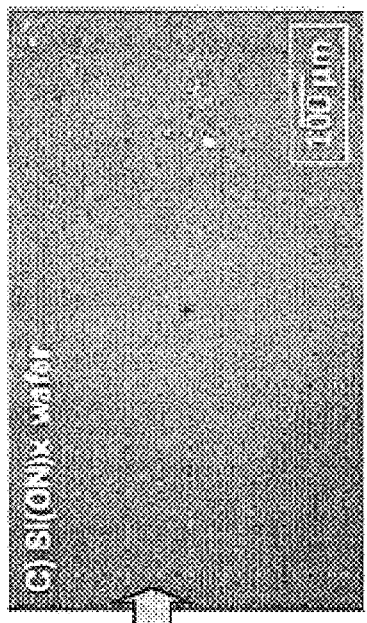
FIG. 22A-FIG. 22E. Analysis of ECM after 4 weeks of in vitro human periosteal cell culture Raman spectroscopy showed initial layers of silica for Control (FIG. 22A), Si(ON)x surfaces (FIG. 22B), and Si(ONOx wafer (FIG. 22C). Similarly, optical micrograph showed no minerals present on the surfaces initially. After 4 weeks (28 days) of in vitro cell culture, bio-mineral development on the sample surfaces were compared. Control surface (FIG. 22D) showed accumulation of collagenous matrices only with no bio-mineral present whereas Si(ON)x surfaces (FIG. 22E) exhibited the formation of carbonate, phosphate, and collagenous matrices optical micrograph (FIG. 22F, ECM+ mineral on Si(ON)x wafer) showed the presence of hydroxy-carbonate apatite biomineral on the Si(ON)x surface, indicated by the formation of white nodules on the surface.
Figure 22B:
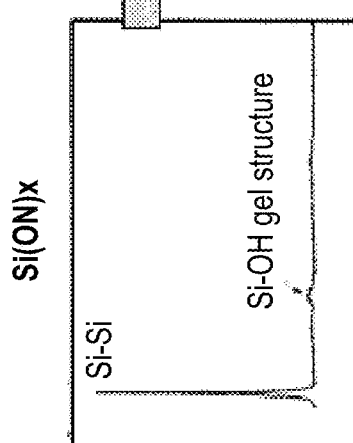
Figure 22C:
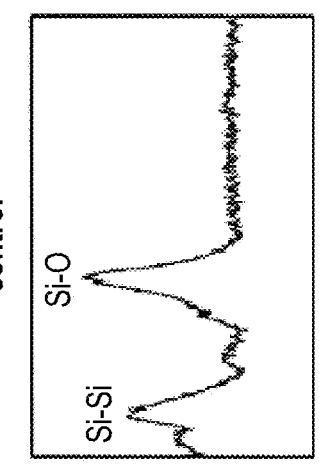
Figure 22D:
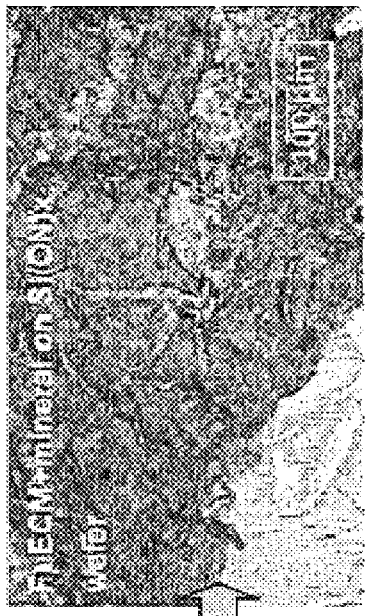
Figure 22E:
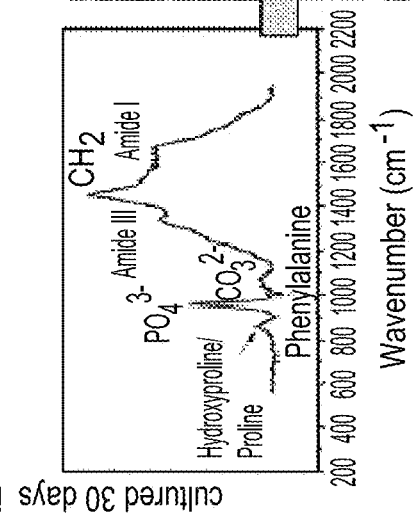
Figure 22F:
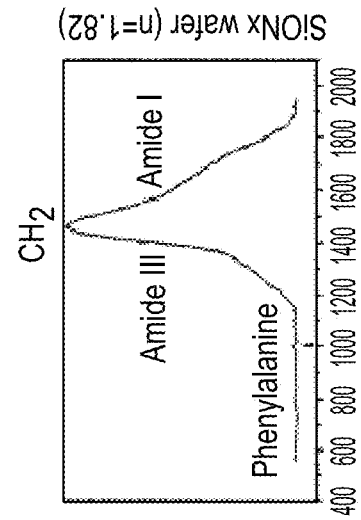

The results for ECM collagen formation on sample surfaces after in vitro cell seeding are shown in FIG. 21. SiOx surfaces facilitated the migration of cells over their surfaces on the textured area. SiNx surfaces were observed to have cells remain on the flat section of their surfaces. In both cases, the formation of "collagen-like" ECM formation was not observed. On Si(ON)x surface, though, cells were observed to form collagenous matrices, indicated by the orthogonal arrangement of the formed ECM with the surface texture orientation. Raman spectroscopy showed Amide I, Amide II and hydroxyproline peaks at a later stage (FIG. 22), which confirmed the collagen formation on Si(ON)x sample surface.

FIG. 22 demonstrates the effect of Si(ON)x surface chemistry on bio-mineral development in comparison to control surfaces. Control surface were observed to have cell formation of collagenous ECM after 4 weeks, however, no presence of biomineral was observed. Similar effects were seen for SiOx and SiNx. Si(ON)x surfaces were observed to form biomineral. This was evident by the formation of white nodules and the presence of both carbonate and phosphate functional groups on their surface. Taken together, Si(ON)x surfaces facilitated the formation of rapid biomineral formation through the maximal enhancement of osteogenic gene expression and early ECM collagen formation.

This study showed the effect that PECVD amorphous silica-based materials have on surface modification of Ti/TiO$_2$-based devices and osteoprogenitor response. PECVD-based SiOx overlays were found to be well-adherent to stoichiometric Si—O—Ti interface between SiOx and Ti/TiO$_2$. Nanoscratch results showed strong interfacial adhesion without delamination as the scratch testing progressed. Cell-free in vitro studies exhibited changes in contact angles over 24 h and changes in surface formation with the presence of carbonate apatite within a few hours of immersion. Understanding of apatite formation in vitro for bioactive silica-based materials and their dissolution has concentrated on bioactive glasses. Bioactive glasses undergo rapid ion exchange of alkali and alkaline earth metal cations with liquid protons to infiltrate the silica network. After this has occurred, surface silanols (evident by Si—OH Raman bond stretch) are available for dissolution, polymerization, and re-precipitation to form a silica gel network, which leads to apatite formation. Whereas PECVD-based silica forms surface silanols readily (93), skipping the rapid ion exchange step. Low temperature PECVD provides even more silanols on the oxide surface (68), resulting in apatite formation within 6 hours of in vitro submersion. Cell culture testing showed the presence of collagen on all materials including control surfaces, however, Si(ON)x surfaces maximally enhanced periosteal cell osteogenic gene expression and stimulated added production of carbonate apatite biomineral matrix. Therefore, these overlays support the hypothesis that they can provide structural support by exhibiting strong adhesion to the underlying Ti/TiO$_2$ layers and stimulate the rapid formation of bone-like biomineral formation.

The process flow used for these studies provides precise control over texture, surface chemistry, and surface mechanics that are exposed to cells and tissues. Optical lithography was employed due to its scalable features that can be fabricated at relatively low cost and with high reproducibility. Uses of cryogenic chlorine gas for metal etching resulted in an initial induction period before a linear period of etch depth with time. The lag time in the etch method was observed and this was owed to an initial induction period to etch through a relatively small native oxide layer of TiO$_2$, which may allow etching ions to build on surface due to highly capacitive nature of surface oxide. Etches were intended to be anisotropic, however, some degree of isotropy was observed. This was evident by the presence of angled sidewalls of etched trenches. This could be owed to the columnar grain structure of the EB-PVD Ti. Others have noted improved sidewall formation when using Ti wafers etched with cryogenic chlorine gas (94). Another possible explanation for the somewhat isotropic etch was the possible lack of delivery of a sufficiently high-density low-pressure plasma column to create anisotropic etch (95). Thermal annealing of Ti thin film yielded TiO$_2$ layer that appeared tensile. The tensile nature of the stress was expected for low temperature deposited TiO$_2$ film (96) and indicated the film was not being constrained by the underlying Ti (likely owed to its columnar grain structure). Despite these relatively small issues with etching, overall control over grain structure and etching of Ti as well as growth of thermal TiO$_2$ was well controlled and reproducible.

In this work, the properties of the PECVD-based SiOx-Ti/TiO$_2$ interface were characterized. One of the key advantages of this interface, among others, was the presence of a nearly stoichiometric Ti—O—Si bond. Several studies have indicated that the formation of this interface is owed to migration of Ti and Si atoms into each layer (97-100). Nanoscratch results further confirmed that this interface does not delaminate and that the overlay is strongly adherent, which confirmed the result (101). Moreover, because the overlay thickness is relatively small compared to the rest of the device, this offers additional benefit of high resistance to peel off stress. In comparison, bulk methods used to fabricate bioactive glass or hydroxyapatite coatings on Ti/TiO$_2$ did not adhere well. This was mainly owed to relatively high deposition temperatures, thermal expansion mismatch, large coating thickness to interface thickness (1000:1 in the case of bioactive glass) or lack of miscibility with synthetic HA and Ti/TiO$_2$ (102). PECVD, on the other hand, can be more advantageous as a relatively low-temperature method to fabricate thin and well-adherent SiOx-based overlays on Ti.

Such potential to improve fracture healing must come with an ability of the overlay materials to stimulate or enhance osteogenesis and "bone-like" biomineral formation. PECVD-based SiOx overlay resulted in the formation of Ca—PO$_4$-based hydroxyapatite formation within 6 hours. However, doping with N in Si(ON)x and SiNx resulted in hydroxycarbonate apatite formation. This led to enhanced osteogenic expression of BMP2 and LOX, which are key markers of enhanced osteogenesis. SiOx appeared to induce higher expression of OSX. Si(ON)x enhanced expression was significant relative to control levels. Si(ON)x and SiOx enhancement were not significant when compared with each other and appeared very close in average value, therefore, these levels of enhancement were deemed very similar. There is however, a significant enhancement of LOX expression when periosteal cells are exposed to Si(ON)x surfaces. LOX is a key collagen cross-linking enzyme and is responsible for increasing biomineral strength (103) (103). Without enhancement of the cross-linking enzyme at the early phase of osteogenesis, biomineral formation can be delayed. This could explain the rapid enhancement in biomineral production on Si(ON)x surfaces. Interestingly, only Si(ON)x layer induced the formation of biomineral of similar chemistry by human periosteal cells, whereas SiOx and SiNx did not. In addition, periosteal cells only had enhanced expression of LOX and deposited a collagenous ECM in orthogonally arranged structure to the patterned Si(ON)x surface, which is consistent with the formation of collagenous ECM by osteoprogenitor cells during the formation of bone matrix (76). This may be owed to the human periosteal cells requiring the presence of carbonate and phosphate on the surface to produce bone-like HCA. These results are the first evidence showing this optimal effect of N doping in SiOx to produce HCA within a few hours of in vitro immersion and resultant enhancements in osteogenesis and biomineral formation within 4 weeks.

In the Si—O—N elemental system, N acts as a substitute for O resulting in a higher atomic packing density. SiOx and SiNx maintain tetrahedral and trigonal coordination respectively, Si(ON)x, coordination has a mixture of these 2 coordination systems (78). As N concentration increases in amorphous silica-based material, the mechanical strength increases significantly (Young's modulus rises from 73 to 166 GPa whereas hardness increases from 8.32 to 17.10 GPa) (78, 104). Though annealing of amorphous silica-based bioactive glass coatings on Ti and sputter coated oxynitride films on Si have both exhibited improved mechanical strength with increasing N content (78, 80) yet the role of N in biomineralization has never been explored or understood.

In this study, there is clear evidence that N influences the chemistry of biomineral such that carbonate can be incorporated. The only evidence of a similar effect is in the deep-sea sponges in which their siliceous skeletons have been shown to incorporate carbonate species in an environment with limited soluble oxygen (105). It can be speculated that the altered glass network could provide surface site coordination more favorable to carbonate formation. However, no evidence has been shown that these deep-sea sponges incorporate N into their skeletons. It will be necessary to isolate the effect of N in biomineralization to gain a better understanding on how it impacts carbonate formation or is this an effect related to a paucity in oxygen content.

One of the intended applications of the present overlays is for traumatic fracture healing in clinical applications. The mechanisms of these layers with upstream cellular responses must be determined so that control over cellular response and biomineral formation can be achieved. In addition, animal testing will be conducted to determine how these overlays perform in an environment where hormones and biomechanical loads are present. Finally, a better understanding of the mechanisms involving biomineral formation on each of these substrates will uncover the role that N plays during apatite formation and biomineralization.

PECVD amorphous silica-based overlays are demonstrated to exhibit strong adhesion to Ti/TiO$_2$-based devices and incorporation of N is shown to enhance the osteogenesis of osteoprogenitor cells and biomineral formation. The SiOx-TiO$_2$—Ti interface showed continuity in chemical composition from the overlying SiOx layer to the TiO$_2$ layer and then onto the Ti layer. The interface exhibited strong adhesion between layers. In vitro testing showed that the incorporation of N induced the formation of increasing carbonate to phosphate ratio. The Si(ON)x layers induced osteogenesis of human periosteal cells and carbonate apatite biomineral matrix formation. The present studies and results may be used in clinical applications where surface features facilitate cellular response and biomechanical bonding. The surface chemistry provides biochemical bonding via early formation of hydroxycarbonate apatite to hasten bone matrix formation.

Example 13—Micro and Nano-Electronics

The example herein describes the use of the SiOx, SiONx, and SiNx films for applications in micro- and nano-electronics. Thin films in the Si—O—N elemental chemistry are used as dielectrics in microelectronic applications.

Figures 23A, 23B, 23C:
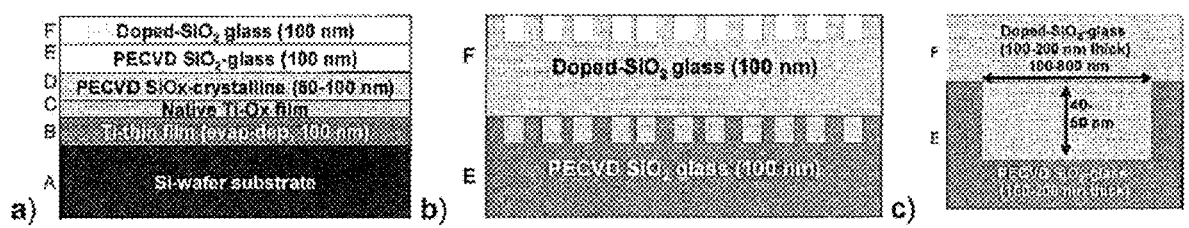
FIG. 23A-FIG. 23C.

The use of the single or multi-layered design can be used as dielectrics as illustrated In FIG. 23.

In the single layer SiOx, SiONx, or SiNx films, the film is deposited by PECVD as described above.

In a multi-layered or stacked design, the PECVD layers are fabricated on top of each other by altering the gas phase chemistry during the PECVD process for the desired film chemistry.

For example, stacked designs using SiOx as a starting layer with SiONx as a top layer have been made by first using SiH24 or TEOS as Si source and O2 as oxygen source to make SiOx films.

On top of the SiOx film, the Si(ON)x film was fabricated by changing the gas phase O/N raio.

The stacked design offers properties that can help to improve overall dielectric properties of microelectronic devices.

Multilayers can also be formed onto etched surfaces. Surfaces can be etched using photolithography or electron beam lithography.

The multi-layered design can also be seen in FIG. 11.

BIBLIOGRAPHY

The following references are specifically incorporated herein by reference:
(1) National Ambulatory Medical Care Survey 1998-2006, Centers for Disease Control and Prevention; National Center for Health Statistics, U.S. Department of Health and Human Services (2006).
(2) M O Montjovent, et al., Tissue Engineering, 11 (11-12): 1640-1649 (2005).

(3) D K Dhanwal, et al., Indian Journal of Orthopaedics, 45 (1): 15-22 (2011).
(4) A Sandukji, et al., Human & Experimental Toxicology, 30 (6): 435-42 (2011).
(5) W P Ho, et al., Journal of Cellular Biochemistry, 108 (5): 1084-93 (2009).
(6) H Nojiri, et al., Journal of bone and mineral research: the official journal of the American Society for Bone and Mineral Research, 26 (11): 2682-94 (2011).
(7) M Valko, et al., International Journal of Biochemistry & Cell Biology, 39 (1): 44-84 (2007).
(8) A Hannemann, et al., BMC Endocrine Disorders, 13: 11 (2013).
(9) V S A Vaman, et al., Toxicology Mechanisms and Methods, 23 (7): 500-508 (2013).
(10) C Y Turk, et al., Journal of International Medical Research, 32 (5): 507-512 (2004).
(11) J H E Fraser, et al., Bone, 19 (3): 223-226 (1996).
(12) M J Smietana, et al., Biochemical and Biophysical Research Communications, 403 (1): 149-153 (2010).
(13) J M Lean, et al., Journal of Clinical Investigation, 112 (6): 915-23 (2003).
(14) F Jakob, et al., Methods Enzymol, 347: 168-79 (2002).
(15) M Iwai-Yoshida, et al., J Mech Behav Biomed Mater, 13: 230-6 (2012).
(16) M Arun et al., Toxicology Mechanisms and Methods, 21 (7): 561-6 (2011).
(17) M F Ceiler, et al., Journal of the Electrochemical Society, 42 (6): 2067-2071 (1995).
(18) V G Varanasi, et al., Journal of Oral Implantology, 38 (4): 325-336 (2012).
(19) N S Tousi, et al., Materials Science & Engineering C-Materials for Biological Applications, 33 (5): 2757-2765 (2013).
(20) V G Varanasi, et al., Journal of Biomedical Materials Research Part A, 98A (2): 177-184 (2011).
(21) V G Varanasi, et al., Acta Biomaterialia, 5 (9): 3536-3547 (2009).
(22) L L Hench, Bioceramics, Journal of the American Ceramic Society, 81 (7): 1705-1728 (1998).
(23) M H Lee, et al., Biochemical and Biophysical Research Communications, 309 (3): 689-694 (2003).
(24) Y Choe, et al., Journal of Cellular Biochemistry, 113 (4): 1426-36 (2012).
(25) R Mahreen, et al., International Journal of Diabetes in Developing Countries, 30 (1): 49-51 (2010).
(26) W P Ho, et al., Journal of Cellular Biochemistry, 108 (5): 1084-93 (2009).
(27) J E Kim, et al., Journal of Bone and Mineral Research, 24 (6): 1055-1065 (2009).
(28) S A E Badr, et al., Turk Geriatri Dergisi-Turkish Journal of Geriatrics, 11 (4): 174-180 (2008).
(29) E Fabian, et al., Wiener Klinische Wochenschrift, 123 (3-4): 88-93 (2011).
(30) N Saito, et al., J Biomed Mater Res, 47 (1): 104-10 (1999).
(31) A Vrailas-Mortimer, et al., Experimental Gerontology, 47 (9): 712-722 (2012).
(32) E J Carragee, et al., Spine J, 11 (6): 471-91 (2011).
(33) M Horie, et al., Inhalation toxicology, 24 (7): 391-400 (2012).
(34) A Moshaverinia, et al., Journal of Materials Chemistry, 21 (5): 1319-1328 (2011).
(35) X Lu, Y Leng, Journal of Biomedical Materials Research Part B-Applied Biomaterials, 90B (1): 438-445 (2009).
(36) E Lamers, et al., Biomaterials, 31 (12): 3307-3316 (2010).
(37) S Lenhert, et al., Biomaterials, 26 (5): 563-70 (2005).
(38) L L Jiang, et al., Materials Science & Engineering C-Materials for Biological Applications, 32 (4): 742-748 (2012).
(39) A Bachar, et al., Journal of Non-Crystalline Solids, 358 (3): 693-701 (2012).
(40) P Sepulveda, et al., Journal of Biomedical Materials Research, 58 (6): 734-740 (2001).
(41) E Saiz, et al., Biomaterials, (23): 3749-3756 (2002).
(42) L L Hench, Journal of the European Ceramic Society, 29 (7): 1247-1265 (2009).
(43) S Foppiano, et al., Acta Biomaterialia, 3 (5): 765-771 (2007).
(44) V G Varanasi, et al., Journal of the Electrochemical Society, 152 (1): C7-C14 (2005).
(45) V G Varanasi, et al., Materials Science and Engineering a-Structural Materials Properties Microstructure and Processing, 528 (3): 978-985 (2011).
(46) V G Varanasi, et al., Journal of Alloys and Compounds, 470 (1-2): 354-359 (2009).
(47) V G Varanasi, et al., Thin Solid Films, 516 (18): 6133-6139 (2008).
(48) V G Varanasi, et al., High Temperature Ceramic Matrix Composites, 5: 595-601 (2005).
(49) M Keskin, et al., Plastic and reconstructive surgery, 122 (2): 400-409 (2008).
(50) V P Swamp, et al., Metallomics, 3 (11): 1218-26 (2011).
(51) L Du, et al., Talanta, 101 11-6 (2012).
(52) G Z Xiao, et al., Journal of Bone and Mineral Research, 17 (1) 101-110 (2002).
(53) N Nabavi, et al., PloS one, 7 (9): e46265 (2012).
(54) D Boonyawan, et al., Surface and Coatings Technology, 205, Supplement 2 (O): S552-S557 (2011).
(55) C C Lin, et al., Biomaterials, 26 (17): 3655-62 (2005).
(56) M E Pryor, et al., Journal of clinical periodontology, 32 (9): 966-72 (2005).
(57) G Shi, et al., Langmuir: the ACS journal of surfaces and colloids, 25 (17): 9639-43 (2009).
(58) S Sarkar, et al., Biomaterials, 27 (27): 4775-4782 (2006).
(59) D Gallego, et al., Materials Science & Engineering C Biomimetic and Supramolecular Systems, 28 (3): 353-358 (2008).
(60) S. R. Pitts, et al., National hospital ambulatory medical care survey: 2006 emergency department summary, Natl Health Stat Report 7 (7): 1-38 (2008).
(61) M.-O. Montjovent, et al., Tissue engineering, 11 (11-12), 1640-1649 (2005).
(62) E. Fabian, et al., Nutritional supplementation affects postoperative oxidative stress and duration of hospitalization in patients with hip fracture, Wiener Klinische Wochenschrift, 123 (3-4), 88-93 (2011).
(63) A. Sandukji, et al., Human & experimental toxicology, 30 (6), 435-42 (2011).
(64) A. Hannemann, et al., Reference intervals for serum osteocalcin concentrations in adult men and women from the study of health in Pomerania, BMC Endocrine Disorders, 13, 11 (2013).
(65) N. S. Tousi, et al., Materials Science & Engineering C-Materials for Biological Applications, 33 (5), 2757-2765 (2013).
(66) Canullo L, Dellavia C., Sinus lift using a nanocrystalline hydroxyapatite silica gel in severely resorbed maxillae: histological preliminary study, Clinical implant dentistry and related research, 11 Suppl 1:e7-13 (2009).

(67) Banwart J C, et al., Iliac crest bone graft harvest donor site morbidity, A statistical evaluation, 20:1055-60 (Phila Pa. 1976) (1995).
(68) M. Iwai-Yoshida, et al., Journal of the mechanical behavior of biomedical materials, 13, 230-236 (2012).
(69) S. Foppiano, et al., Acta biomaterialia, 3 (5), 765-771 (2007).
(70) N. S. Tousi, et al., Materials Science and Engineering: C, 33 (5), 2757-2765 (2013).
(71) M. Ceiler, et al., Journal of the Electrochemical Society, 142 (6), 2067-2071 (1995).
(72) F. Cverna, Thermal properties of metals, ASM International, Materials Park, Ohio 2002.
(73) U. Diebold, The surface science of titanium dioxide, Surface science reports, 48 (5), 53-229 (2003).
(74) S. Lopez-Esteban, et al., Journal of the European Ceramic Society, 23 (15), 2921-2930 (2003).
(75) J. Gomez-Vega, et al., Processing. Biomaterials, 21 (2), 105-111 (2000).
(76) J. Kobayashi, et al., Growth of III-nitride films on mismatched substrates without conventional low temperature nucleation layers. In ed., Ed. Eds. Google Patents: Vol. pApp. (2005).
(77) V. G. Varanasi, et al., Journal of The Electrochemical Society, 152 (1), C7-C14 (2005).
(78) V. G. Varanasi, et al., Materials Science and Engineering, 528 (3), 978-985 (2011).
(79) V. Varanasi, et al., Acta biomaterialia, 5 (9), 3536-3547 (2009).
(80) V. G. Varanasi, et al., Thermodynamic analysis and growth of ZrO 2 by chloride chemical vapor deposition, Thin Solid Films, 516 (18), 6133-6139 (2008).
(81) Y. Liu, et al., Materials Science and Engineering, 489 (1), 294-301 (2008).
(82) A. Bachar, et al., Journal of the mechanical behavior of biomedical materials, 23, 133-148 (2013).
(83) J. Gomez-Vega, et al., Journal of biomedical materials research, 46 (4), 549-559 (1999).
(84) H. Jeon, et al., A mini-review: Journal of Biomedical Materials Research Part B: Applied Biomaterials, 102 (7), 1580-1594 (2014).
(85) K. Seunarine, et al., A hierarchical response of cells to perpendicular micro- and nanometric textural cues, Nano-Bioscience, IEEE Transactions, 8 (3), 219-225 (2009).
(86) W. Asghar, et al., Nanotechnology, 23 (47), 475601 (2012).
(87) T. Albrektsson, et al., The International journal of prosthodontics, 17 (5), 536-543 (2003).
(88) A. S. Badami, et al., Biomaterials, 27 (4), 596-606 (2006).
(89) T. Odatsu, et al., Journal of Biomedical Materials Research Part A (2015).
(90) H. Demirkiran, et al., XANES analysis of calcium and sodium phosphates and silicates and hydroxyapatite-Bioglass® 45S5 co-sintered bioceramics, Materials Science and Engineering, 31 (2), 134-143 (2011).
(91) J. Rajendran, et al., XANES analysis of dried and calcined bones, Materials Science and Engineering, 2013, 33 (7), 3968-3979 (2013).
(92) H. K. W. Kim, et al., Bone, 54, 141-150 (2013).
(93) I. Notingher, et al., Journal of molecular structure, 744, 179-185 (2005).
(94) G. Puppels, et al., Nature, 347, 301-303 (1990).
(95) F. Golightly, et al., The influence of yttrium additions on the oxide-scale adhesion to an iron-chromium-aluminum alloy, Oxidation of Metals, 10 (3), 163-187 (1976).
(96) E. J. Szili, et al., Surface science, 602 (14), 2402-2411 (2008).
(97) M. Domanski, R., et al., Nanotechnology 2012, 23 (6), 065306.
(98) S. McAuley, et al., Journal of physics and applied physics, 34 (18), 2769 (2001).
(99) M. Burgos, et al., Journal of sol-gel science and technology, 16 (3), 267-276 (1999).
(100) D. Dunn, et al., Journal of Applied Physics, 89 (5), 2635-2640 (2001).
(101) Y. Wang, et al., The microstructure and its high-temperature annealing behaviours of a-Si:O:H film (2001).
(102) T. A. Jurgens, et al., The Journal of Physical Chemistry, 99 (2): 731-743 (1995).
(103) M. L. Hitchman, et al., The Electrochemical Society interface, 10 (2): 40-45 (2001).
(104) J. Lee, H, et al., Journal of the American Ceramic Society, 86 (10): 1797-1799 (2003).
(105) P. Habibovic, et al., Journal of the American Ceramic Society, 85 (3): 517-522 (2002).
(106) M. Saito, et al., Osteoporosis international, 17 (7): 986-995 (2006).
(107) M. Vila, et al., Journal of applied physics, 94 (12): 7868-7873 (2003). H. Ehrlich, et al., Advanced Functional Materials, 21 (18): 3473-3481 (2011).

What is claimed is:

1. A method for preparing a treated surface on a medical device comprising:
providing a medical device having a cleaned surface;
depositing an amorphous silica-based thin film overlay on said cleaned surface using a chemical vapor deposition system with plasma enhancement in the presence of a silica-based reagent, wherein said chemical vapor deposition system is a Si—O—N chemical deposition system comprising a source of Si, oxygen and nitrogen, and wherein said silica-based reagent comprises $SiH_4$ or TEOS to form a first treated surface having a thin film amorphous silica-based overlay with a Si—O— or Si—O—N surface interface;
preparing a second treated surface on a second cleaned surface to provide a second treated surface, and
stacking said first treated surface and said second treated surface to provide a stacked layer of silicon-based thin films.

2. The method of claim 1 wherein the silica-based reagent comprises $SiH_4$.

3. The method of claim 1 wherein the surface is a metal surface or a biopolymer surface.

4. The method of claim 1 wherein the first treated surface has a thin film amorphous silica-based overlay with a stoichiometric Si—O— or Si—O—N surface interface.

5. The method of claim 1 wherein the amorphous silica-based thin film overlay has a thickness of less than 1000 nm.

6. The method of claim 1 wherein the amorphous silica-based thin film overlay has a thickness of about 100 nm to about 1000 nm.

7. The method of claim 1 wherein the first treated surface comprises an etched treated surface.

8. The method of claim 7 wherein the etched treated surface comprises a nano-micro-grooved etched surface pattern.

9. The method of claim 8 wherein the etched treated surface comprises a series of nano/micro-grooves having a 100 nm trench depth and a 2 µm trench width.

10. The method of claim 1 wherein the amorphous silica-based overlay comprises $SiN_4$ or $SiO_2$.

11. The method of claim 1 comprising a carbonate appetite biomineral matrix on the first treated surface.

12. The method of claim 1 wherein the medical device is an implantable dental medical device.

13. The method of claim 1 wherein the medical device is an implantable orthopedic medical device.

14. The method of claim 1 wherein the first treated surface is a glass, ceramic or metal surface.

15. The method of claim 1 wherein the first treated surface comprises titanium.

16. The method of claim 1 wherein the chemical vapor deposition system with plasma enhancement in the presence of a silica-based reagent is conducted at a chamber pressure of 900 mTorr.

17. The method of claim 1 wherein the amorphous silica-based thin film overlay has a thickness of about 100 nm.

18. The method of claim 1 wherein the chemical vapor deposition system with plasma enhancement in the presence of a silica-based reagent is conducted at an ICP power of 75 W.

\* \* \* \* \*

UNITED STATES PATENT AND TRADEMARK OFFICE
CERTIFICATE OF CORRECTION

PATENT NO. : 10,898,618 B2
APPLICATION NO. : 14/848107
DATED : January 26, 2021
INVENTOR(S) : Venu Varanasi It is certified that error appears in the above-identified patent and that said Letters Patent is hereby corrected as shown below:

In the Specification

Column 9, Line 10, there should be a "." after the word "nanofilms"

Column 12, Line 26, the text should read "FIG. 19B(2),"

Column 18, Line 3, the text should read "Si(ON)x - modified..."

Column 40, Line 29, the author's last name should read "Swarup"

In the Claims

Claim 11 (Column 43, Line 1-2), "...a carbonate appetite" should read "...a carbonate apatite"

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*